(12) United States Patent
Zee et al.

(10) Patent No.: US 8,787,638 B2
(45) Date of Patent: Jul. 22, 2014

(54) METHOD AND DEVICE FOR RETINAL IMAGE ANALYSIS

(75) Inventors: Benny Chung-Ying Zee, Hong Kong (CN); Jack Jock-Wai Lee, Hong Kong (CN); Esther Qing Li, Hong Kong (CN)

(73) Assignee: The Chinese University of Hong Kong, Hong Kong (CN)

( * ) Notice: Subject to any disclaimer, the term of this patent is extended or adjusted under 35 U.S.C. 154(b) by 123 days.

(21) Appl. No.: 13/441,181

(22) Filed: Apr. 6, 2012

(65) Prior Publication Data

US 2012/0257164 A1     Oct. 11, 2012

Related U.S. Application Data

(60) Provisional application No. 61/473,027, filed on Apr. 7, 2011, provisional application No. 61/588,815, filed on Jan. 20, 2012.

(51) Int. Cl.
*G06K 9/00*       (2006.01)

(52) U.S. Cl.
USPC .......................................................... 382/128

(58) Field of Classification Search
None
See application file for complete search history.

(56) References Cited

U.S. PATENT DOCUMENTS

| | | | |
|---|---|---|---|
| 7,474,775 B2 | 1/2009 | Abràmoff et al. | |
| 7,524,061 B2 | 4/2009 | Yan et al. | |
| 7,668,351 B1 | 2/2010 | Soliz et al. | |
| 7,848,558 B2 | 12/2010 | Giger et al. | |
| 2007/0258630 A1* | 11/2007 | Tobin et al. | 382/128 |
| 2010/0111376 A1* | 5/2010 | Yan et al. | 382/118 |
| 2010/0142766 A1* | 6/2010 | Fleming | 382/117 |
| 2011/0026789 A1* | 2/2011 | Hsu et al. | 382/128 |
| 2011/0160562 A1 | 6/2011 | De Oliveira e Ramos et al. | |
| 2013/0114041 A1* | 5/2013 | Iftekharuddin et al. | 351/206 |

FOREIGN PATENT DOCUMENTS

WO     2009/126112 A1     10/2009

OTHER PUBLICATIONS

Teng et al., "Progress towards automated diabetic ocular screening: a review of image analysis and intelligent systems for diabetic retinopathy," *Medical & Biological Engineering & Computing* 40:2-13, Dec. 31, 2002.
International Search Report for PCT/CN2012/000456, mailed Jul. 12, 2012, 5 Pages.
Written Opinion of PCT/CN2012/000456, mailed Jul. 12, 2012, 6 Pages.
Abràmoff et al., "Evaluation of a System for Automatic Detection of Diabetic Retinopathy from Color Fundus Photographs in a Large Population of Patients With Diabetes," *Diabetes Care* 31(2):193-198, Feb. 2008.
Acharaya et al., "An Integrated Index for the Identification of Diabetic Retinopathy Stages Using Texture Parameters," *Journal of Medical Systems* 36:2011-2020, 2012.
Acharya et al., "Application of Higher Order Spectra for the Identification of Diabetes Retinopathy Stages," *Journal of Medical Systems* 32:481-488, 2008.
Acharya et al., "Automated Diagnosis of Glaucoma Using Texture and Higher Order Spectra Features," *IEEE Transactions on Information Technology in Biomedicine* 15(3):449-455, May 2011.

(Continued)

*Primary Examiner* — Atiba O Fitzpatrick
(74) *Attorney, Agent, or Firm* — Seed IP Law Group PLLC

(57) ABSTRACT

The present application provides methods and devices for diagnosing and/or predicting the presence, progression and/or treatment effect of a disease characterized by retinal pathological changes in a subject.

55 Claims, 10 Drawing Sheets

(56) References Cited

OTHER PUBLICATIONS

Figure 1:
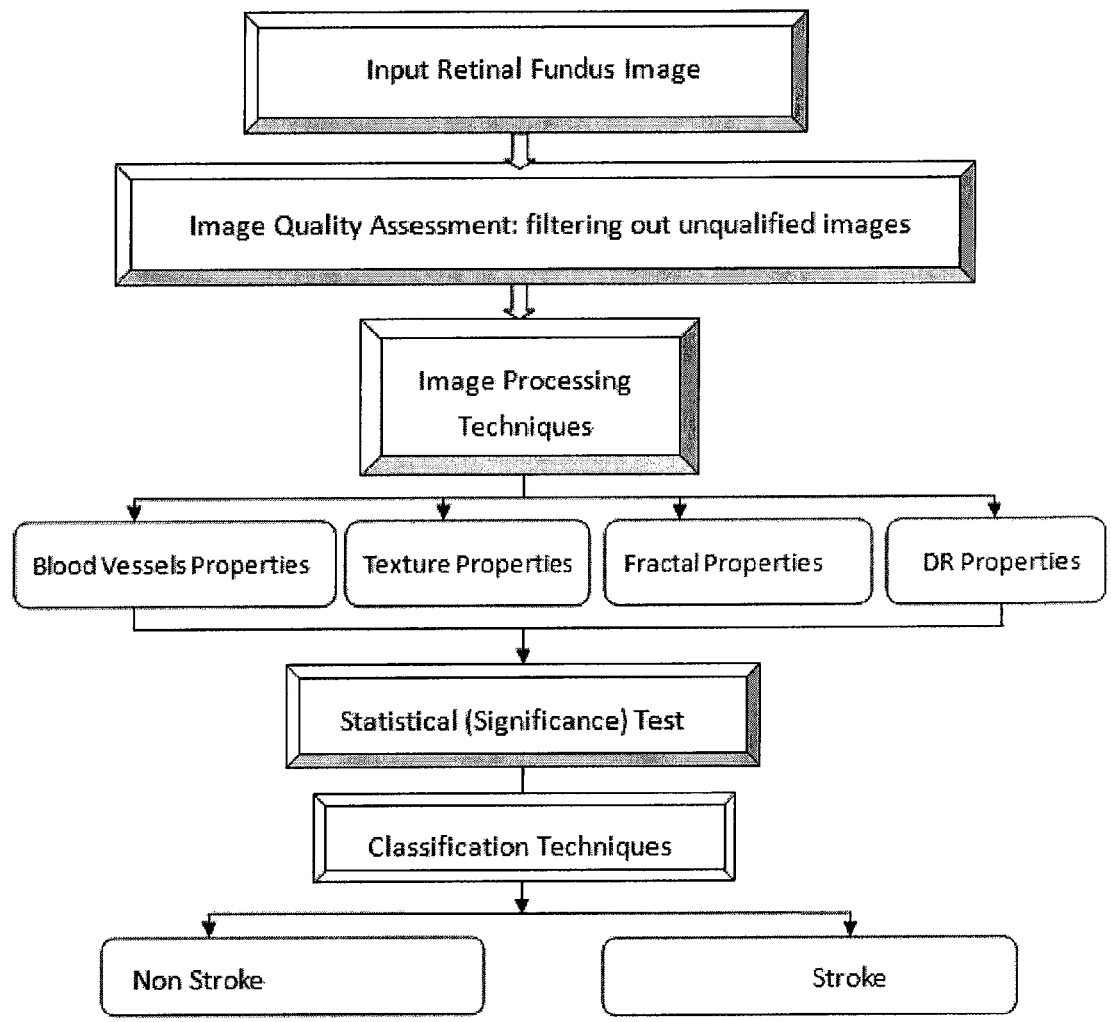

Andjelkovic et al., "Application of Multifractal Analysis on Medical Images," *WSEAS Transactions on Information Science and Applications* 5(11):1561-1572, Nov. 2008.
Avakian et al., "Fractal analysis of region-based vascular change in the normal and non-proliferative diabetic retina," *Current Eye Research* 24(4):274-280, 2002.
Azemin et al., "Fusion of Multiscale Wavelet-Based Fractal Analysis on Retina Image for Stroke Prediction," *32nd Annual International Conference of the IEEE EMBS*, Buenos Aires, Argentina, Aug. 31, 2010-Sep. 4, 2010 pp. 4308-4311.
Azemin et al., "Retinal Stroke Prediction Using Logistic-Based Fusion of Multiscale Fractal Analysis," *Imaging Systems and Techniques (IST)*, 2010 IEEE International Conference, pp. 125-128, Jul. 1-2, 2010.
Azemin et al., "Robust Methodology for Fractal Analysis of the Retinal Vasculature," *IEEE Transactions on Medical Imaging* 30(2):243-250, Feb. 2011.
Bartoń, Package 'MuMIn', (37 pages) Jul. 18, 2012.
Bland et al., "A note on the use of the intraclass correlation coefficient in the evaluation of agreement between two methods of measurement," *Computers in Biology and Medicine* 20(5):337-340, 1990.
Bland et al., "Statistical methods for assessing agreement between two methods of clinical measurement," *Lancet i*(8476):307-310, 1986.
Bock et al., "Glaucoma risk index: Automated glaucoma detection from color fundus images," *Medical Image Analysis* 14:471-481, 2010.
Bremananth et al., "Wood Species Recognition Using GLCM and Correlation," *2009 International Conference on Advances in Recent Technologies in Communication and Computing* 615-619, 2009.
Buckland et al., "Model Selection: An Integral Part of Inference," *Biometrics* 53(2):603-618, Jun. 1997.
Chandran et al., "Pattern Recognition Using Invariants Defined from Higher Order Spectra: 2-D Image Inputs," *IEEE Transactions on Image Processing* 6(5):703-712, May 1997.
Chang et al., "Texture Analysis and Classification with Tree-Structured Wavelet Transform," *IEEE Transactions on Image Processing* 2(4):429-441, Oct. 1993.
Chen, et al., "Texture Classification Using Statistical Geometrical Features," *Image Processing—IEEE*, pp. 446-450 1994.
Dasu et al., "An Application of Decorrelation and Linear Contrast Stretching Methods on Satellite Images," *VSRD International Journal of Electrical, Electronics & Communication Engomeering* 1(7):402-410, 2011.
Daxer, "Characterisation of the neovascularisation process in diabetic retinopathy by means of fractal geometry: diagnostic implications," *Graefe's Archive for Clinical and Experimental Ophthalmology* 231:681-686, 1993.
Daxer, "The fractal geometry of proliferative diabetic retinopathy: implications for the diagnosis and the process of retinal vasculogenesis," *Current Eye Research* 12(12):1103-1109, 1993.
Dettling et al., "Supervised Gene Clustering With Penalized Logistic Regression," Research Report No. 115, *Seminar für Statistik ETH*, Zürich, Switzerland, (20 pages) May 2003.
Doubal et al., "Fractal analysis of retinal vessels suggests that a distinct vasculopathy causes lacunar stroke," *Neurology* 74:1102-1107, Apr. 6, 2010.
Family et al., "Fractal pattern formation in human retinal vessels," *Physica D* 38:98-103 1989.
Faust et al., "Algorithms for the Automated Detection of Diabetic Retinopathy Using Digital Fundus Images: A Review," *Journal of Medical Systems* 36:145-157, 2012.
Fleming et al., "Automated Detection of Blot Haemorrhages as a Sign of Referable Diabetic Retinopathy," *Med Image Understand Analysis* 235-239, (5 pages) 2008.
Fleming et al., "Automated detection of exudates for diabetic retinopathy screening," *Physics in Medicine and Biology* 52:7385-7396, 2007.

Fleming et al., "Automatic detection of retinal anatomy to assist diabetic retinopathy screening," *Physics in Medicine and Biology* 52:331-345, 2007.
Fleming et al., "The role of haemorrhage and exudate detection in automated grading of diabetic retinopathy," *British Journal of Ophthalmology* 94:706-711, 2010.
García et al., "Neural Network Based Detection of Hard Exudates in Retinal Images," *Computer Methods and Programs in Biomedicine*, 93: 9-19, 2009.
Goatman et al., "Detection of New Vessels on the Optic Disc Using Retinal Photographs," *IEEE Transactions on Medical Imaging* 30(4):972-979, Apr. 2011.
Hassan et al., "Detection of Neovascularization in Diabetic Retinopathy," *Journal of Digital Imaging* 25:437-444, 2012.
Hatanaka et al., "Improvement of Automatic Hemorrhages Detection Methods using Brightness Correction on Fundus Images," *Medical Imaging 2008: Computer-Aided Diagnosis*, in *Proceedings of SPIE* 69153(69153E), 2008, 10 pages.
Hubbard et al., "Methods for Evaluation of Retinal Microvascular Abnormalities Associated with Hypertension/Sclerosis in the Atherosclerosis Risk in Communities Study," *Ophthalmology* 106(12):2269-2280, Dec. 1999.
Jaafar et al., "Automated detection of exudates in retinal images using a split-and-merge algorithm," *18th European Signal Processing Conference*, Aalborg, Denmark, Aug. 23-27, pp. 1622-1626, 2010.
Kande et al., "Automatic Detection of Microaneurysms and Hemorrhages in Digital Fundus Images," *Journal of Digital Imaging* 23(4):430-437, Aug. 2010.
Kande et al., "Segmentation of Exudates and Optic Disc in Retinal Images," *Sixth Indian Conference on Computer Vision, Graphic & Image Processing*, pp. 535-542, 2008.
Kawasaki et al., "Fractal dimension of the retinal vasculature and risk of stroke: a nested case-control study," *Neurology* 76:1766-1770, May 17, 2011.
Kwon et al., "Retinopathy as an indicator of silent brain infarction in asymptomatic hypertensive subjects," *Journal of the Neurological Sciences* 252:159-162, 2007.
Liew et al., "The Retinal Vasculature as a Fractal: Methodology, Reliability, and Relationship to Blood Pressure," *Ophthalmology* 115(11):1951-1956, Nov. 2008.
Lopes et al., "Fractal and multifractal analysis: A review," *Medical Image Analysis* 13:634-649, 2009.
MacGillivray et al., "A reliability study of fractal analysis of the skeletonised vascular network using the "box-counting" technique," *Proceedings of the 28th IEEE EMBS Annual International Conference*, New York City, USA, pp. 445-448, Aug. 30-Sep. 3, 2006.
MacGillivary et al., "Fractal analysis of the retinal vascular network in fundus images," in *Proceedings of the 29th Annual International Conference of the IEEE EMBS Cité Internationale*, Lyon, France, Aug. 23-26, 2007, SuA13.2, pp. 6455-6458.
Mainster, "The Fractal Properties of Retinal Vessels: Embryological and Clinical Implications," *Eye* 4:235-241, 1990.
Margo et al., "The Reliability of Clinical Methods in Ophthalmology, " *Survey of Ophthalmology* 47(4):375-386, Jul.-Aug. 2002.
Masters, "Fractal Analysis of the Vascular Tree in the Human Retina," *Annual Review of Biomedical Engineering* 6:427-452, 2004.
Niemeijer et al., "Automated Detection and Differentiation of Drusen, Exudates, and Cotton-Wool Spots in Digital Color Fundus Photographs for Diabetic Retinopathy Diagnosis," *Investigative Ophthalmology & Visual Science* 48(5):2260-2267, May 2007.
Niemeijer et al., "Automatic Detection of Red Lesions in Digital Color Fundus Photographs," IEEE Transactions on Medical Imaging 24(5):584-592, May 2005.
Osareh et al., "Automated identification of diabetic retinal exudates in digital colour images," *Ophthalmology* 87:1220-1223, 2003.
Patton et al., "Retinal image analysis: Concepts, applications, and potential," *Progress in Retinal Eye Research* 25:99-127, 2006.
Petropulu, "Higher-Order Spectral Analysis," Prentice Hall Inc., Englewood Cliffs, NJ, (15 pages) 1993.
Philip et al., "The efficacy of automated "disease/no disease" grading for diabetic retinopathy in a systematic screening programme," *British Journal of Ophthalmology* 91(11):1512-1517, May 15, 2007.

(56) References Cited

OTHER PUBLICATIONS

Pietikäinen et al., "Rotation-invariant texture classification using feature distributions," *Pattern Recognition* 33(1):43-52, 2000.

Pose-Reino et al., "Regression of Alterations in Retinal Microcirculation Following Treatment for Arterial Hypertension," *The Journal of Clinical Hypertension* 8(8):590-595, Aug. 2006.

Remeseiro et al., "Automatic Drusen Detection from Digital Retinal Images: AMD Prevention," Moreno-Díaz et al. (Eds.), EUROCAST LNCS 5717, pp. 187-194, 2009.

Reza et al., "Automatic Tracing of Optic Disc and Exudates from Color Fundus Images Using Fixed and Variable Thresholds," *Journal of Medical Systems* 33:73-80, 2009.

Selesnick et al., "The Dual-Tree Complex Wavelet Tranform," IEEE *Signal Processing Magazine*, 123-151, Nov. 2005.

Shivaram et al., "Automated Detection and Quantification of Haemorrhages in Diabetic Retinopathy Images Using Image Arithmetic and Mathematical Morphology Methods," *International Journal of Recent Trends in Engeering* 2(6):174-176, Nov. 2009.

Sinthanayothin et al., "Automated detection of diabetic retinopathy on digital fundus images," *Diabetic Medicine* 19:105-112, 2002.

Sopharak et al., "Automatic Exudates Detection on Thai Diabetic Retinopathy Patients' Retinal Images," *Proceedings of the 2006 ECTI International Conference*, pp. 709-712, May 2006.

Sopharak et al., "Machine learning approach to automatic exudate detection in retinal images from diabetic patients", *Journal of Modern Optics* 57(2):124-135, 2010.

Stošić et al., "Multifractal Analysis of Human Retinal Vessels," *IEEE Transactions on Medical Imaging* 25(8):1101-1107, Aug. 2006.

Takerkart et al., "A quantification framework for post-lesion neovascularization in retinal angiography," *Proceedings of the 5th IEEE International Symposium on Biomedical Imaging*, pp. 1457-1460, May 14-17, 2008.

Tan et al., "Study of normal ocular thermogram using textural parameters," *Infrared Physics & Technology* 53:120-126, 2010.

Tuceryan et al., "Chapter 2.1: Texture Analysis," The Handbook of Pattern Recognition and Computer Vision ($2^{nd}$ Edition), World Scientific Publishing Co., pp. 207-248, 1998.

Usher et al., "Automated detection of diabetic retinopathy in digital retinal images: a tool for diabetic retinopathy screening," *Diabetic Medicine* 21:84-90, 2003.

Vovk et al., "A Review of Methods for Correction of Intensity Inhomogeneity in MRI," *IEEE Transactions on Medical Imaging* 26(3):405-421, Mar. 2007.

Walter et al., "A Contribution of Image Processing to the Diagnosis of Diabetic Retinopathy—Detection of Exudates in Color Fundus Images of the Human Retina," *IEEE Transactions on Medical Imaging* 21(10):1236-1243, Oct. 2002.

Welfer et al., "A coarse-to-fine strategy for automatically detecting exudates in color eye fundus images," *Computerized Medical Imaging and Graphics* 34:228-235, 2010.

Wendt et al., "Wavelet leader multifractal analysis for texture classification.", *16th IEEE International Conference on Image Processing (ICIP)*, pp. 3829-3832, Nov. 7-10, 2009.

Wong et al., "Hypertensive Retinopathy," *The New England Journal of Medicine* 351(22):2310-2317, Nov. 25, 2004.

Wong et al., "Prospective cohort study of retinal vessel diameters and risk of hypertension," *BMJ* 329:799-800, Jun. 2, 2004.

Wong et al., "Retinal Microvascular Abnormalities and their Relationship with Hypertension, Cardiovascular Disease, and Mortality," *Survey of Ophthalmology* 46(1):59-80, Jul.-Aug. 2001.

Xu et al., "Viewpoint invariant texture description using fractal analysis," *International Journal of Computer Vision* 83:85-100, 2009.

Yazid et al., "Exudates segmentation using inverse surface adaptive thresholding," *Measurement* 45:1599-1608, 2012.

Zana et al., "Segmentation of Vessel-Like Patterns Using Mathematical Morphology and Curvature Evaluation," *IEEE Transactions on Image Processing* 10(7):1010-1019, Jul. 2001.

Zhang et al., "A Modified Matched Filter with Double-Sided Thresholding for Screening Proliferative Diabetic Retinopathy," *IEEE Transactions of Information Technology in Biomedicine* 13(4):528-534, Jul. 2009.

Zheng et al., "Automatic Correction of Intensity Nonuniformity From Sparseness of Gradient Distribution in Medical Images," *12th International Conference on Medical Image Computing and Computer Assisted Intervention*, London, UK, 8 pages, Sep. 20-24, 2009.

\* cited by examiner

A

B

C

D

Category 1-No tortuous

Category 2-Tortuous

Category 2-Tortuous

METHOD AND DEVICE FOR RETINAL IMAGE ANALYSIS

CROSS-REFERENCES TO RELATED APPLICATIONS

This application claims the benefit of U.S. Provisional Patent Applications No. 61/473,027 filed on Apr. 7, 2011 and No. 61/588,815 filed on Jan. 20, 2012, the contents of which are hereby incorporated by reference in their entireties.

BACKGROUND

1. Technical Field

The present application generally relates to a method and device for diagnosing and/or predicting the presence, progression and/or treatment effect of a disease. In particular, the present application relates to a method and device for diagnosing and/or predicting the presence, progression and/or treatment effect of a disease characterized by retinal pathological changes in a subject.

2. Description of the Related Art

Color retina image is the only way with direct inspection of blood vessel and its pathology change through the whole body. It not only reflects retina disease but also reflects risks of systemic diseases, such as stroke.

Large epidemiological studies showed many retina characteristics which related to long term hypertension and/or diabetes were associated with stroke incidence or prevalence. Those retina characteristics detected included retina vessel diameter, arteriole-venule nipping, retinopathy, etc. However, there are new retina characteristics that could provide more information on stroke patient classification, such as vessel tortuosity, vessel asymmetry. Furthermore, the interaction of the retina characteristics also provided very important information to classify patients with stroke from those without stroke. We have shown in our clinical study that the result contributed to the classification of patients with stoke from those without stroke using retina vessel tortuosity and asymmetry and interactions of retina characteristics.

Apart from the new retina information we detected manually for stroke classification, computerized automatic analytical system based on fractal analysis, high order spectral analysis, and statistical texture analysis can also classify patients with stroke from those without stoke based on the analysis of color retina images. The data extracted from the automatic system correlated well with the clinical retina characteristics and their interaction. With such correlations, we demonstrated that the automatic analytical system captured the clinically important characteristics over and above the level that can be done manually, this can be expanded to other eye diseases with possible clinical interpretation.

The retinal pathological changes have been shown to be associated with many diseases, including systematic diseases, e.g. stroke, hypertension, diabetes, cardiovascular diseases including coronary heart disease and cerebral vascular disease; and eye diseases, e.g. glaucoma, retinopathy due to prematurity, papilloedema, macular hole, and age-related macular degeneration.

Many important eye diseases as well as systemic diseases manifest themselves in the retina. Cardiovascular disease manifests itself in the retina in a number of ways. Hypertension and atherosclerosis cause changes in the ratio between the diameter of retinal arteries and veins, known as the A/V ratio. A decrease in A/V ratio such as thinning of the arteries and widening of veins, is associated with an increased risk of stroke [b1]. Recent research has also shown that the branching pattern of retinal arterial and venous systems have fractal characteristics [b2]. For instance, Patton N, Aslam T and et al., suggested that retinal vascular image analysis is a potential screening tool for cerebrovascular disease. They mentioned that the fractals offer a natural, global, comprehensive description of the retinal vascular tree because they take into account both the changes in retinal vessel caliber and changes in branching pattern. Other studies related with retinal vessels' characteristics are also provided by Mainster M. A., and Daxer A., they pointed out that the retinal arterial and venous patterns have fractal dimensions of 1.62+0.05 and 1.7+0.07, also the fractal dimension of retinal vessel patterns with neovascularisation at or near the optic disc (NVD) is about 1.8 comparing with the control group of about 1.7 [b3-4]. However, MacGillivary T. J., Doubal F. N. and et., compared monofractal and multifractal analysis of human retinal vasculature and they indicated that multifractal approach is more efficient for detecting small changes to the retinal vasculature. Therefore, it is reasonable to believe that monofractal and multifractal analysis of human retinal vasculature are both necessary. Hence, fractal geometry provides a global and more accurate description of anatomy of the eye than classical geometry. Fractal patterns characterize how vascular patterns span the retina and can therefore provide information about the relationship between vascular pattern and retinal disease.

Recently Hsu W., Lee M. L. and Wong T. Y. have developed a platform (patented) for automated analysis of a retinal image, including automatically tracing one or more paths of one or more vessels of a retinal image, and such obtained information may be useful in forming a diagnosis of a medical condition [b5]. It also developed an automated retinal image analysis system and/or used the fractal analysis technique to provide disease risk prediction, such as hypertension. However, the approach of tracing vessels is quite retinal image quality dependent comparing to other approaches. Also, the zone defining vessel measurements lack flexibility in practical applications, i.e., the image has to have the optic disc in the middle of the image, it may not cover all useful information if the optic disc is not placed in the middle. Moreover, some useful (or partially useful) non-retinal vasculature related information may have been missed and more importantly almost all of retinal image analysis ignored the effect from the interactions between factors of the vessel measurements, and/or with other factors such as High order spectra (HOS) and texture analysis related risk factors. Acharya R., Chua C. K. and et al., have found the application of non-linear features of the HOS was more suitable for the detection of shapes and thus they apply this technique for the identification of diabetes Retinopathy stages [b6]. Dobrescu R., Dobrescu M. and et al., applied the method based on combined texture and fractal analysis automatic to detect the malignancy of skin lesions [b7]. However, until now there is no comprehensive technique/approach using retinal images to provide disease risk prediction based on their complexity of characteristics (i.e., interaction between shapes, intensity, directionality and etc.).

We developed an automated disease detection system using retinal images. We first generate all possible risk factors from color images that may associated with diabetes retinopathy, stroke and/or other diseases. This includes some characteristics from the aspect of intensity changes, such as high order spectra, entropy and etc., and also from Gray Level Co-occurrence Matrix (or Haralick) and run-length matrix Texture Features. For instance, our previous study for retinal vessel patterns with neovascularisation detection has shown that there are number of significant of interactions among some high order spectra features and features related to the shape of vessels. Secondly, we stored all generated factors and applied penalized supervised logistic regression to reduce the dimension (or use random forest approach to extract important features). This procedure is used to generate potentially significant features associated with stroke and other diseases. Next we applied multi-model inference with Generalized Linear Models (MIGLM) to select the best model that generated all possible factors with their pairwise interactions. Finally we applied the Random Forest to assess its stroke classification performance. The advantage of using penalized supervised logistic regression and MIGLM are their interactive effects preserving properties. Random Forest approach is considerable a suitable method for non-linear classification in high-dimensional space [b8].

BRIEF SUMMARY

In one aspect disclosed herein, there is provided a method for diagnosing and/or predicting the presence, progression and/or treatment effect of a disease characterized by retinal pathological changes in a subject, comprising the steps of:
 (a) obtaining a retinal fundus image from the subject;
 (b) converting the image to a gray level image and/or extracting vessels from the image to obtain the gray level image and/or the vessel image;
 (c) performing one or at least two or more analyses on the gray level image and/or the vessel image, and generating one or more factors, wherein the one or at least two or more analyses are selected from the group consisting of
  fractal analysis,
  statistical texture analysis,
  high order spectra analysis,
  abnormal pattern analysis,
  and any combination thereof; and
 (d) comparing the one or more factors obtained from step (c) with those of a control, a change of the factors is an indication of the presence, progression and/or treatment effect of the disease in the subject.

In another aspect, there is provided a method for generating one or more factors associated with retinal image changes in a subject, comprising the steps of:
 (a) obtaining a retinal fundus image from the subject;
 (b) converting the image to a gray level image and/or extracting vessels from the image to obtain the gray level image and/or the vessel image; and
 (c) performing one or at least two or more analyses on the gray level image and/or the vessel image, and generating one or more factors, wherein the one or at least two or more analyses are selected from the group consisting of
  fractal analysis,
  statistical texture analysis,
  high order spectra analysis,
  abnormal pattern analysis,
  and any combination thereof.

In one embodiment of the methods disclosed herein, step (b) includes using mathematical morphological operations and/or dual tree complex wavelet transform technique.

In some embodiments, the methods disclosed herein comprise performing fractal analysis on the image and generating features associated with the fractal. In one embodiment, the fractal analysis may include using complex wavelet methods, preferably complex wavelet Leader multifractal analysis. In another embodiment, the fractal analysis may include using multifractal spectrum analysis. In one embodiment, the factor generated by the fractal analysis is selected from the group consisting of Sum Average, Cluster Shade, Hausdorff dimension, and any combination thereof.

In some embodiments, the statistical texture analysis may include using gray level co-occurrence matrix (GLCM) and/or run length matrix (RLM) to generate texture features including normalized Homogeneity, normalized Entropy, normalized Contrast, normalized $4^{th}$ moment and normalized Run percentage. In some embodiments, the higher order spectral (HOS) features obtained from the higher order spectral (HOS) analysis may include Entropy1 HOS features at degree of 100, Entropy2 HOS features at degree of 160, Entropy3 HOS features at degree of 40, Entropy3 HOS features at degree of 140 and 160; Entropy Phase HOS features at degree of 40, 140, 160 and 180; Entropy Magnitude HOS features at degree of 0, 20, 40, 60, 100, 120, 140, 160 and 180. In a preferred embodiment, the method disclosed herein comprises performing statistical texture analysis in combination with higher order spectral (HOS) analysis on the gray level image and generating features associated with the texture.

In other embodiments, the methods disclosed herein further include analyzing the blood vessels properties from the gray level image and/or the vessel image and generating a factor associated with the blood vessels properties. The factor associated with the blood vessels properties may be artery/vein ratio (AVR), where AVR=Central Retinal Artery Equivalent (CRAE)/Central Retinal Vein Equivalent (CRVE).

In other embodiments, the method disclosed herein comprises performing abnormal pattern analysis on the gray level image and/or the vessel image and generating features associated with the abnormal patterns. In one embodiment, the abnormal pattern analysis may include using a wavelet algorithm based on wavelet transform, preferably a dual tree complex wavelet transform and a wavelet-based Radon transform. In another embodiment, the abnormal pattern analysis may include using higher order spectral analysis in combination with a wavelet algorithm based on wavelet transform, preferably a dual tree complex wavelet transform and a wavelet-based Radon transform. In some embodiments, the abnormal patterns may include hemorrhages, exudates, new vessels, microaneurysm, proliferative vitreoretinopathy or any combination thereof. In a particular embodiment, the abnormal patterns are hemorrhages.

In some embodiments of the methods disclosed herein, the disease is selected from the group consisting of stroke, subclinical brain lesion, white matter lesion, dementia, hypertension, diabetes, cardiovascular diseases including coronary heart disease and cerebral vascular disease, glaucoma, prematurity, papilloedema, and common retina disease, such as macular hole, age-related macular degeneration. In one embodiment, the disease is stroke, and step (c) includes performing at least two of the four analyses on the gray level image and/or the vessel image, and generating one or more factors. In one embodiment, the disease is diabetes, and step (c) includes performing at least two of the four analyses on the gray level image and/or the vessel image, and generating one or more factors. In another embodiment, the disease is diabetes, and step (c) includes performing statistical texture analysis and abnormal pattern analysis on the gray level image and/or the vessel image, and generating one or more factors.

In a further embodiment, the methods disclosed herein may be used to grade the retinal pathological changes in a subject. In one embodiment, the retinal pathological changes are diabetic retinal pathological changes.

In another aspect disclosed herein, there is provided a device for diagnosing and/or predicting the presence, progression and/or treatment effect of a disease characterized by retinal pathological changes in a subject, comprising:

an image-capturing module for obtaining a retinal fundus image from the subject;

a conversion module for converting the image to a gray level image and/or extracting vessels from the image to obtain said gray level image and/or vessel image;

an analysis module comprising one or at least two or more submodules for performing analysis on the gray level image and/or vessel image and generating one or more factors, wherein the one or at least two or more submodules are selected from the group consisting of a fractal analysis submodule,
a statistical texture analysis submodule,
a high order spectra analysis submodule,
an abnormal pattern analysis submodule,
and any combination thereof; and optionally a comparison module for comparing the factors obtained from the analysis module with those of a control.

In one embodiment of the device disclosed herein, the conversion module is configured to carry out mathematical morphological operations and/or dual tree complex wavelet transform technique.

In some embodiments, the analysis module comprises a fractal analysis submodule for performing fractal analysis on the image and generating features associated with the fractal. In one embodiment, the fractal analysis submodule is configured to carry out complex wavelet methods, preferably complex wavelet Leader multifractal analysis. In another embodiment, the fractal analysis submodule is configured to carry out multifractal spectrum analysis. In one embodiment, the factor generated by the fractal analysis submodule is selected from the group consisting of Sum Average, Cluster Shade, Hausdorff dimension, and any combination thereof.

In some embodiments, the statistical texture analysis submodule is configured to carry out gray level co-occurrence matrix (GLCM) and/or run length matrix (RLM) to obtain texture features, including normalized Homogeneity, normalized Entropy, normalized Contrast, normalized $4^{th}$ moment and normalized Run percentage. In some embodiments, the higher order spectral (HOS) features generated by the high order spectra analysis submodule may include Entropy1 HOS features at degree of 100, Entropy2 HOS features at degree of 160, Entropy3 HOS features at degree of 40, Entropy3 HOS features at degree of 140 and 160; Entropy Phase HOS features at degree of 40, 140, 160 and 180; Entropy Magnitude HOS features at degree of 0, 20, 40, 60, 100, 120, 140, 160 and 180. In some embodiments, the analysis module comprises a statistical texture analysis submodule and/or a high order spectra analysis submodule for performing texture analysis on the gray level image and/or the vessel image and generating a factor associated with the texture. In a preferred embodiment, the statistical texture analysis submodule is used in combination with the high order spectra analysis submodule.

In other embodiments, the analysis module further comprises a blood vessel property analysis submodule for analyzing the blood vessels properties from the gray level image and/or the vessel image and generating a factor associated with the vessels properties. The factor associated with the vessels properties may be artery/vein ratio (AVR), where AVR=Central Retinal Artery Equivalent (CRAE)/Central Retinal Vein Equivalent (CRVE).

In other embodiments, the analysis module comprises an abnormal pattern analysis submodule for detecting the abnormal patterns from the gray level image and/or the vessel image and generating features associated with the abnormal patterns. In one embodiment, the abnormal pattern analysis submodule is configured to carry out a wavelet algorithm based on wavelet transform, preferably a dual tree complex wavelet transform and a wavelet-based Radon transform. In another embodiment, the abnormal pattern analysis submodule is configured to carry out higher order spectral analysis in combination with a wavelet algorithm based on wavelet transform, preferably a dual tree complex wavelet transform and a wavelet-based Radon transform. In some embodiments, the abnormal patterns may include hemorrhages, exudates, new vessels, microaneurysm, proliferative vitreoretinopathy or any combination thereof. In a particular embodiment, the abnormal patterns are hemorrhages.

In some embodiments of the device disclosed herein, the disease is selected from the group consisting of stroke, subclinical brain lesion, white matter lesion, dementia, hypertension, diabetes, cardiovascular diseases including coronary heart disease and cerebral vascular disease, glaucoma, prematurity, papilloedema, and common retina disease, such as macular hole, age-related macular degeneration. In one embodiment, the disease is stroke, and the analysis module comprises at least two of the four submodules. In one embodiment, the disease is diabetes, and the analysis module comprises at least two of the four submodules. In another embodiment, the disease is diabetes, and the analysis module comprises a statistical texture analysis submodule and an abnormal pattern analysis submodule.

In a further embodiment, the devices disclosed herein may be used to grade the retinal pathological changes in a subject. In one embodiment, the retinal pathological changes are diabetic retinal pathological changes.

In another aspect disclosed herein, there is provided a method for screening or grading diabetic retinopathy in a subject, the method comprising the steps of a) capturing retina images from the subject;
b) preprocessing the images to enhance the image contrast using mathematical morphological operations and wavelet transform;
c) locating optic disc and macula in the preprocessed images by morphological analysis;
d) detecting and analyzing abnormal patterns related to diabetic retinopathy in the preprocessed image, wherein the abnormal patterns are analyzed using wavelet algorithm; and
e) integrating the detection results and grading the severity of diabetic retinopathy based on the integrated results.

In another aspect disclosed herein, there is provided a system for screening or grading diabetic retinopathy in a subject, comprising a) a first module for capturing retina images from the subject;
b) a second module for receiving and preprocessing the images to enhance the image contrast using mathematical morphological operations and wavelet transform;
c) a third module for locating optic disc and macula in the preprocessed images by morphological analysis;
d) a fourth module for detecting and analyzing abnormal patterns related to the retinopathy in the preprocessed image, which optionally comprises multiple units to detect different abnormal patterns, wherein the abnormal patterns are analyzed using wavelet algorithm; and
e) a fifth module for integrating the analyzed results and grading the retinopathy based on the integrated results.

Further scope of the applicability of the present invention will become apparent from the detailed description and drawings provided below. It should be understood, however, that the following detailed description and examples, while indicating preferred embodiments of the invention, are given by way of illustration only, since various changes and modifications within the spirit and scope of the invention will become apparent to those skilled in the art from the following detailed description and are defined in the claims appended below.

BRIEF DESCRIPTIONS OF THE SEVERAL VIEWS OF THE DRAWINGS

FIG. 1: Block Diagram of Overall System.

Figure 2:
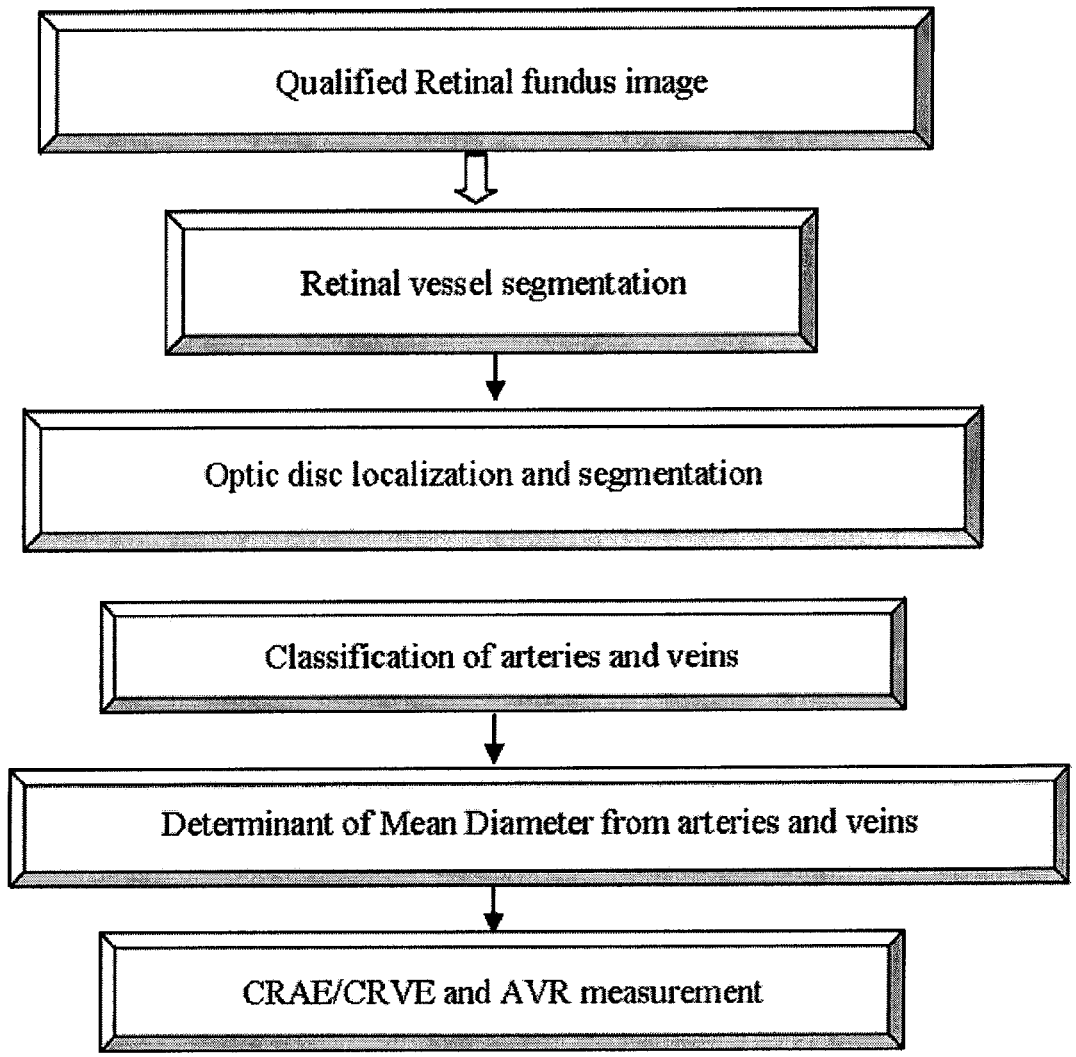

FIG. 2: The flowchart of the overall scheme for AVR measurement.

Figure 3:
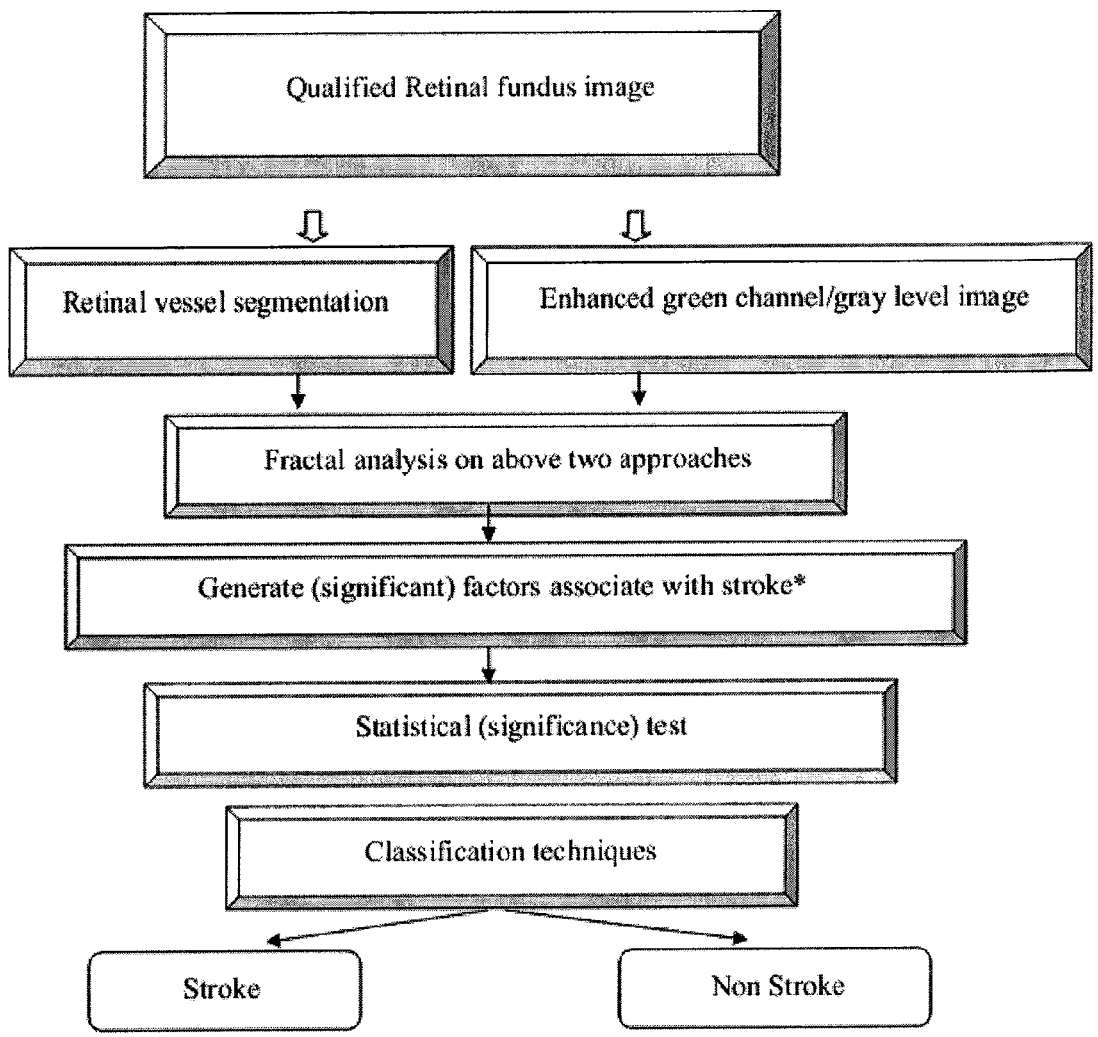

FIG. 3: The flowchart of the overall scheme for blood vessels related features using fractal analysis (Complement of stroke related features other than AVR measurement).

Figure 4:
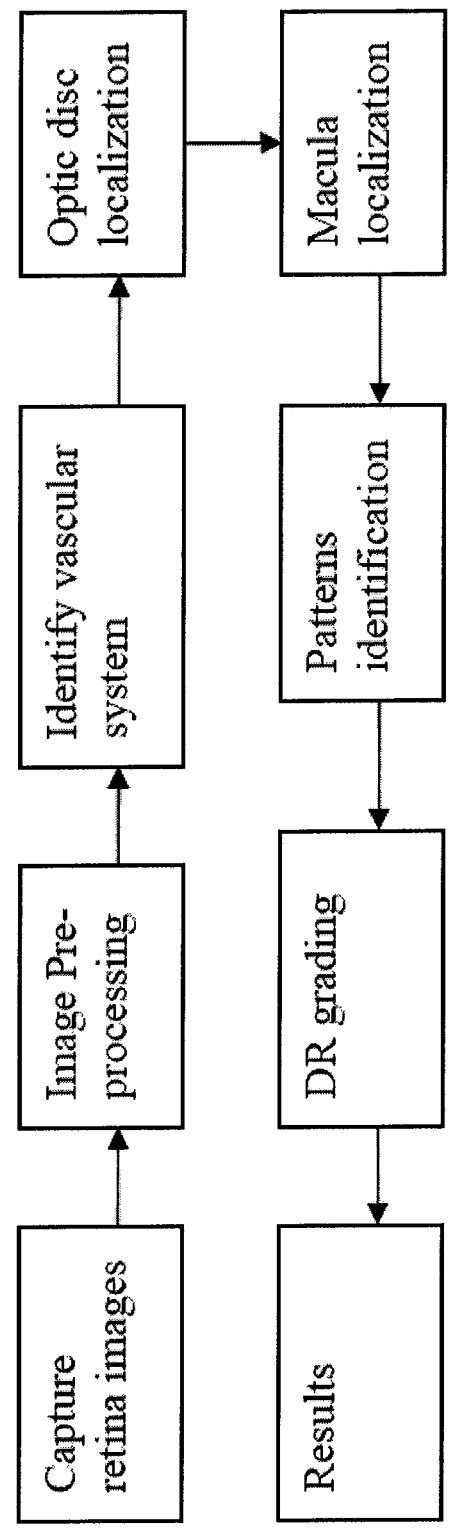

FIG. 4: a scheme for screening or grading diabetic retinopathy.

Figure 5:
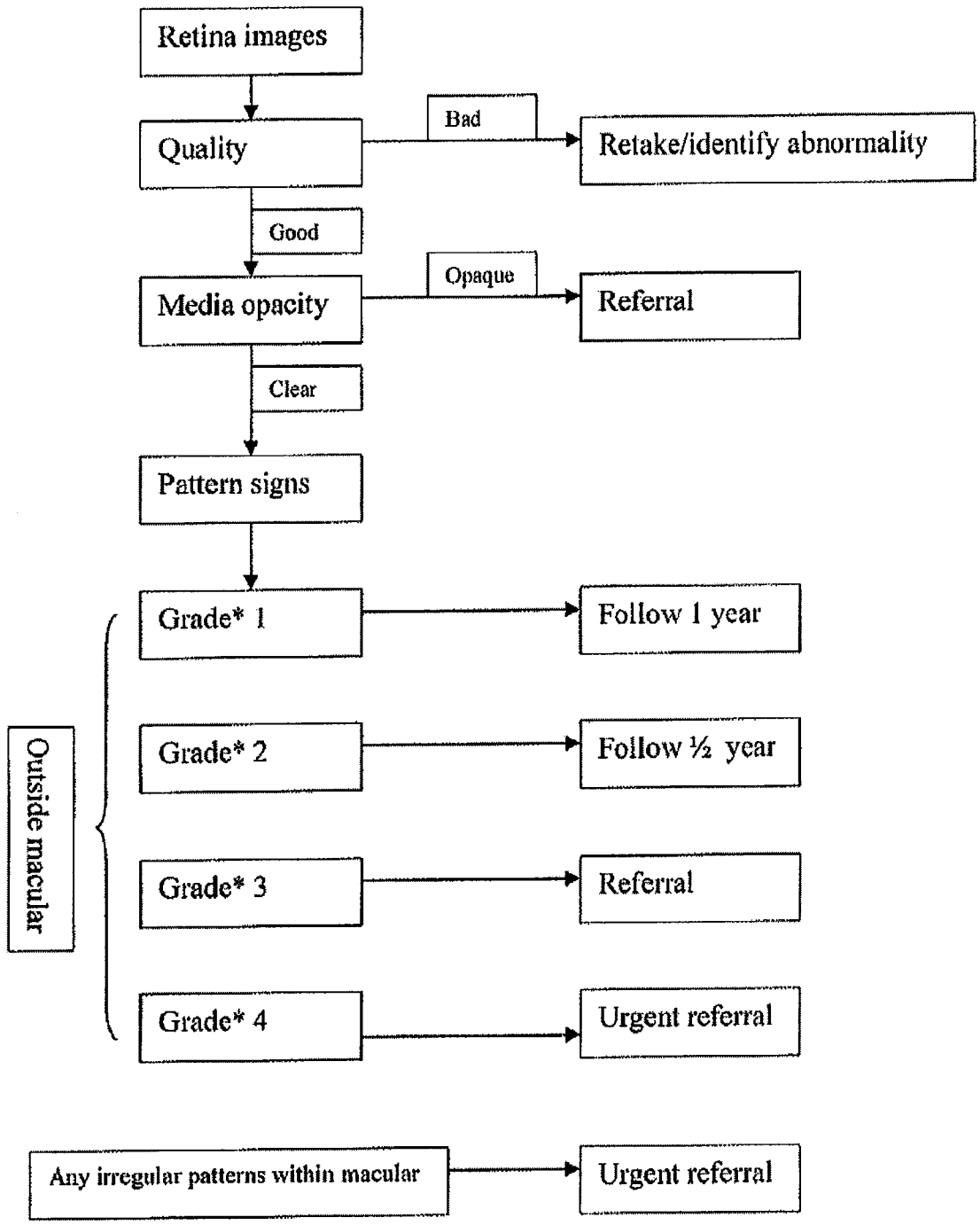

FIG. 5: an exemplified procedure for screening or grading diabetic retinopathy.

Figure 6:
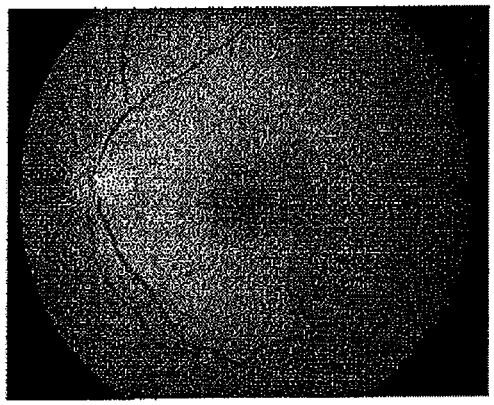
Figure 6:
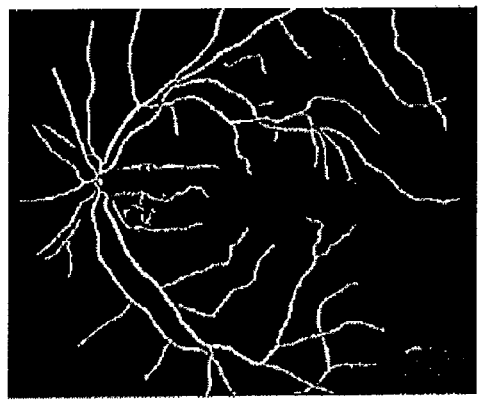
Figure 6:
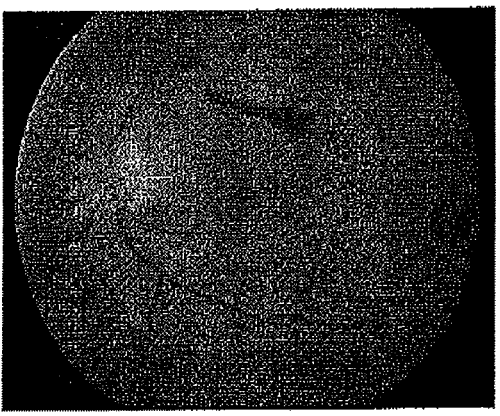
Figure 6:
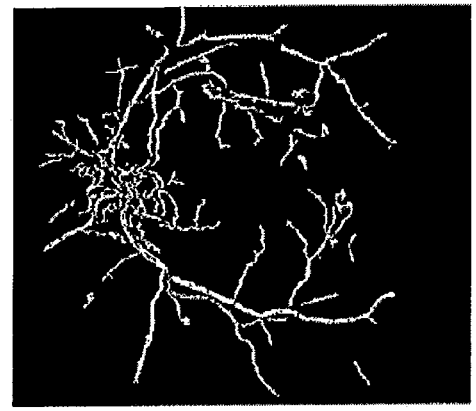

FIG. 6: normal retina image and retina image with new vessel detected by a system of the application. A, normal retina image; B, vessel segmentation of the normal retina image; C, retina image with new vessel on optic disc; and D, curl small vessels on optic disc.

Figure 7A:
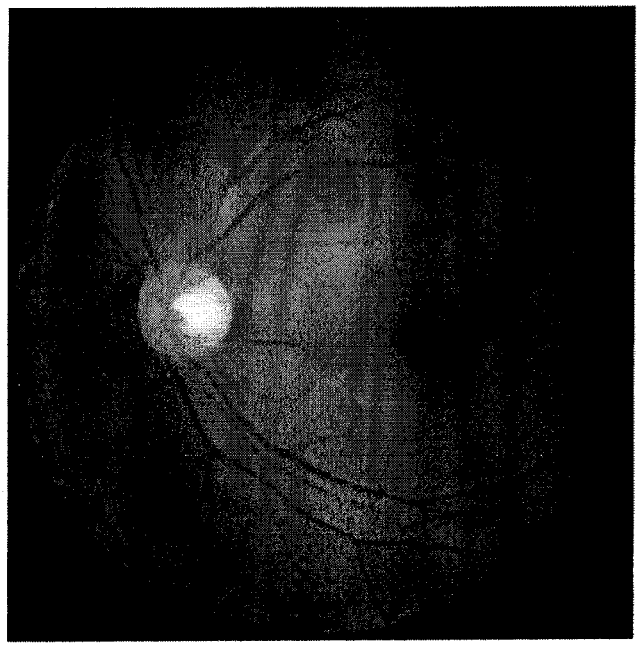
Figure 7B:
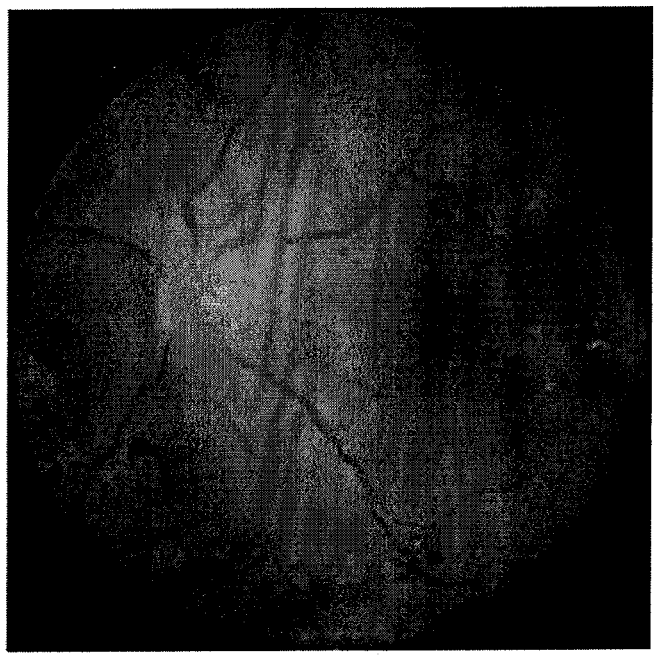
Figure 7C:
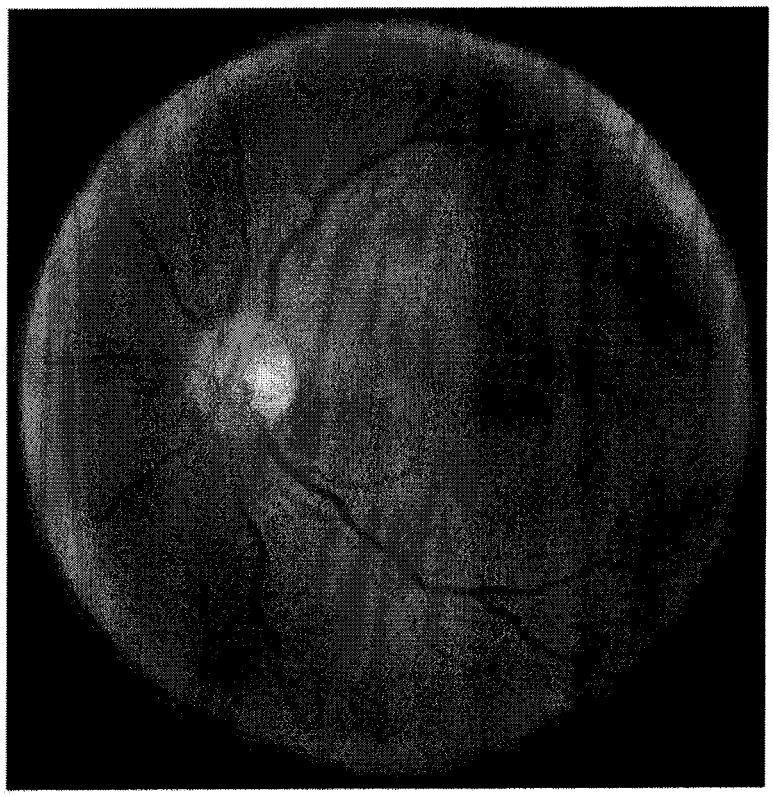

FIGS. 7a-7c: Sample color retina images of vessel tortuosity level.

Figure 8:
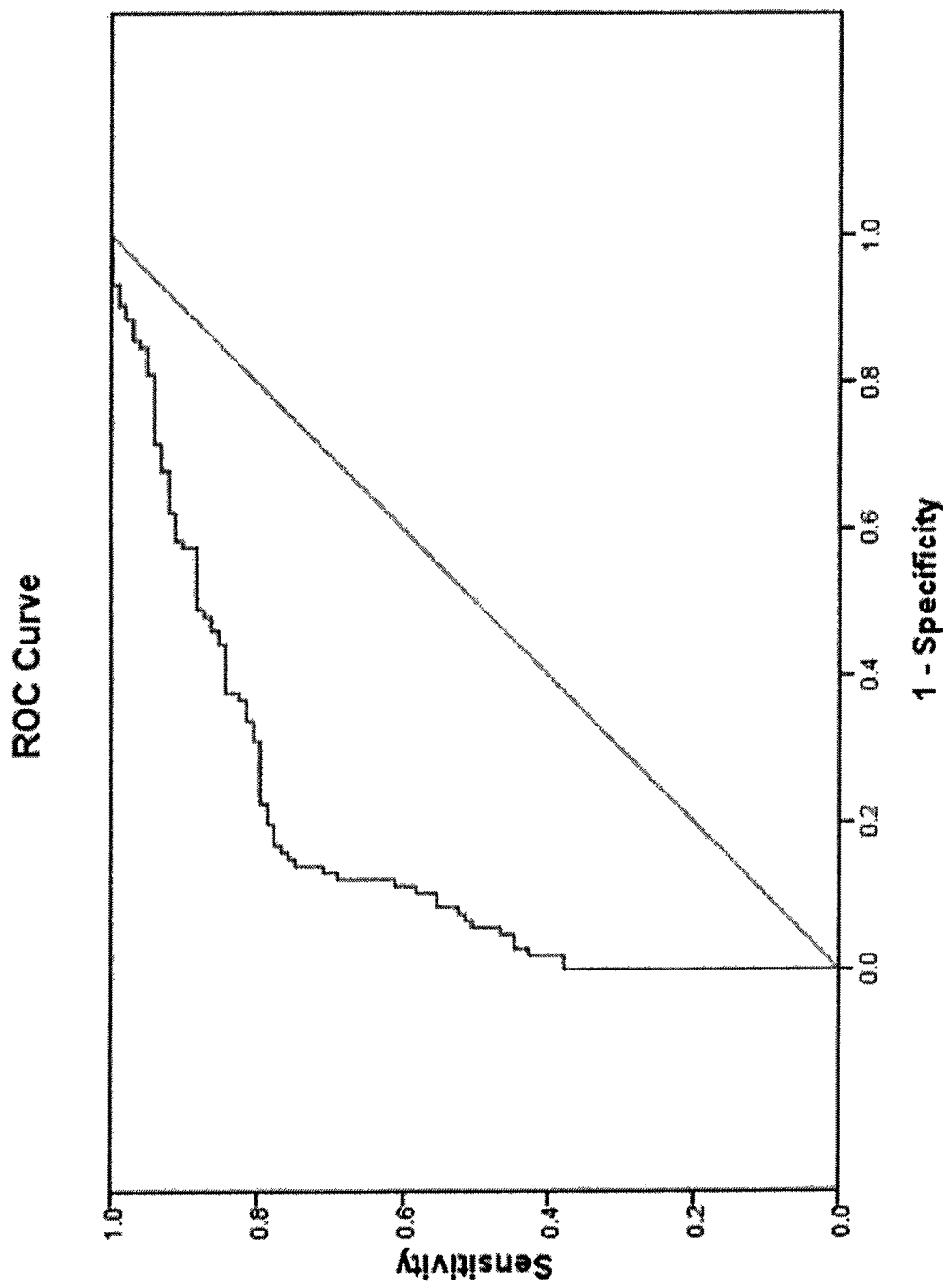

FIG. 8: Receiver operating characteristic (ROC) analysis of the risk models.

Figure 9:
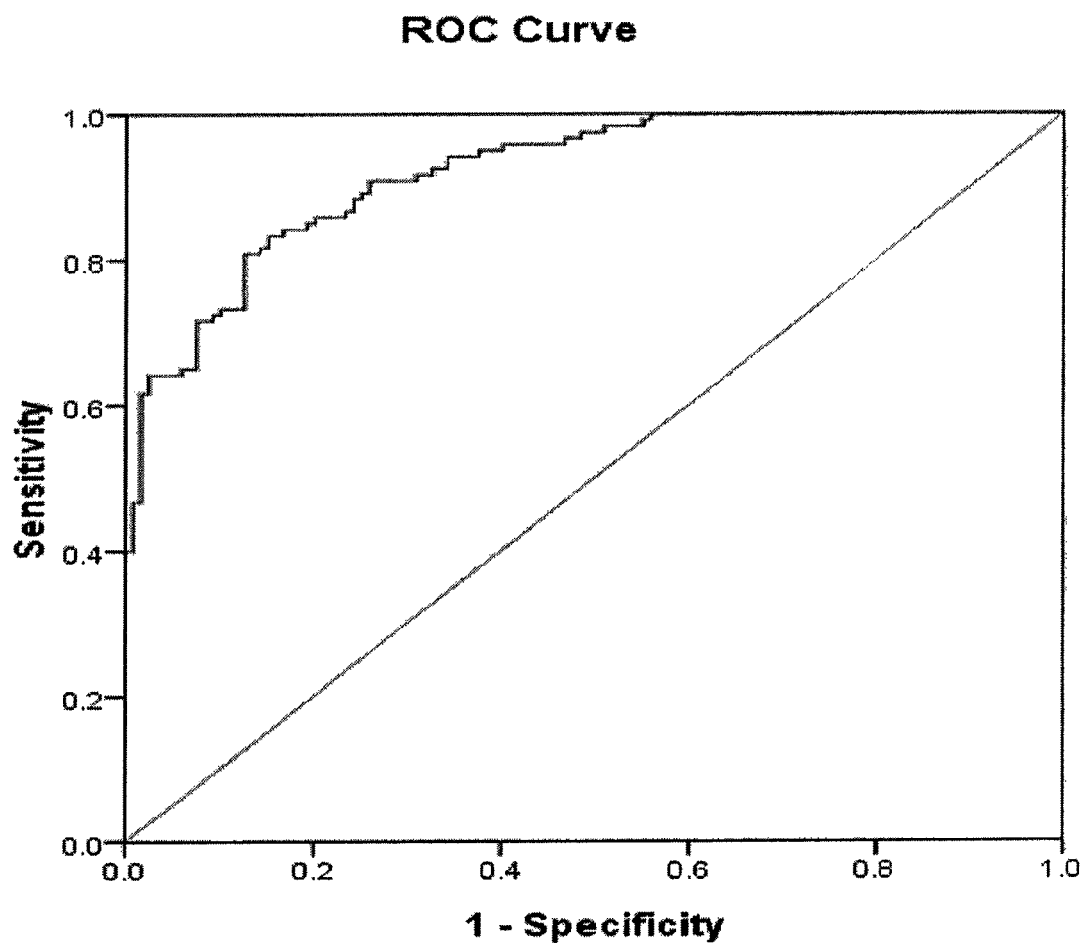

FIG. 9: AUC for the automatic detection.

DETAILED DESCRIPTION

Definitions

As used herein, the term "comprising" means "including". Variations of the word "comprising", such as "comprise" and "comprises", have correspondingly varied meanings. Thus, for example, a module "comprising" a unit may consist exclusively of that unit or may include one or more additional units.

As used in this application, the singular form "a", "an" and "the" include plural references unless the context clearly dictates otherwise. In particular, where the indefinite article is used, the specification is to be understood as contemplating plurality as well as singularity, unless the context requires otherwise.

As used herein, the terms "subject" and "patient" are used interchangeably, referring to a mammal including a non-primate (e.g., a camel, donkey, zebra, cow, pig, horse, cat, dog, rat, and mouse) and a primate (e.g., a monkey, chimpanzee, and a human). In certain embodiments, the subject or patient suffers or is susceptible to suffer from a disease characterized by a change of retinal pathology.

Reference throughout this specification to "one embodiment", or "an embodiment", or "in another embodiment", or "some embodiments", or "other embodiments" means that a particular referent feature, structure, or characteristic described in connection with the embodiment(s) is included in at least one embodiment. Thus, the appearance of the phrases "in one embodiment", or "in an embodiment", or "in another embodiment", or "in some embodiments" or "other embodiments" in various places throughout this specification are not necessarily all referring to the same embodiment(s). Furthermore, the particular features, structures, or characteristics may be combined in any suitable manner in one or more embodiments.

The term "abnormal patterns" refers to the image signals which are not present in normal retinal image and are associated with diabetic retinopathy. Such abnormal patterns includes, but not limited to hemorrhage, exudates, new vessels, microaneurysm and proliferative vitreoretinopathy.

The following descriptions further illustrate the above one or more embodiments in detail and any section of the descriptions can be solely used and combined in any suitable manner in one or more embodiments.

In one aspect disclosed herein, there is provided a method for diagnosing and/or predicting the presence, progression and/or treatment effect of a disease characterized by retinal pathological changes in a subject, comprising the steps of:

(a) obtaining a retinal fundus image from the subject;

(b) converting the image to a gray level image and/or extracting vessels from the image to obtain the gray level image and/or the vessel image;

(c) performing one or at least two or more analyses on the gray level image and/or the vessel image, and generating one or more factors, wherein the one or at least two or more analyses are selected from the group consisting of fractal analysis, statistical texture analysis, high order spectra analysis, abnormal pattern analysis, and any combination thereof; and (d) comparing the one or more factors obtained from step (c) with those of a control, a change of the factors is an indication of the presence, progression and/or treatment effect of the disease in the subject.

In another aspect, there is provided a method for generating one or more factors associated with retinal image changes in a subject, comprising the steps of:

(a) obtaining a retinal fundus image from the subject;

(b) converting the image to a gray level image and/or extracting vessels from the image to obtain the gray level image and/or the vessel image; and (c) performing one or at least two or more analyses on the gray level image and/or the vessel image, and generating one or more factors, wherein the one or at least two or more analyses are selected from the group consisting of fractal analysis, statistical texture analysis, high order spectra analysis, abnormal pattern analysis, and any combination thereof.

In one embodiment of the methods disclosed herein, step (b) includes using mathematical morphological operations and/or dual tree complex wavelet transform technique.

In some embodiments, the methods disclosed herein comprise performing fractal analysis on the image and generating features associated with the fractal. In one embodiment, the fractal analysis may include using complex wavelet methods, preferably complex wavelet Leader multifractal analysis. In another embodiment, the fractal analysis may include using multifractal spectrum analysis. In one embodiment, the factor generated by the fractal analysis is selected from the group consisting of Sum Average, Cluster Shade, Hausdorff dimension, and any combination thereof.

In some embodiments, the statistical texture analysis may include using gray level co-occurrence matrix (GLCM) and/or run length matrix (RLM) to generate texture features including normalized Homogeneity, normalized Entropy, normalized Contrast, normalized $4^{th}$ moment and normalized Run percentage. In some embodiments, the higher order spectral (HOS) features obtained from the higher order spectral (HOS) analysis may include Entropy1 HOS features at degree of 100, Entropy2 HOS features at degree of 160, Entropy3 HOS features at degree of 40, Entropy3 HOS features at degree of 140 and 160; Entropy Phase HOS features at degree of 40, 140, 160 and 180; Entropy Magnitude HOS features at degree of 0, 20, 40, 60, 100, 120, 140, 160 and 180.

In a preferred embodiments, the method disclosed herein comprises performing statistical texture analysis in combination with higher order spectral (HOS) analysis on the gray level image and generating features associated with the texture.

In other embodiments, the methods disclosed herein further include analyzing the blood vessels properties from the gray level image and/or the vessel image and generating a factor associated with the blood vessels properties. The factor associated with the blood vessels properties may be artery/vein ratio (AVR), where AVR=Central Retinal Artery Equivalent (CRAE)/Central Retinal Vein Equivalent (CRVE).

In other embodiments, the method disclosed herein comprises performing abnormal pattern analysis on the gray level image and/or the vessel image and generating features associated with the abnormal patterns. In one embodiment, the abnormal pattern analysis may include using a wavelet algorithm based on wavelet transform, preferably a dual tree complex wavelet transform and a wavelet-based Radon transform. In another embodiment, the abnormal pattern analysis may include using higher order spectral analysis in combination with a wavelet algorithm based on wavelet transform, preferably a dual tree complex wavelet transform and a wavelet-based Radon transform. In some embodiments, the abnormal patterns may include hemorrhages, exudates, new vessels, microaneurysm, proliferative vitreoretinopathy or any combination thereof. In a particular embodiment, the abnormal patterns are hemorrhages.

In some embodiments of the methods disclosed herein, the disease is selected from the group consisting of stroke, subclinical brain lesion, white matter lesion, dementia, hypertension, diabetes, cardiovascular diseases including coronary heart disease and cerebral vascular disease, glaucoma, prematurity, papilloedema, and common retina disease, such as macular hole, age-related macular degeneration. In one embodiment, the disease is stroke, and step (c) includes performing at least two of the four analyses on the gray level image and/or the vessel image, and generating one or more factors. In one embodiment, the disease is diabetes, and step (c) includes performing at least two of the four analyses on the gray level image and/or the vessel image, and generating one or more factors. In another embodiment, the disease is diabetes, and step (c) includes performing statistical texture analysis and abnormal pattern analysis on the gray level image and/or the vessel image, and generating one or more factors.

In a further embodiment, the methods disclosed herein may be used to grade the retinal pathological changes in a subject. In one embodiment, the retinal pathological changes are diabetic retinal pathological changes.

In another aspect disclosed herein, there is provided a device for diagnosing and/or predicting the presence, progression and/or treatment effect of a disease characterized by retinal pathological changes in a subject, comprising:

an image-capturing module for obtaining a retinal fundus image from the subject;

a conversion module for converting the image to a gray level image and/or extracting vessels from the image to obtain said gray level image and/or vessel image;

an analysis module comprising one or at least two or more submodules for performing analysis on the gray level image and/or vessel image and generating one or more factors, wherein the one or at least two or more submodules are selected from the group consisting of a fractal analysis submodule,
a statistical texture analysis submodule,
a high order spectra analysis submodule,
an abnormal pattern analysis submodule,
and any combination thereof; and
optionally a comparison module for comparing the factors obtained from the analysis module with those of a control.

In one embodiment of the device disclosed herein, the conversion module is configured to carry out mathematical morphological operations and/or dual tree complex wavelet transform technique.

In some embodiments, the analysis module comprises a fractal analysis submodule for performing fractal analysis on the image and generating features associated with the fractal. In one embodiment, the fractal analysis submodule is configured to carry out complex wavelet methods, preferably complex wavelet Leader multifractal analysis. In another embodiment, the fractal analysis submodule is configured to carry out multifractal spectrum analysis. In one embodiment, the factor generated by the fractal analysis submodule is selected from the group consisting of Sum Average, Cluster Shade, Hausdorff dimension, and any combination thereof.

In some embodiments, the statistical texture analysis submodule is configured to carry out gray level co-occurrence matrix (GLCM) and/or run length matrix (RLM) to obtain texture features, including normalized Homogeneity, normalized Entropy, normalized Contrast, normalized $4^{th}$ moment and normalized Run percentage. In some embodiments, the higher order spectral (HOS) features generated by the high order spectra analysis submodule may include Entropy1 HOS features at degree of 100, Entropy2 HOS features at degree of 160, Entropy3 HOS features at degree of 40, Entropy3 HOS features at degree of 140 and 160; Entropy Phase HOS features at degree of 40, 140, 160 and 180; Entropy Magnitude HOS features at degree of 0, 20, 40, 60, 100, 120, 140, 160 and 180. In some embodiments, the analysis module comprises a statistical texture analysis submodule and/or a high order spectra analysis submodule for performing texture analysis on the gray level image and/or the vessel image and generating a factor associated with the texture. In a preferred embodiment, the statistical texture analysis submodule is used in combination with the high order spectra analysis submodule.

In other embodiments, the analysis module further comprises a blood vessel property analysis submodule for analyzing the blood vessels properties from the gray level image and/or the vessel image and generating a factor associated with the vessels properties. The factor associated with the vessels properties may be artery/vein ratio (AVR), where AVR=Central Retinal Artery Equivalent (CRAE)/Central Retinal Vein Equivalent (CRVE).

In other embodiments, the analysis module comprises an abnormal pattern analysis submodule for detecting the abnormal patterns from the gray level image and/or the vessel image and generating features associated with the abnormal patterns. In one embodiment, the abnormal pattern analysis submodule is configured to carry out a wavelet algorithm based on wavelet transform, preferably a dual tree complex wavelet transform and a wavelet-based Radon transform. In another embodiment, the abnormal pattern analysis submodule is configured to carry out higher order spectral analysis in combination with a wavelet algorithm based on wavelet transform, preferably a dual tree complex wavelet transform and a wavelet-based Radon transform. In some embodiments, the abnormal patterns may include hemorrhages, exudates, new vessels, microaneurysm, proliferative vitreoretinopathy or any combination thereof. In a particular embodiment, the abnormal patterns are hemorrhages.

In some embodiments of the device disclosed herein, the disease is selected from the group consisting of stroke, subclinical brain lesion, white matter lesion, dementia, hypertension, diabetes, cardiovascular diseases including coronary heart disease and cerebral vascular disease, glaucoma, prematurity, papilloedema, and common retina disease, such as macular hole, age-related macular degeneration. In one embodiment, the disease is stroke, and the analysis module comprises at least two of the four submodules. In one embodiment, the disease is diabetes, and the analysis module comprises at least two of the four submodules. In another embodiment, the disease is diabetes, and the analysis module comprises a statistical texture analysis submodule and an abnormal pattern analysis submodule.

In a further embodiment, the devices disclosed herein may be used to grade the retinal pathological changes in a subject. In one embodiment, the retinal pathological changes are diabetic retinal pathological changes.

In some embodiments of the methods or devices disclosed herein, the Hausdorff dimension is associated with or statistically significant associated with normalized diameter of arterioles (NadjustedCRAE), Vasymmetry by NadjustedCRAE, mean venules, Vasymmetry and hemorrhage with adjusted diameter of arterioles, and/or the Hausdorff dimension is associated with atrial fibrillation, hypertension, hemorrhage, diabetes, vessel tortuosity, and arteriole-venule nicking In some embodiments of the methods or devices disclosed herein, the fractal related texture features Sum Average and Cluster Shade are (statistically significant) associated with normalized diameter of arterioles (NadjustedCRAE), Vasymmetry by NadjustedCRAE, mean venules Vasymmetry and hemorrhage with adjusted diameter of arterioles.

In some embodiments of the methods or devices disclosed herein, the texture feature of normalized Homogeneity is (statistically significant) associated with stroke related features: Vasymmetry by NadjustedCRAE, NadjustedCRAE, mean venules Vasymmetry, hemorrhage with adjusted diameter of arterioles and vasymmetry with tortuosity.

In some embodiments of the methods or devices disclosed herein, the texture feature of normalized Entropy is (statistically significant) associated with stroke related features: Vasymmetry by NadjustedCRAE, NadjustedCRAE, mean venules Vasymmetry, hemorrhage with adjusted diameter of arterioles and Vasymmetry with tortuosity.

In some embodiments of the methods or devices disclosed herein, the texture feature of normalized Contrast is (statistically significant) associated with stroke related features: Vasymmetry by NadjustedCRAE, NadjustedCRAE, mean venules Vasymmetry, hemorrhage with adjusted diameter of arterioles and Vasymmetry with tortuosity.

In some embodiments of the methods or devices disclosed herein, the texture feature of normalized $4^{th}$ moment is (statistically significant) associated with stroke related features: Vasymmetry by NadjustedCRAE, NadjustedCRAE, mean venules Vasymmetry, hemorrhage with adjusted diameter of arterioles and Vasymmetry with tortuosity.

In some embodiments of the methods or devices disclosed herein, the texture feature of normalized Run percentage is (statistically significant) associated with stroke related features: Vasymmetry by NadjustedCRAE, NadjustedCRAE, mean venules Vasymmetry, hemorrhage with adjusted diameter of arterioles and Vasymmetry with tortuosity.

In some embodiments of the methods or devices disclosed herein, the texture feature of normalized Entropy is (large value of Odd ratio) associated with stroke related features: nipping.

In some embodiments of the methods or devices disclosed herein, the HOS feature of Entropy1 at degree of 100 is (statistically significant) associated with stroke related features: NadjustedCRAE; and/or the HOS feature of Entropy2 at degree of 160 is (statistically significant) associated with stroke related features: hemorrhage with adjusted diameter of arterioles; and/or the HOS feature of Entropy3 at degree of 160 is (statistically significant) associated with stroke related features: Vasymmetry by NadjustedCRAE and NadjustedCRAE alone.

In some embodiments of the methods or devices disclosed herein, the HOS feature of Entropy Phase at degree of 140 is (statistically significant) associated with stroke related features: Vasymmetry by NadjustedCRAE; and/or the HOS feature of Entropy Phase at degree of 160 is (statistically significant) associated with stroke related features: NadjustedCRAE; and/or the HOS feature of Entropy Phase at degree of 180 is (statistically significant) associated with stroke related features: NadjustedCRAE alone and Vasymmetry by NadjustedCRAE.

In some embodiments of the methods or devices disclosed herein, the HOS feature of Entropy Magnitude at degree of 0 is (statistically significant) associated with stroke related features: vasymmetry with tortuosity; and/or the HOS feature of Entropy Magnitude at degree of 20 is (statistically significant) associated with stroke related features: vasymmetry with tortuosity; and/or the HOS feature of Entropy Magnitude at degree of 40 is (statistically significant) associated with stroke related features: NadjustedCRAE; and/or the HOS feature of Entropy Magnitude at degree of 60 is highly (statistically significant) associated with stroke related features: NadjustedCRAE; and/or the HOS feature of Entropy Magnitude at degree of 100 is (statistically significant) associated with stroke related features: vasymmetry with tortuosity, Vasymmetry by NadjustedCRAE and mean venules Vasymmetry; and/or the HOS feature of Entropy Magnitude at degree of 120 is highly (statistically significant) associated with stroke related features: NadjustedCRAE alone and hemorrhage with adjusted diameter of arterioles; and/or the HOS feature of Entropy Magnitude at degree of 140 is (statistically significant) associated with stroke related features: NadjustedCRAE alone and Vasymmetry by NadjustedCRAE; and/or the HOS feature of Entropy Magnitude at degree of 160 is highly (statistically significant) associated with stroke related features: NadjustedCRAE alone and vasymmetry with tortuosity; and/or the HOS feature of Entropy Magnitude at degree of 180 is highly (statistically significant) associated with stroke related features: Vasymmetry by NadjustedCRAE and Vasymmetry with tortuosity.

In some embodiments of the methods or devices disclosed herein, the HOS feature of Entropy Phase at degree of 180 is (statistically significant) associated with stroke related features: AF; and/or other HOS features that highly associated with stroke related feature of hypertension are: Entropy Magnitude at degree of 40, 60, 100, 120 and 140; and/or HOS features that are associated with stroke related features of diabetes are: Entropy3 at degree of 40 and 140, Entropy Phase at degree of 140, Entropy Magnitude at degree of 100 and 120 and/or HOS features associated with stroke related features of hemorrhage are: Entropy1 at degree of 0 and 160, and Entropy Magnitude at degree of 120 and/or HOS features that are associated with stroke related features of tortuosity0_1 are: Entropy1 at degree of 0, Entropy Magnitude at degree of 40 and 140.

In another aspect of the present application, it is directed to a system for screening or grading diabetic retinopathy in a subject, comprising a) a first module for capturing retina images from the subject;

b) a second module for receiving and preprocessing the images to enhance the image contrast using mathematical morphological operations and wavelet transform;

c) a third module for locating optic disc and macula in the preprocessed images by morphological analysis; and d) a fourth module for detecting and analyzing abnormal patterns related to the retinopathy in the preprocessed image, which optionally comprises multiple units to detect different abnormal patterns, wherein the abnormal patterns are analyzed using wavelet algorithm; and e) a fifth module for integrating the analyzed results and grading the retinopathy based on the integrated results.

The first module can be any imaging unit suitable for capturing retina images, which is preferably integrated to other modules. In an embodiment, the first module is digital fundus camera.

In an embodiment, the second module for preprocessing is configured to detect and reduce non-uniform illumination of the captured images, and enhance the image contrast using mathematical morphological operations and wavelet transform.

In a preferred embodiment, the second module is configured to detect and reduce non-uniform illumination of the captured images using the decorrelation stretching method with hybrid median filtering, top-hat, bottom-hat, and morphological enhancement operators for grey level.

In another preferred embodiment, the second module is configured to enhance the image contrast using mathematical morphological operations and dual tree complex wavelet transform (DTCWT).

In an embodiment, the third module locating optic disc and macula conducts a morphological analysis which comprises using dilation and erode preprocessed image with structure element on disk shape for filtering non-circular shape like spots.

In a preferred embodiment, the wavelet algorithm conducted by the fourth module is an algorithm based on wavelet transform. More preferably, the wavelet algorithm is selected from dual tree complex wavelet transform and a wavelet-based Radon transform. Most preferably, the fourth module is configured to conduct higher order spectral analysis which is combined with the wavelet algorithm.

In an embodiment, the system for screening or grading diabetic retinopathy in a subject further comprises a sixth module to extract and remove vessels prior to the detection of abnormal patterns.

Preferably, the sixth module is configured to identify and extract the vessels using vascular-based techniques selected from mathematical morphological operations with dual tree complex wavelet transformation (DTCWT) methodology, morphological filters, matched filters, and combinations thereof.

In another embodiment, the system for screening or grading diabetic retinopathy in a subject further comprises a seventh module for analyzing the texture in the preprocessed image in order to detect the abnormal patterns accurately.

In a preferred embodiment, the seventh module is configured to analyze the texture using statistical texture analysis techniques and higher order spectral analysis. More preferably, the statistical texture analysis techniques can be selected from a gray level co-occurrence matrix (GLCM) approach and run length matrix (RLM) approach.

In another preferred embodiment, the seventh module is configured to analyze the texture using a wavelet transform in combination with higher order spectral analysis. More preferably, the wavelet transform is wavelet-based Radon transform, and the higher order spectral features is 3rd order spectral analysis.

For the purpose of convenience, multiple modules can be integrated together for screening, diagnosing or grading diabetic retinopathy.

In another aspect of the present application, it is directed to a method for screening or grading retinopathy in a subject, comprising the following steps:

a) capturing retina images from the subject;

b) preprocessing the images to enhance the image contrast using mathematical morphological operations and wavelet transform;

c) locating optic disc and macula in the preprocessed images by morphological analysis; and d) detecting and analyzing abnormal patterns related to retinopathy in the preprocessed image, wherein the abnormal patterns are analyzed using wavelet algorithm; and e) integrating the detection results and grading the severity of retinopathy based on the integrated results.

In one embodiment, pre-processing of the captured image includes image clarity assessment, automatic assessment of imported image and enhancement of the qualified image contrast using wavelet transform analysis. In a preferred embodiment, the image clarity assessment includes detecting non-uniform illumination and reducing it. In a more preferred embodiment, reducing non-uniform illumination of the images is based on the decorrelation stretching method with hybrid median filtering, top-hat, bottom-hat, and morphological enhancement operators. Preferably, the image enhancement included within the step of pre-processing is conducted by mathematical morphological operations and wavelet transform to denoise and enhance the contrast at same time.

Advantageously, in a preferable example, the step of preprocessing of the captured image comprises:

i) detecting and reducing non-uniform illumination using retinex related technique for colored original image and gradient field with histogram equalization for grey level;

ii) assessing the captured images quality automatically based on clarity and field definition (see, Fleming, A. D., et al., Automated assessment of diabetic retinal image quality based on clarity and field definition. Invest Ophthalmol Vis Sci, 2006. 47(3): p. 1120-5); and iii) enhancing the qualified image contrast with mathematical morphological operations and dual tree complex wavelet transform (DTCWT).

In an embodiment, the location of optic disc can be based on known processes in the art which can distinguish between the retinal anatomical structures and the lesions. For example, Osareh, A., *Automated Identification of Diabetic Retinal Exudates and the Optic Disc*. PhD thesis. Department of Computer Science, University of Bristol, 2004 described the identification of optic disc based on its compactness feature: Compactness=(region border length)$^2$/area, wherein a boundary-tracing algorithm (see, Sonka, M., V. Hlavac, and R. Boyle, Image processing, analysis, and machine vision. 2nd ed. 1999, PWS Pub) can be employed to obtain the region border length. Alternatively, roundness detection with Hough circle method, geometrical structured (ellipse location) method or highest intensity region detection can be employed to detect and locate the optic disc in retina images.

In a preferred embodiment, locating the optic disc is carried out by morphological analysis which preferably comprises using dilation and erode preprocessed image with structure element on disk shape for filtering non-circular shape like spots.

In certain embodiments, the macular detection is based on similar means to those for detecting optic disc, excepting for reversing the background color (grey level) and then applying the constant distance (2.5 diameters) from OD to find darkest region, as the macular usually appears as a darkened region, and at a distance of approximately 2.5 times the optic disc diameter from the centre of the optic disc. It is known in the art that localization of macular contributes to early detection of lesions that threaten visual acuity and increase accuracy of lesion detection.

In one embodiment, the system or method for screening or grading retinopathy further comprises a module or a step of extracting and removing vessels prior to the detection of abnormal patterns so as to facilitate the accuracy of abnormal pattern lesions detection. The imaging of vessels can take place by means of optical imaging technique with optical-electronic image conversion, or by means of electronic image generating technique, e.g., scanning of photographic vessel images. Furthermore, dilatation measurements of vessels in the back of the eye can be based on the use of optical, precision measurement techniques in an ophthalmoscopic image, the use of precision optical measurement techniques and densitometry of the photographic negative or based on photoelectric measurement methods. Other devices or methods for identifying vessels are known in the art (see, for example, Suzuki, Y. Surv. Ophthalmol. 1995, May 39 Suppl. 1: 57-65; Schack et al. Mustererkennung 1994, Springer-Pub., 475-481; DE 3,839,272; U.S. Pat. No. 5,031,632; and U.S. Pat. No. 6,621,917).

Alternatively or additionally, examples of the vascular-based techniques can include, for example, mathematical morphological operations with dual tree complex wavelet transformation (DTCWT) methodology, morphological filters, matched filters, and combinations thereof.

In another preferred embodiment, the system or method further comprises a module or a step of analyzing the texture in the retina image in order to detect the abnormal patterns including HE and exudates accurately. Texture can be described as an attribute representing the spatial arrangement of the gray levels of the pixels in a region of a digital image. In texture analysis, its tasks are to carry out classification, segmentation, and synthesis. For example, statistical geometrical features and tree-structured wavelet transform can be used for texture analysis and classification. (see, for example, Chen, Y. Q., M. S, Nixon, and D. W. Thomas, Texture Classification Using. Image Processing, 1994: p. 446-450 1050; and Chang, T. and C. C. J. Kuo, Texture analysis and classification with tree-structured wavelet transform. Ieee Transactions on Image Processing, 1993. 2(4): p. 429-441).

In another preferred embodiment, approaches for analyzing texture can include, but not limited to statistical texture analysis techniques, structural texture analysis techniques, model-based texture analysis techniques, and transform-based texture analysis techniques.

Specifically, examples of statistical texture analysis techniques can include, but not limited to a gray level co-occurrence matrix (GLCM) approach which is based on the use of second-order statistics of the grayscale image histograms, and run length matrix (RLM) approach which encompasses higher-order statistics of the gray level histogram. Example of the structural texture analysis include using different shapes of structuring elements and conceiving real textures as distorted versions of ideal textures (see, for example, Indahl, U. G. and T. Naes, *Evaluation of alternative spectral feature extraction methods of textural images for multivariate modeling.* Journal of Chemometrics, 1998. 12(4): p. 261-278).

Example of model-based texture analysis techniques include autoregressive (AR) models, Markov random fields (MRF) (see, Cross, G. R. and A. K. Jain, *Markov Random Field Texture Models. Ieee Transactions on Pattern Analysis and Machine Intelligence,* 1983. 5(1): p. 25-39), and fractal models. Transform-based texture analysis techniques convert the image into a new form using the spatial frequency properties of the pixel intensity variations. Preferable examples of such techniques include Gabor filters, wavelet transforms analysis and Angle measure technique (AMT). Particularly, features derived from a set of Gabor filters can be used in texture analysis for image segmentation. Wavelet transform methods of feature extraction can be used to characterize texture and to treat the problems of texture segmentation and classification. Furthermore, AMT can be used to extract textural features from unfolded image pixel values in order to characterize and predict externally measured reference textures using multivariate statistical techniques.

In a preferable embodiment, the texture in the retina image is analyzed by statistical texture analysis techniques such as GLCM and RLM, and higher order spectral (HOS) features from digital fundas image, for example, the 3rd moment of threshold feature's intensity. It will be understood by the skilled person in the art that the expected area of threshold intensity value for extracted features over whole image area (i.e., mean or probability of intensity) can be considered as the 1st order statistic. GLCM can be a 2nd order measure because it measures the relationship between neighborhood pixels.

In a more preferable embodiment, a combination of wavelet transformation and HOS is used to analyze the texture in the retina image. Most preferably, the texture is analyzed by the wavelet-based Radon transform in combination with HOS. It is known that HOS consists of moment and cumulant spectra and can be used for both deterministic signals and random process. There are total six HOS parameters (features) which can be extracted based on bi-spectral invariants. The bi-spectral invariants contain information about shape of the waveform within the window and are invariant to shift and amplification. Five parameters are Entropy1 (entropy mean), Entropy2 (entropy variance), Entropy3 (entropy 3rd moment), Entropy phase, Entropy magnitude. The extra information provided by HOS would lead to better estimation of parameters and shed light on nonlinearities in the source of signal. Furthermore, the use of higher order spectra can result in good noise immunity.

In a preferred embodiment, detection of abnormal patterns also comprises quantitatively counting the number, area and location of the abnormal patterns.

Preferably, abnormal patterns as defined herein are detected and analyzed by a wavelet approach. In a more preferred embodiment, the abnormal patterns are detected by the wavelet processing in combination with higher order spectral analysis. Most preferably, the wavelet processing is wavelet-based Radon transform or dual tree complex wavelet transform, and higher order spectral feature is the 3rd order spectral analysis.

As described above, the abnormal patterns include, but not limited to, hemorrhage, exudates, new vessels, microaneurysm and proliferative vitreoretinopathy (PVR). Such patterns have clear definition in size, shape, roughness, edge sharpness, brightness, and color (Table 1) (see, Yen, G. G. and W. F. Leong, *A sorting system for hierarchical grading of diabetic fundus images: a preliminary study.* IEEE Trans Inf Technol Biomed, 2008. 12(1): p. 118-30) and thus can be measured by computer program.

TABLE 1

DEFINITION OF THE PATTERNS FOR DIABETIC RETINOPATHY DIAGNOSIS IN COMPUTER PROGRAMMING.

| Features name | Hemorrhage | exudate | New vessels | Microaneurysm | PVR |
|---|---|---|---|---|---|
| Location | Outside optic disc | Outside optic disc | Any | Outside optic disc | Any |
| Size | Large | Any | Large | Small | Large |
| Shape | Arbitrary shape | Arbitrary shape | Chaotic curled aggregated lines | Round | Band-like |
| Roughness | Dull | Waxy | Dull | Dull | Raised above retina |
| Edge sharpness | Insignificant | Significant | Insignificant | Insignificant | dull |
| Type (brightness) | Dark | Bright | Bright | Dark | bright |
| Color | Red | Yellow | Red | Red | white |
| Depth | superficial | Superficial | Superficial | superficial | superficial |

Diabetic retinopathy as disclosed herein can be divided into two categories: non-proliferative diabetic retinopathy and proliferative diabetic retinopathy. The existence of new vessels is the landmark for proliferative diabetic retinopathy. The non-proliferative diabetic retinopathy can be further divided into three classes, which is graded by the existence of MA&HE and exudates and their severity reflected by the number and area. The diagnosis and follow-up scheme of diabetic retinopathy can be based on the guideline of diabetic retinopathy management of American Academy of Ophthalmology 2007 (Table 2).

TABLE 2

Diabetic Retinopathy Disease Severity Scale

| Grading | location | Characteristics | Number | Management |
|---|---|---|---|---|
| Grade one | anywhere | No abnormal patterns detected | 0 | Follow up once a year |
| Grade two | anywhere | Irregular large red spots (hemorrhages) | <10 | Follow up every 6 months |
| Grade three | anywhere | Yellow spots (exudates) | Any | Referral, follow up 2-4 months |
|  | anywhere | Irregular large red spots (hemorrhages) | >10 |  |
| Grade four | anywhere | New vessels | Any | Urgent referral, follow up 2-4 months |

One specific example of the abnormal patterns in diabetic retina image is exudates, which appear as bright yellow-white deposits on the retina due to the leakage of blood abnormal vessels. Their shape and size will vary according to different retinopathy stages. In one embodiment, the detection of exudates comprises first processing the green component of the original colored image for uniformity, and then applying morphological image processing to remove the blood vessels and identify the exudates region.

Another typical example of the abnormal patterns in diabetic retina image is hemorrhage, which is an important feature to be detected in screening or grading diabetic retinopathy. In a preferable embodiment, a morphology-based technique is used for detection of hemorrhages. The technique applies morphology opening and erosion for the binary mask of dark regions produced as the output in the segmentation phase. Particularly, the opening can be performed iteratively with an increasing structuring element (general six times from 0 to 5 is enough, for example) until all hemorrhage lesions can be separated from the blood vessels, and hemorrhage is turned into binary data (black and white).

As described above, the existence of new vessels is the landmark for proliferative diabetic retinopathy, and new vessels is also one kind of abnormal pattern in diabetic retina image. It is known in the art the features which are used for new vessel detection include segment length, gradient (the mean Sobel gradient magnitude along the segment), the Sobel gradient variance along the segment, segment direction, tortuosity 1 (sum of absolute change in direction), tortuosity 2 (maximum difference in angular direction along segment), tortuosity 3 (mean change in angular direction per pixel), the normalised mean segment grey level, Grey Level variance along the segment, distance of segment centroid from disc centre, vessel density, number of segments, mean ridge strength (kappa), mean estimated vessel width, and mean estimated vessel wall gradient.

In some embodiments, a process for detecting new vessels is comprised in the system or method disclosed herein and can be performed based on statistical techniques or transform-based techniques for extracting vessel features. For example, the statistical techniques can apply the mean gradient magnitude with different directions along the segment using a wavelet approach. Preferably, the wavelet approach is DTCWT. In another preferred embodiment, transform-based techniques can involve different order of spectral (at most 3rd order) such as HOS applied on extracted vessels in grey levels or the technique of a wavelet approach such as DTCWT used for extracting vessels.

In an embodiment, a page with Matlab software as a graphics interface between users and computer (GUI) with tools development is created, which has capability to storage data in files. The validation for diagnosis testing is given by using ROC curve with sensitivity, specificity checking The system or method as described in the application can be applied in the detection or diagnosis of other types of retinopathy besides diabetic retinopathy, for example, those related to cardiovascular diseases including stroke and coronary heart disease.

The automatic computer system provides more detailed information than human grading regarding severity of diabetic retinopathy, and thus can be applied for detecting any abnormal patterns so as to screen, diagnose and grading diabetic retinopathy.

In certain embodiments, the automatic computer system can automatically select good quality images and can be able to tell if the quality is acceptable in real time basis.

The retinal photo can be taken again to ensure a reliable result is obtained. By means of the algorithms, mass screening for diabetic retinopathy can be carried out to reduce workload and cost and increase coverage of screening program.

EXAMPLE 1

Clinical Study

Method
Case: Stroke Patients.
Inclusion criteria: clinical diagnosed stroke patients.
Diagnostic criteria of stroke[105]:
1. Stroke symptoms: numbness, paralysis, slurring of speech, blurring of vision, etc. and the diagnosis was confirmed by experienced neurologists;
2. Brain MRI or CT manifestation: ischemic or hemorrhage change of the brain.

Patients were diagnosed as stroke case with the $1^{st}$ criteria with or without the examination of brain MRI or CT. There were totally 122 stroke cases in this study. The cases of stroke were from two sources: 64 of them were from diabetic retinopathy screening program. The screening program was started in January 2008 and diabetic patients followed in the Prince of Wales Hospital were invited to be screened for diabetic retinopathy. There were 64 patients with prevalent stroke have their color retina image record in this screening program. Another 58 stroke cases were acute stroke patients from Acute Stroke Unit in Prince of Wales Hospital from January 2010 to July 2010. These patients were diagnosed as either ischemic stroke or hemorrhage stroke and they had adequate sitting balance to tolerate retinal photography. Written informed consent was obtained from patients or from their next of kin, and the project was approved by the human research ethics committees of the respective hospital. There were 17 patients from the acute stroke unit suffering from diabetes. So, there were totally 81 stroke cases with diabetes.

Exclusion Criteria:
1. age>80 years old. Patients who were older than 80 years usually had optical opacity which was not suitable for color retina capturing. And this age group patients got more complication, and more survival bias would occur if they were included.
2. The quality of the color retina images were too poor to be judged the existence of retina characteristics.
3. Patients with eye disease that had influence on the retina vessel structures or spot characteristics, such as glaucoma, trauma, uveitis, choroid new vessels, etc.
4. Stroke subtypes of cardioembolic stroke, subarachnoid hemorrhage.

Control: Patients without Stroke Event.
122 controls were selected to compare with the stroke cases. Controls were from two sources: patients without stroke in diabetic retinopathy screening program in Prince of Wales Hospital. Other controls were patients without stroke and obvious eye diseases that influenced retina vessel structure or spot patterns in Eye Outpatient Clinics in Prince of Wales Hospital. The mean follow-up period from the date of retina image capturing to July 2011 was 4.3 years. The proportion of diabetes patients in stroke cases were high in this case control study. And diabetes has special characteristics in retina, which is called diabetic retinopathy. As described in the introduction, about 40% diabetes patients got diabetic retinopathy after ten year history of diabetes[106], whereas, very small amount patients without diabetes got retinopathy. In this study, 81 stroke cases suffered from diabetes. To minimize the confounding effect of diabetes, we selected 81 diabetic patients without stroke as controls. And the other 43 patients without diabetes as controls. All the controls were aged from 50 to 80 years old.

Inclusion criteria of controls in eye clinics:
Age>50 years old
No retina disease or with only mild diseases without influencing vessel structure in color retina images, such as mild age-related maculopathy, central serous chorioretinopathy, post-cataract extraction, retinal pigment epithelial detachment.

Exclusion Criteria:
1. Patients with retina diseases that influence retina vessel structure or pattern characteristics. Any eye diseases that are related to the diameter changes of vessels, such as glaucoma[107], central/branch retina vein/arteriole occlusion, severe myopia, O/D ratio >0.5, tumor, any disease that leads to hemorrhages or exudates, such as choroidal new vessel, idiopathic polypoidal choroidal vasculopathy. Only patients with routine eye checkup, recovered central serous chorioretinopathy, mild quiet age related maculopathy confirmed by Fluorescein and Indocyanine Green Angiography were included as controls. Other eye diseases, such as glaucoma, occult choroid new vessels, optic disc atrophy or edema, etc, were excluded.
2. Patients that have ever suspected to suffer from cerebral diseases;
3. Patients with diseases that influence vessel morphology such as rheumatoid diseases, peripheral vascular disease.
4. Patients with head or neck radio-therapy.
5. Patients younger than 50 years old and older than 80 years old.

Stroke Risk Factors Measurement
Stroke risk factors including age, gender, hypertension, diabetes, history of cardiovascular complications (myocardial infarction, angina, cardiac syndrome X, atrial fibrillation), blood lipid level, level of HbA1c in diabetes patients, smoking status were recorded for all subjects in this study. The stroke types such as ischemic stroke, transient ischemic attack, hemorrhage stroke and their manifestation in MRI and/or CT were also recorded. The stroke type was judged by the CT/MRI at acute phase or later in the follow-up.

Retina Characteristics Description
Diameter of Arterioles and Venules
The formula developed by Knudtson et al[64] was used to summarize the diameters of arterioles in one retina image. The methods were described elsewhere[Ref]. in concise, a circle was drawn around the edge of optic disc. The diameter of optic disc was measured. Six largest arterioles within the circle 0.5 to 1 diameter apart from the edge of optic disc were selected. A line perpendicular to the edge of vessel walls was drawn and measured as the diameter of the arteriole. With these six diameters, we summarized one parameter "CRAE" by Knudtson's formula to represent the arteriole diameter of the retina. Similarly, "CRVE" was used to summarized the venule diameters. AVR (arteriole-venule ratio) was calculated as the ratio of CRAE to CRVE.

Arteriole-Venous Nicking
This sign was marked as the narrowing of venule at the crossing point of arteriole.

Measurement of Pattern Characteristics Hemorrhages, Exudates
Hemorrhage and exudates were recorded as either exist or not. Other retinopathy including microaneurysms, new vessels, cotton-wool spots, was extracted from the images but was not included into analysis. microaneurysms were not included was due to its detection was prone be have measurement error. The other retinopathy's occurrence in the images was very low. Hemorrhage and exudates were key determinants for the severity of diabeteic retinopathy, they were found to be associated with stroke and they are less suffered from interobserver variability. That is why hemorrhages and exudates were extracted from the color retina images The sample size was not large enough to demonstrate the association of the severity of the spot characteristics with stroke.

Measurement of Tortuosity

Tortuosity was assessed by visual grading of one fovea-centred and one disc-centred fundus image from each eye displayed on a computer display and viewed by a medical doctor (first of this paper) with 3 years of experience in ophthalmology research, especially trained in evaluating retinal blood vessels in fundus photographs. A grading scale was developed for the study based upon a preliminary inspection of the study photographs, which indicated that an acceptable reproducibility could be achieved using a two-level scale for arterial tortuosity. The grading levels for retinal arterial tortuosity were (FIG. 7): Category 1 (predominantly straight arteries); Category 2 (mild to severe tortuosity with at least one inflections of at least one major artery); The first author examined all images twice at an interval of 2 months in random order, masked to disease status. The intra-observer variability Kappa is 0.869.

Bifurcation of Arterioles and Venules

Branching coefficient (BC) or "area ratio" is the ratio of the sum of the cross-sectional areas of the daughter vessels of a bifurcation to that of the parent stem. Branching angle is the angle between the two daughter branches. Asymmetry index (AI) is the ratio of diameters of two daughter branches. Their calculation is below:

$$BC=(D_1^2+D_2^2)/D_0^2.$$

$$AI=D_1/D_2,$$

Where $D_0$, $D_1$, $D_2$ are the diameter of trunk, the smaller branch and the larger branch of one bifurcation point.

Niall Patton et al[95] showed that the bifurcation coefficients of different bifurcation of vessels in the same retina image did not correlate to the eccentricity to the edge of optic disc. So not all bifurcations of the all branches of arterioles or venules were selected to calculate to bifurcation coefficients. The population in this study were elderly aged from 50 to 80 years old, with mean age of 66 years old. The optic media was opaque to some extent. The smaller branches of vessels were not visualized clearly in most of the images. The vessels that were smaller than 4 pixels were difficult to measure correctly. Lastly, the methods to summarize diameter "CRAE" and "CRVE" focus on the vessels near optic disc. In this study, we focus on summarizing the information of larger branches, so we extracted the bifurcation of three sets of branches of arterioles and three sets of bifurcation of venules which were closest to optic disc.

Parameter Description:

The continuous retina parameters include the information of vessel diameters and bifurcations. The perimeters of optic disc were used as scale to adjust the magnification effect of retina cameras. There might be more than one bifurcation information in one retina, to relatively reduce the selection bias of the bifurcations, the mean of bifurcation coefficients and bifurcation angle and branch asymmetry were used for the analysis. The meaning of parameters were summarized below:

CRAE: diameter equivalent of arterioles;
CRVE: diameter equivalent of venules;
OD: perimeter of optic disc;
AdjustedCRAE: the ratio of CRAE to OD;
AdjustedCRVE: the ratio of CRVE to OD;
AVR: arteriole to venule ratio, the ratio of CRAE to CRVE;
BCA: mean bifurcation coefficient of arterioles;
BCV: mean bifurcation coefficient of venules;
Aangle: mean bifurcation angles of arterioles;
Vangle: mean bifurcation angles of venules;
Aasymmetry: mean asymmetry index of arterioles; the lesser the value, the bigger of arteriole asymmetry;
Vasymmetry: mean asymmetry index of venules; the lesser the value, the bigger of venule asymmetry;

Retinal Photography and Image Analysis Procedure

Canon-non-mydriatic retinal camera CR-1 with the angle of view of 45 degree was used in the diabetic retinopathy screening program. Topcon Retinal Camera TRC-50IX with angle of view of 50 degree was used in eye outpatient clinics to take color retina image. Photographs of the retina were taken of 1 randomly selected eye after 5 minutes of dark adaptation.

Magnification Adjustment of Images from Different Sources

Retina images were from two sources where two different retina cameras were used. The original retina images taken by Canon-non-mydriatic retinal camera CR-1 were stored originally as TIFF format with 1536*1024 pixels. And the retina images taken by Topcon Retinal Camera TRC-50IX were originally stored as JPG format with 1365*1024 pixels. The parameters of bifurcation coefficient, bifurcation angle, branch asymmetry, aterio-venule ratio were dimensionless parameters. They were not influenced by magnification of retina images. The parameters of spot characteristics, such as microaneurysms, hemorrhages, exudates, cotton wool spots, new vessels were judged as existence or not. They were also not influenced by the magnification of retina photos. The parameter of CRAE or CRVE was influenced by the magnification of retina images. Even for the same retina photos, different axial length, refractive error and eye to camera distance would have effect on the magnification, which made the direct comparisons of CRAE or CRVE between different subjects not accurately. To adjust the magnification effect and directly compare the difference of CRAE and CRVE which were probably correlated to stroke event among different subjects, we first resized and adjusted all retina images into JPG format with 1365*1024 pixels. Then we assumed that the diameter of optic disc was the same among different subjects. And the ratio of CRAE or CRVE to the diameter of optic disc was calculated as "adjusted CRAE" and "adjusted CRVE". We used the "adjusted CRAE" and "adjusted CRVE" to represent the arteriole diameters and venule diameters of retina images and compare them in different subjects directly.

Software Used to Quantify the Retina Characteristics.

All continuous parameters are measured by ImageJ by pixels. Retina images were adjusted to the same resolution of 1365*1024 pixels by ImageJ. The length and angle measurement tools of ImageJ were used to measure the length and angle of vessels.

Statistical Analysis

Intraclass correlation coefficient was used to test the intra-observer reliability of the parameters measured by software ImageJ, including CRAE, CRVE, bifurcation coefficient of arterioles, bifurcation coefficient of venules, branching angle of arterioles, branching angle of venuels, asymmetry index of arterioles, asymmetry index of venules, diameter of optic disc.

For univariate analysis, the continuous parameters were compared between cases and controls by two sample independent t test. The categorical data was analysis by chi-squire test. Logistic regression was used to select variables that were different between the two groups controlling for the demographic data. All data were analyzed by SPSS 16.0.

Results
Reliability Test

Eighteen color images were randomly selected from the control to test the intra-observer variability. The first author measured all the parameters in the interval of two months.

The intraclass correlation coefficients of each parameter of two measurements were summarized in Table 3.

TABLE 3

INTRACLASS CORRELATION COEFFICIENTS OF EACH PARAMETERS

| Parameter | Intraclass Correlation coefficients (95% confident interval) Single Measures |
|---|---|
| CRAE | 0.828 (0.605~0.932) |
| CRVE | 0.821 (0.591~0.928) |
| BCA | 0.294 (−0.176~0.659) |
| BCV | −0.106 (−0.528~0.364) |
| Aangle | 0.949 (0.873~0.981) |
| Vangle | 0.812 (0.574~0.925) |
| Aasymmetry | 0.289 (−0.192~0.658) |
| Vasymmetry | 0.579 (0.168~0.819) |
| OD | 0.977 (0.939~0.991) |

From the table above, we could see that the intraclass correlation coefficients of CRAE, CRVE, Aangle, Vangle, OD were high enough that we might feel confident that intra-observer reliability of these parameters was high. The intra-class correlation coefficient of Vasymmetry was 0.579 for single measurement and 0.733 for average measurements, which might be acceptable for the further analysis of its relationship with stroke. Other parameters including BCA, BCV, Asymmetry had quite low intraclass correlation coefficients. New methods had to be developed to summarize these parameters to reach acceptable intra-observer and inter-observer reliability.

Descriptive Demographics:

A total 244 patients were recruited in this study, and 122 of them with event of stroke and the other 122 patients without stroke. Among all subjects, there were 10 patients suffered from hemorrhage stroke, others suffered from ischemic stroke or transient ischemic attack. The demographic data were given in Table 4. Since the status of diabetes and age were matched between the two groups as the design of the study, there was no difference of age, diabetes, smoking status, cardiac complications, and hyperlipidemia between the two groups. Among the stroke patients, ten of them suffered from hemorrhage stroke, and others were ischemic stroke.

TABLE 4

DEMOGRAPHIC DATA DESCRIPTION

|  | All subjects | Controls n = 122 | Stroke n = 122 | P |
|---|---|---|---|---|
| Age (years) | 65 ± 8.2 | 66 ± 8.1 | 65 ± 8.2 | 0.276 |
| Male | 155 | 81 | 74 | 0.304 |
| Hypertension | 174 | 80 | 94 | 0.048 |
| Diabetes | 162 | 81 | 81 | 1.000 |
| Smoker* | 68 | 29 | 39 | 0.164 |
| Cardiac complication# | 24 | 10 | 14 | 0.401 |
| Atrial fibrillation | 12 | 1 | 11 | 0.005 |
| Hyperlipidemia | 190 | 93 | 97 | 0.994 |

Difference of atrial fibrillation might be due to bias of body checkup. All stroke patients will have electrocardiogram to detect whether they have ischemic heart disease and atrial fibrillation. The ischemic heart disease manifested as chest pain could be demonstrated by patients, whereas, the symptoms of atrial fibrillation may be occult. The lower proportion of atrial fibrillation in controls may be under reported. The proportion of hypertension was lower in control group.

Univariate Analysis of Continuous Retina Characteristics

The summaries of continuous retina characteristics were given in Table 5.

TABLE 5

SUMMARIES AND COMPARISONS OF CRAE, CRVE, OD, ADJUSTEDCRAE, ADJUSTEDCRVE, AVR, BCA, BCV, AANGLE, VANGLE, AASYMMETRY, VASYMMETRY BETWEEN CONTROL GROUP AND STROKE GROUP.

|  | Control | | | Stroke | | | | |
|---|---|---|---|---|---|---|---|---|
|  | N | mean | SD | N | mean | SD | t | P |
| CRAE* | 112 | 14.35 | 3.192 | 108 | 11.48 | 1.537 | 8.565 | <0.001 |
| CRVE* | 114 | 21.16 | 3.640 | 108 | 18.16 | 2.054 | 7.618 | <0.001 |
| OD* | 120 | 497.9 | 79.46 | 122 | 451.6 | 41.95 | 5.654 | <0.001 |
| Adjusted CRAE* | 111 | 0.02850 | 0.004582 | 108 | 0.02572 | 0.004426 | 4.558 | <0.001 |
| Adjusted CRVE* | 113 | 0.04243 | 0.005320 | 108 | 0.04077 | 0.005330 | 2.316 | <0.001 |
| AVR* | 112 | 0.6777 | 0.09207 | 107 | 0.6331 | 0.0796296 | 3.823 | <0.001 |
| BCA | 112 | 1.590 | 0.3323 | 107 | 1.639 | 0.48134 | −0.880 | .380 |
| BCV* | 115 | 1.304 | 0.2366 | 108 | 1.239 | 0.2029 | 2.195 | .029 |
| Aangle | 114 | 70.32 | 12.51 | 108 | 72.59 | 11.44 | 1.059 | .291 |
| Vangle | 112 | 72.52 | 11.86 | 107 | 70.85 | 11.56 | −1.403 | .162 |
| Aasymmetry | 112 | 0.8344 | 0.08026 | 107 | 0.8270 | 0.1008 | .598 | .550 |
| Vasymmetry | 115 | 0.7755 | 0.09066 | 108 | 0.7572 | 0.09009 | 1.511 | .132 |

*p < 0.05.

From the results of univariate analysis, we can see that CRAE, CRVE, OD were significantly different between the two groups. This difference should be due to the magnification effect of retina camera. So we should use the parameters, adjustedCRAE, adjustedCRVE for direct comparisons of arteriole diameters or venule diameters between the two groups. We could see that both of the adjustedCRAE and adjustedCRVE were significantly smaller in the stroke group than the control group. The AVR were also significantly smaller in the stroke group. We could judge that both arterioles and venules were smaller in stroke patients, while the arteriole diameters reduced much more than venule diameters. BCV was significantly different between the two groups. The Vasymmetry was marginally significant with P=0.132. Other parameters such as BCA, Aangle, Vangle, Aasymmetry were not significantly different between the two groups.

There were totally 25 color retina images that no diameters were recorded. And 10 of them were in the control group, the other 15 were in stroke group. Some of them were due to the opacity of the media and it was difficult to record the diameters. Some of them were due to eye vascular abnormalities that it was impossible to measure the diameters.

Univariate Analysis of Categorical Retina Characteristics Results

The retina characteristics including vessel tortuosity, arteriole-venule nicking, hemorrhages, exudates and arteriole occlusion were marked as existed or not. So they were regarded as categorical parameters in this study. the frequency of their existence were summarized and compared in the Table 6.

TABLE 6

SUMMARIES AND COMPARISONS OF THE CATEGORICAL RETINA CHARACTERISTICS.

|  | Control N = 122(%) | Stroke N = 122(%) | $\chi 2$ | P |
| --- | --- | --- | --- | --- |
| Arteriole-venule Nicking* | 11(9.02%) | 28(22.95%) | 9.208 | 0.02 |
| Tortuosity* | 15(12.30%) | 42(34.43%) | 16.688 | <0.001 |
| Hemorrhage* | 11(9.02%) | 31(25.41%) | 11.544 | 0.001 |
| Exudates* | 11(9.02%) | 23(18.85%) | 4.700 | 0.03 |
| Arteriole occlusion* | 2(1.64%) | 7(5.74%) | 2.928 | 0.087 |

*significantly different between controls and stroke cases, p < 0.05.

The occurrence of arteriole-venuous nicking, vessel tortuosity, hemorrhages, exudates and arteriole occlusion were all significantly higher in the stroke group than in the control group.

Multivariate Analysis Results

Strategy of Building Model for Stroke Risk Stratification

The aim of the risk model building is to detect the important retina characteristics associated with stroke and their risk modifier effects of each other. The risk model for stroke had main effects and retina characteristics. The main effects were well known risk factors of stroke. The main effects included diabetes, hypertension, hyperlipidemia, history of ischemic disease, atrial fibrillation, smoking, age and gender. The variables of retina characteristics were adjustedCRAE, adjustedCRVE, AVR, BCA, BCV, Aangle, Vangle, Aasymmetry, Vasymmetry, arteriole-venule nicking, tortuosity, hemorrhages, exudates, ateriole occlusion. In this case control study, we controlled the status of diabetes and age. So this study can't address the risk of diabetes and age for stroke. But diabetes and age were left in the model for controlling confoundings. Parameters of BCA, BCV, Aasymmetry were found to have poor intra-observer reliability. Aangle and Vangle were not significantly different between controls and stroke cases. They were not included into the risk model. The rest retina characteristics were discussed below separately:

Risk Model Establishment

TABLE 7

PROCEDURES IN RISK MODEL ESTABLISHMENT.

| Step | Variables included in risk score | Percentage Correct (%) |
| --- | --- | --- |
| 1 | Model 1# | 59 |
| 2 | Model 2$ | 74.5 |
| 3 | Model 2 + interaction of hypertension* | 73.5 |
| 4 | Model 2 + interaction of diabetes§ | 74 |
| 5 | Model 2 + interaction of retina characteristics☆ | 77.5 |
| 6 | Model 3◇ | 80.4 |

Model 1 included main effects: age, hyperlipidemia, smoke, gender, IHD, AF, hypertension, diabetes.
$Model 2 includes model 1 + retina characteristics including adjustedCRAE, Vasymmetry, tortuosity, nipping, hemorrhage.
*Interaction of hypertension include three interaction variables: adjustedCRAE by hypertension, hypertension by tortuosity, hemorrhage by hypertension.
§Interaction of diabetes include Vasymmetry by diabetes
☆Interaction of retina characteristics include three interaction between retina characteristics: Vasymmetry by adjustedCRAE, adjustedCRAE by hemorrhage, Vasymmetry by tortuosity
◇Model 3 retina characteristics + interaction of retina characteristics + diabetes + atrial fibrillation The steps of risk model establishment were presented in Table 7. All variables of retina characteristics were statistically significant in the model two. The interaction between retina characteristics and diabetes or hypertension was not statistically significant when control for the main effects and retina characteristics. And the model with interaction of retina characteristics and diabetes or hypertension did not get higher accuracy of classification. The interaction of Vasymmetry by adjustedCRAE, adjustedCRAE by hemorrhage, Vasymmetry by tortuosity was statistically significant in step 5. And the model in step 5 had higher accuracy in classification than model 2, which means that the interaction between retina characteristics was important for the classification of stroke patients from patients without stroke. In model 3, the main effects which were not statistically significant and no contribution in the accuracy were removed from the model in step 5. And the model 3 had the highest accuracy of classification.

Model 3 was presented below:

Logic $P(x)=-10.895+(0.281)*(hypertension)+(-0.773)*(diabetes)+(2.815)*(AF)+(20.683)*(adjustedCRAE)+(21.987)*(Vasymmetry)+(-10.087)*(tortuosity)+(1.154)*(nipping)+(-8.135)*(hemorrhage)+(-39.021)*(Vasymmetry$ by $adjustedCRAE)+(14.302)*(adjustedCRAE$ by $hemorrhage)+(15.590)*(Vasymmetry$ by tortuosity)

Receiver Operating Characteristic (ROC) Analysis of the Risk Models

We measure the individual risk predictivity of the risk model 3 by the area under curve (AUC) the ROC. The probability that a person who had stroke event would have a higher risk score than a person who did not have an event. (FIG. 8) The area under curve was 0.836, 95% confidence interval was 0.7800.892 using SPSS cross-validation method which may an over-estimation. When we use random forrest method for validation of this model, we obtained AUC=0.74, sensitivity of 0.76 and specificity of 0.73.

EXAMPLE 2

Automated Computer Methodology

FIG. 1 shows the overall system used for stroke epidemiology prevention and risk assessment tools. As can be seen from FIG. 20, there are total five steps that need to be addressed for the system to carry out diagnosis for stroke.

2.1 Automated and fast measurement of the image quality 2.2.1 Blood vessels features: vessels width and the Arteriolar-to-Venular diameter Ratio (AVR), we may also consider part e) as one of the blood vessel feature.

2.2.3 Texture properties related to stroke: mainly from the spectrum concerning.

2.2.4 Fractal Analysis—Other features including retinal arteriolar narrowing, arteriole-venule nicking and vessel tortuosity, which any irregular shape related to stroke (may be too complicate measured/extracted from image). We use fractal analysis to deal with such kind of features.

2.2.5 Other stroke features that related to DR retinopathy: Hemorrhages

The detailed information for above five steps is given as follows.

Automatic Assessment of the Image Quality

We would like to carry out a stable and reliable medical evaluation from a single fundus photograph. In general, the clinical usefulness of an image is highly dependent on its quality. In the image processing techniques (FIG. 1), we mainly focus on image quality assessment and enhancement. Previous studies on retinal images that do quality assessment[108-115], focus mainly on two aspects: image clarity and field definition. These aspects depend on features of various diseases. However, almost all of these studies (image clarity and field definition) are based on a numerical quantification of image sharpness and illumination. In this project we develop an automatic method to carry out the quality evaluation on quality of digital fundus photographs.

At first, we use the techniques for the automatic image quality assessment of retinal fundus image based on structural criteria and generic criteria. Structural criteria include the level of recognition of optic disc structure and vessel structure. Generic criteria include level on homogeneous illumination and also, bright and high-contrast background. Other than applying some clustering method, sharpness metric and texture features (Haralick texture features), we developed a new assessment method based on fractal analysis from both grey level images and vessel extracted binary (black and white) images. The detailed procedure is given in the following:

Step 1: Preprocessing the original input image (convert to gray level image) in simply removed noise without shift variance problem by using dual-tree complex wavelet (DT-CWT) technique.

Remark: We can enhance the qualified image contrast with color histogram and dual tree complex wavelet-transform (DTCWT). This technique will benefit almost all features extracted for Stroke in the retinal image. The reason we applied color histogram with statistical properties because of its well presenting of color properties. The DTCWT method (transform without decimation) can overcome the problem of the traditional (ordinal) discrete wavelet transform because it is not shift invariant and the decimation operation during the transform can be dealt with. A small shift in the input signal can cause very different output wavelet coefficients. This will provide benefit for the denoising process and enhance the contrast at the same time. In other words, we can keep the detailed information of the features without having the noise involved.

Step 2: Automatic image quality assessment from two aspects: on gray level image and on vessel extracted image. For gray level image, we apply the method consists of a sharpness metric, Haralick texture features[116] and fractal analysis related parameters. For the extracted vessel image, we apply the fractal analysis again. All of these results (parameters) will be generated and used to classify the level of acceptability of the qualified image (AQI/NAQI), while AQI/NQAI is provided by professional Ophthalmology experts justified from their screening results.

Step 3: Finally we will apply some statistical methods such as logistic regression, generalized linear model or improved logistic regression method supervised penalized logistic regression and Random forest to determine important parameters. At the same time, a prediction model with these parameters is obtained. validation using the ROC curve with the area under ROC curve plus the sensitivity and specificity will be provided to justify the results.

Study on the Automatic Quality Control Process

A dataset of 143 subjects are classified by an experienced eye specialist. There are total of 88 retinal images that are qualified for further screening, while 55 retinal images are not qualified. I The study results based on above approach is provided as follows:

TABLE 8

AFTER 20 RUNS (RANDOM SAMPLED BY 70% AS TRAINING DATASET AND 30% AS TESTED DATASET) OF RANDOM FOREST CLASSIFICATION, WE HAVE A SUMMARY OF THE ROC CURVE RESULTS AS FOLLOWS.

| | Retinal Image Quality Classification for Further Analysis | | |
| --- | --- | --- | --- |
| times | AUC | Sensitivity | Specificity |
| 1 | 0.9955 | 1 | 0.96 |
| 2 | 0.9768 | 0.875 | 1 |
| 3 | 0.98 | 0.8888 | 0.96 |
| 4 | 0.9819 | 1 | 0.9230 |
| 5 | 0.9211 | 0.6428 | 1 |
| 6 | 0.9846 | 0.9473 | 1 |
| 7 | 0.9704 | 0.9166 | 0.9677 |
| 8 | 1 | 1 | 1 |
| 9 | 0.9926 | 1 | 0.9655 |
| 10 | 0.9846 | 0.8421 | 1 |
| 11 | 0.9977 | 0.9444 | 1 |
| 12 | 0.9956 | 0.9473 | 1 |
| 13 | 0.9753 | 0.9285 | 0.9655 |
| 14 | 0.9864 | 0.9411 | 1 |
| 15 | 0.9978 | 1 | 0.9583 |
| 16 | 1 | 1 | 1 |
| 17 | 1 | 1 | 1 |
| 18 | 0.9733 | 0.8888 | 0.96 |
| 19 | 0.9952 | 1 | 0.9642 |
| 20 | 0.9932 | 1 | 0.9230 |
| average | 0.9851 | 0.9381 | 0.9773 |

From above result, we can see that with a total 143 subjects of retinal images with 88 good and 55 poor quality images for quality assessment (identification), after 20 random sampling with replacement from original retinal images (70% for training and 30% for testing), there is an average of AUC almost 99% accuracy. We also obtain a sensitivity of about 94% and a specificity of about 98% as detected by the automatic system. To obtain this result we first applied supervised penalized logistic regression method to extract significant features from total 26 texture and fractal features. Five of the significant features such as maximum probability, Sum average, correlation from texture related features and Hausdorff dimension from binary retinal image of vessels, box-counting with Fourier fractal dimension (slope) and intercept from gray level retinal image (fractal analysis) that are extracted. The validation of classification based on random forest is given and the accuracy is measured by the area under the ROC curve This result is considered as excellent accuracy for classification of the quality of the retinal images for the diagnosis purpose.

0.90-1=excellent (A)
0.80-0.90=good (B)
0.70-0.80=fair (C)
0.60-0.70=poor (D)
0.50-0.60=fail (F)

In addition, the wavelet-based multi-fractal analysis approach will applied to improve the result as well in future study.

Stroke Related Features Extracted from Vessels

Abnormalities of retinal vasculatures may indicate poor health conditions in the body. The width ratio of arteries and veins (A/V ratio) on the retinal fundus images may help physicians in diagnosis of hypertensive retinopathy, which related to stroke. Other features related to stroke include bifurcation and tortuosity. Referring to previous study[117-133], retinopathy vessel diameter, arteriole-venule nicking, artery occlusion, venule occlusion have been reported to be related to stroke. Since two components of the Central Retinal Artery Equivalent (CRAE) and the Central Retinal Vein Equivalent (CRVE) involve most of the above information. We will focus on CRAE, CRVE or AVR where AVR=CRAE/CRVE. Rest of stroke-related risk factors will be obtained from other two methods: texture analysis and fractal analysis.

Recall that the manual computation of AVR is a tedious process, since it involves repeated measurements of the diameters of all arterioles and venules in the region by human graders. To facilitate large-scale clinical use, an accurate, rapid and efficient system to compute AVR is required. This project simply used the vessel network traced by a vessel tracking algorithm and then the vessel caliber is estimated. Vessels are then classified as either arteries or veins and AVR parameter is then obtained. The detailed procedure is given as follows:

Step 1: After Vessel segmentation (extracted) using techniques in previous project (diabetes), we work on thinning the vessel (centerline detection) and find the optic disc center point to obtain the region of interest (ROI: a circle within 0.5 to 1 diameter apart from the edge of optic disc). Then each vessel width measurement is obtained within the ROI by using Ai/Li, where Ai is the total area for vessel i and Li is the pixel length for center line of that vessel.

Step 2: Artery-Vein (A/V) Discrimination

To enable separate analysis of the arteries and the veins in the image, the previously detected vessel segments need to be assigned to one of these two classes. We used a supervised system such as Random Forest improved logistic regression method, i.e. trained with examples. After a one-time training procedure the method can be used to classify previously unseen centerline pixels into either artery or vein (AV classification). Notice that an expert indicated whether a given major vessel was an artery or vein for each of the training images. Referring to the method in[134] with Random Forest, it improved on the logistic regression as we can classify Artery-Vein (A/V).

Step 3: AVR Estimation

From the arteriolar and venular calibers estimated by the above steps, the CRAE and CRVE parameters can be computed by the formula: AVR=CRAE/CRVE. Notice that the AVR can provide an indication of a possible generalized arteriolar narrowing[136-142]. Simply the widest 6 veins and arteries (these do not have to be paired) are entered although fewer total numbers of widths can be used in case not enough measurement points are available.

Step 4: Compare to the tested manual AVR Estimation and after validation we can use it for the detection of stroke.

Texture Analysis

Efficient feature extraction is one of the most significant aspects of texture analysis in computer vision applications. Most existing feature extraction methods provide efficient tool for shape and pattern classification in the images (Chen, Nixon, & Thomas, 1994; Pietikainen, Ojala, & Xu, 2000; Tianhorng & Kuo, 1993). But the situation becomes complicated, while both size and shape of particles in the images come into a focus of public attention.

Although one can intuitively associate several image properties such as smoothness, coarseness, depth, regularity, etc. with texture[143], there is no formal or complete definition of texture. Many researchers have described texture using various definitions. Russ[144] loosely defined image texture as a descriptor of local brightness variation from pixel to pixel in a small neighborhood through an image. Alternatively, texture can be described as an attribute representing the spatial arrangement of the gray levels of the pixels in a region of a digital image[145]. Texture analysis, its tasks are mainly classification, segmentation, and synthesis[146-148].

The approaches for analyzing texture are very diverse, and differ from each other mainly by the method used for extracting textural features. Four categories can be defined: (1) statistical methods, (2) structural methods, (3) model-based methods, and (4) transform-based methods.

Statistical texture analysis techniques primarily describe texture of regions in an image through higher-order moments of their grayscale histograms[149]. Probably, the most frequently cited method for texture analysis is based on extracting various textural features from a gray level co-occurrence matrix (GLCM)[150]. The GLCM approach is based on the use of second-order statistics of the grayscale image histograms. Alternatively, the run length matrix (RLM) encompasses higher-order statistics of the gray level histogram. The RLM texture analysis approach characterizes coarse textures as having many pixels in a constant gray level run and fine textures as having few pixels in such a run[151]. Besides traditional statistical texture analysis, multivariate statistical methods have also been proposed for textural feature extraction. Considering an image as a matrix, the Singular Value Decomposition (SVD) spectrum is a summary vector of image texture represented by its singular values. The SVD spectrum has been used as a textural feature vector for image classification[152,153].

Structural texture analysis techniques describe a texture as the composition of well-defined texture elements such as regularly spaced parallel lines. The properties and placement rules of the texture elements define the image texture. Various structural texture analysis approaches have been proposed, ranging from using different shapes of structuring elements[154] to conceiving real textures as distorted versions of ideal textures[155]. However, these methods appear to be limited in practicality since they can only describe very regular textures[143].

Model-based texture analysis techniques generate an empirical model of each pixel in the image based on a weighted average of the pixel intensities in its neighborhood. The estimated parameters of the image models are used as textural feature descriptors. Examples of such model-based texture descriptors are autoregressive (AR) models[152], Markov random fields (MRF)[153], and fractal models[154].

Finally, transform-based texture analysis techniques convert the image into a new form using the spatial frequency properties of the pixel intensity variations. The success of these latter techniques lies in the type of transform used to extract textural characteristics from the image. Indhal and Naes[155] illustrated the use of spectra from 2-D Fast Fourier Transform (FFT) magnitude images for textural feature extraction. Image classification using Multi-way Principal Component Analysis (MPCA) on 2-D FFT magnitude images to extract features from various images was used by Geladi[156]. The Gabor or Wavelet transforms have been preferred recently in image texture analysis due to their space-frequency decomposition abilities. Features derived from a set of Gabor filters have been widely used in texture analysis for image segmentation[157]. Wavelet transform methods of feature extraction have been used to characterize texture and to treat the problems of texture segmentation and classification[146-148, 158-160]. The Angle Measure Technique (AMT) has been used to extract textural features from unfolded image pixel values in order to characterize and predict externally measured reference textures using multivariate statistical techniques[153, 161].

Therefore, we may consider Texture is a representation of the surface and structure of an image. It is also defined as a common pattern on a surface. Image textures provide information about the spatial arrangement of colors or intensities such as tone variation, shape, size, color, brightness etc.

In this project we proposed a novel method for stroke detection using a combination of texture and higher order spectral (HOS) features from digital fundas image. Statistical texture analysis techniques such as GLCM and RLM, and the $3^{rd}$ moment of threshold feature's intensity are used. At first, statistical texture features for the image samples are grouped according to their classes (herein, we have the classes of control and stroke, the classes for grading of stroke will be considered in future study), normalized and into independent t-test (or Analysis of Variance) to test the hypothesis between the classes. At this stage, we first extract Gray-level Co-occurrence Matric Texture features, which include mean of Homogeneity, Energy, entropy, Contrast, Symmetry, Correlation, $1^{st}$ Moment, $2^{nd}$ moment to $4^{th}$ moment and etc. Other features come from the difference statistical features such as Angular $2^{nd}$ moment and etc., features from Run Length Matrix Texture including Mean Short (Long) Run Emphasis and etc., total about 32 features and the most significance features from all GLCM and RLM related that are highly associated with stroke. In fact, the RLM are shown to be more useful for image quality assessment but not in stroke detection. On the other hands, for HOS features extraction we used similar approach as we did in diabetic retinopathy study, HOS elicits both amplitude and phase information of a given signal. It offers good noise immunity and yields good results even for weak and noisy signals. It consists of moment and cumulant spectra and can be used for both deterministic signals and random process[162]. First we applied image enhancement techniques using DTCWT with histogram equalization, and Random transform was performed for HOS feature extraction. Notice that Radon transform is used to detect features within an image. There are total six HOS parameters (features) can be extracted based on bi-spectral invariants. The bi-spectral invariants contain information about shape of the waveform within the window and are invariant to shift and amplification and robust to time-scale changes[163]. Five parameters are Entropy1 (entropy mean), Entropy2 (entropy variance), Entropy3 (entropy $3^{rd}$ moment), Entropy phase, Entropy Magnitude.

Remark:

One of the advantages of using HOS would be that the extra information provided by HOS leads to better estimation of parameters and sheds light on nonlinearities in the source signal. It can also be useful because they suppress addictive colored Gaussian noise of an unknown power spectrum. They identify non-minimum phase signals. They are useful in extracting information that cannot be done by other methods. Lastly they detect and characterize nonlinear properties in signals. The use of higher order spectra results in good noise immunity, as verified with synthetic and real images.

The early study (A Case-control) result based on this approach is provided as follows (Texture and high order spectra related automatic extracted features):

TABLE 9

AFTER 20 RUNS (RANDOM SAMPLED BY 70% AS TRAINING DATASET AND 30% AS TESTED DATASET) OF RANDOM FOREST CLASSIFICATION, WE HAVE THE SUMMARY FOR THE ROC RESULTS:

| T | Texture-detected features | | | High order spectra-detected features | | |
|---|---|---|---|---|---|---|
| | AUC | Sens. | Specs. | AUC | Sens. | Specs. |
| 1 | 0.76 | 0.98 | 0.53 | 0.73 | 1 | 0.5 |
| 2 | 0.77 | 1 | 0.46 | 0.71 | 0.97 | 0.49 |
| 3 | 0.71 | 0.79 | 0.61 | 0.66 | 0.84 | 0.53 |
| 4 | 0.72 | 0.63 | 0.73 | 0.67 | 0.17 | 1 |
| 5 | 0.66 | 0.95 | 0.4 | 0.7 | 0.84 | 0.6 |
| 6 | 0.8 | 0.7 | 0.78 | 0.78 | 0.79 | 0.68 |
| 7 | 0.69 | 0.89 | 0.51 | 0.67 | 0.97 | 0.38 |
| 8 | 0.75 | 0.76 | 0.66 | 0.7 | 0.79 | 0.59 |
| 9 | 0.7 | 0.86 | 0.53 | 0.63 | 1 | 0.34 |
| 10 | 0.75 | 0.92 | 0.51 | 0.75 | 0.92 | 0.59 |
| 11 | 0.78 | 0.92 | 0.6 | 0.73 | 0.95 | 0.49 |
| 12 | 0.74 | 0.84 | 0.67 | 0.63 | 0.84 | 0.44 |
| 13 | 0.65 | 1 | 0.43 | 0.7 | 0.97 | 0.46 |
| 14 | 0.78 | 0.84 | 0.7 | 0.75 | 1 | 0.46 |
| 15 | 0.77 | 0.6 | 0.82 | 0.59 | 1 | 0.33 |
| 16 | 0.7 | 0.97 | 0.45 | 0.74 | 0.97 | 0.5 |
| 17 | 0.8 | 1 | 0.54 | 0.81 | 0.97 | 0.6 |
| 18 | 0.68 | 0.95 | 0.42 | 0.61 | 1 | 0.39 |
| 19 | 0.68 | 1 | 0.44 | 0.63 | 0.95 | 0.41 |
| 20 | 0.83 | 0.66 | 0.85 | 0.7 | 0.94 | 0.59 |
| Ave | 0.74 | 0.86 | 0.58 | 0.69 | 0.89 | 0.52 |

With a total 244 sample size of Case-control study for stroke disease, including 122 samples are control and 122 samples are strokes. We applied supervised penalized logistic regression method to extract significant texture-related features from total 32 texture features. Five of significant features such as normalized Homogeneity (nHo), Entropy (nEnt), Contrast (nCo), $4^{th}$ moment (nm4) (from GLCM features) and Run percentage (nRunPer) (from RLM features) that are extracted. The validation of classification based on Random Forest is given and the accuracy is measured by the area under the ROC curve which is about 0.74 with sensitivity and specificity of 0.86 and 0.58 respectively. This is considered as a quite fair accuracy for classification of stroke.

Similarly procedure we worked on high order spectra analysis and obtained the AUC is about 0.69 with sensitivity and specificity of 0.89 and 0.52, which is close to the fair accuracy for classification of stroke. The significant features (from total 52 features) are given as follows:

"e1r6" indicated Entropy1 HOS features at degree of 100

"e2r9" indicated Entropy2 HOS features at degree of 160

"e3r3" indicated Entropy3 HOS features at degree of 40

"e3r8" indicated Entropy3 HOS features at degree of 140

"e3r9" indicated Entropy3 HOS features at degree of 160

"ePRes3" indicated Entropy Phase HOS features at degree of 40

"ePRes8" indicated Entropy Phase HOS features at degree of 140

"ePRes9" indicated Entropy Phase HOS features at degree of 160

"ePRes10" indicated Entropy Phase HOS features at degree of 180

"amRes1" indicated Entropy Magnitude HOS features at degree of 0
"amRes2" indicated Entropy Magnitude HOS features at degree of 20
"amRes3" indicated Entropy Magnitude HOS features at degree of 40
"amRes4" indicated Entropy Magnitude HOS features at degree of 60
"amRes6" indicated Entropy Magnitude HOS features at degree of 100
"amRes7" indicated Entropy Magnitude HOS features at degree of 120
"amRes8" indicated Entropy Magnitude HOS features at degree of 140
"amRes9" indicated Entropy Magnitude HOS features at degree of 160
"amRes10" indicated Entropy Magnitude HOS features at degree of 180

The following tables provide the results for the association between computer-generated factors from texture analysis and clinical screening factors.

a) Significant Associations Between Continuous Variables (Factors) and Clinical Screening Factors

TABLE 10

SIGNIFICANT ASSOCIATIONS (CORRELATION COEFFICIENT) BETWEEN FACTORS GENERATED FROM TEXTURE ANALYSIS AND CLINICAL SCREENING FACTORS:

| Factors | NadjustedCRAE (p-value) | MVasmmetry (p-value) | vasNaCRAE (p-value) | vasTortuosity (p-value) | HemoNaCRAE (p-value) |
|---|---|---|---|---|---|
| cshad | −.371**(<.001) | −.211**(.002) | −.419**(<.001) | — | .243**(<.001) |
| savgh | .288**(<.001) | .233**(<.001) | .373**(<.001) | −.185**(.005) | −.158*(.016) |
| nHo | −.333**(<.001) | −.279**(<.001) | −.434**(<.001) | .147*(.026) | .211**(.001) |
| nEnt | .338**(<.001) | .252**(<.001) | .423**(<.001) | −.136*(.040) | −.213**(.001) |
| nCo | .342**(<.001) | .259**(<.001) | .432**(<.001) | −.145*(.028) | −.217**(.001) |
| nm4 | .336**(<.001) | .242**(<.001) | .418**(<.001) | −.134*(.042) | −.211**(.001) |
| nRunPer | .337**(<.001) | .251**(<.001) | .425**(<.001) | −.138*(.037) | −.202**(.002) |

*Correlation is significant at the 0.05 level (2-tailed).
**Correlation is significant at the 0.01 level (2-tailed).

TABLE 11

SIGNIFICANT ASSOCIATIONS (CORRELATION) BETWEEN FACTORS GENERATED FROM HOS ANALYSIS AND CLINICAL SCREENING FACTORS:

| Factors | NadjustedCRAE (p-value) | vasNaCRAE (p-value) | vasTortuosity (p-value) | HemoNaCRAE (p-value) |
|---|---|---|---|---|
| e1r6 | −.152*(.025) | — | — | .243**(<.001) |
| e3r9 | .151*(.025) | .146*(.033) | −.185**(.005) | −.132*(.046) |
| ePRes8 | — | −.148*(.031) | — | — |
| ePRes9 | .195**(.004) | — | .147*(.026) | — |
| ePRes10 | .205**(.002) | .153*(.026) | −.136*(.040) | — |
| amRes1 | — | — | −.192**(.004) | — |
| amRes2 | — | — | −.174**(.008) | — |
| amRes3 | −.155*(.021) | — | −.145*(.028) | — |
| amRes4 | −.137*(.043) | — | −.134*(.042) | — |
| amRes6 | — | .138*(.044) | −.139*(.035) | — |
| amRes7 | −.148*(.029) | — | — | .143*(.030) |
| amRes8 | −.179**(008) | — | — | — |
| amRes9 | −.212**(.002) | .— | −.162*(.014) | — |
| amRes10 | — | — | −.156*(.018) | — |

*Correlation is significant at the 0.05 level (2-tailed).
**Correlation is significant at the 0.01 level (2-tailed).

b) Significant Associations Between Categorical Variables (Factors) and Clinical Screening Factors

TABLE 12

SIGNIFICANT ASSOCIATIONS (LOGISTIC REGRESSION) BETWEEN FACTORS GENERATED FROM TEXTURE ANALYSIS AND CLINICAL SCREENING FACTORS:

| Factors | AF p-value | Hypertension p-value | Hemorrhage* p-value | DM* p-value | tortuosity0_1 p-value | nipping p-value |
|---|---|---|---|---|---|---|
| cshad | .020 | — | .001 | <.001 | — | — |
| savgh | — | .023 | .009 | <.001 | .027 | — |
| nHo | — | .028 | .001 | <.001 | — | — |
| nEnt | — | — | .011 | <.001 | .042 | .086 |
| nCo | — | .036 | .004 | <.001 | .048 | — |

TABLE 12-continued

SIGNIFICANT ASSOCIATIONS (LOGISTIC REGRESSION) BETWEEN FACTORS GENERATED FROM TEXTURE ANALYSIS AND CLINICAL SCREENING FACTORS:

| Factors | AF p-value | Hypertension p-value | Hemorrhage* p-value | DM* p-value | tortuosity0_1 p-value | nipping p-value |
|---|---|---|---|---|---|---|
| nm4 | — | — | .031 | <.001 | .045 | — |
| nRunPer | — | .010 | .002 | <.001 | — | — |

*Introduction in next $2^{nd}$ part

TABLE 13

SIGNIFICANT ASSOCIATIONS (LOGISTIC REGRESSION) BETWEEN FACTORS GENERATED FROM HOS ANALYSIS AND CLINICAL SCREENING FACTORS:

| Factors | AF p-value (or ODD) | Hemorrhage* p-value (or ODD) | DM* p-value (or ODD) | tortuosity0_1 p-value (or ODD) |
|---|---|---|---|---|
| e3r9 | | | .017 | — |
| ePRes8 | | .025 | | |
| ePRes10 | .036 | | | |
| amRes1 | | | | .006 |
| amRes6 | | .037 | <.001 | |
| amRes7 | | .011 | <.001 | |
| amRes8 | | | | .070 (28.672) |

*Introduction in next $2^{nd}$ part

Fractal Analysis

Fractals are objects with irregular, auto-similar features, with details that can be noticed at any scale of representation. Biofractals are the fractal textures/contours in biology (tissues, neurons, leaves, etc.). The similarity between fractals and the natural objects suggests that fractal properties, such as fractal dimension, may be used as a classifier in biology. Since many natural phenomena are so complicated and irregular that they cannot be modeled well using traditional classical techniques. Those irregular sets and functions can be regarded as a class to which a general theory can be applicable, known as 'Fractal geometry'. This class represents many natural phenomena much better than figures of classical geometry do and theory provides us with the concepts and practical techniques needed for the analysis of these phenomena[164]. Many studies have been proposed that retinal vessels are fractal and that fractal analysis could be applied in automated diagnosis for retinal diseases. Some of related studies are proposed[165-173]. In many studies, the Box-counting method has been largely used to estimate fractal dimensions of measures, but this procedure has been pointed out as problematic due to memory and time limitation (Hou et al., 1990). It definitely will cause the problem when used in automatic computer system to detect stroke signs. Traditionally, vascular patterns have been described using variety of simple measures, including the mean diameter of vessels, mean length of vessel segments, branch angle, vessel area density (the fraction of image area occupied by the vessels), and vessel length density (the fraction of image area occupied by the skeleton of the vessels).

The recent study for Fractal Analysis of the Retinal Vasculature is proposed by Azemin M. Z., Kumar D. K., Wong T. Y., and et al.[165]] They proposed the method of Fourier Fractal dimension on these preprocessed images and do not require any segmentation of the vessels. This method can be used to extract the complexity of the retinal vasculature enhanced at different wavelet scales and a model was formulated for stroke prediction[174].

Based on the spirit of this approach and the advantage of wavelet transform over Fourier transform on multiscale analysis (Wavelets often give a better signal/information representation using Multiresolution analysis, with balanced resolution at any time and frequency). In this project we have used two approaches to work on stroke prediction problem. One is based on qualified enhancing gray-level image to apply the wavelet-based fractal analysis to extract the most important features to detect stroke. The technique we used is complex wavelet Leader multifractal analysis, since wavelet Leader multifractal analysis (WLMF) allows us to perform an accurate, complete and low computational and memory costs multifractal characterization of textures in images[176]. The other approach is to apply multifractal spectrum (MFS). This method can provide an efficient framework combining global spatial invariance and local robust measurements[177]. Besides these, some parameters of monofractal analysis will also be generated. Overall, all fractal analysis related parameters will be integrated and to classify the stroke cases. Finally, the important (significant) factors will be gained (also see FIG. 3).

Remarks: Fractal analysis related parameters will be used in the detection of vascular change as a result of conditions such as stroke disease. At previous stage we mainly use three fractal parameters: average intercepts and average slope (dimension) determined from all 24 directions of retinal gray level enhanced image (Fourier Fractal dimension technique is used). Also, the parameter of Hausdorff dimension is in a similar way determined as in above two parameters except it applies in a binary image for vessels. In the future study, we will apply more advanced and accurate method based on the above mentioned wavelet techniques.

Similar to the above Case-control study with texture analysis with HOS for stroke disease, the supervised penalized logistic regression method is used to extract significant features from fractal-texture combined features. Three of the significant features such as Hausdorff dimension (Hdfdimension) from binary retinal image of vessels, Sum average (savgh) and Cluster Shade (cshad) are extracted. The validation results using the classification based on Random Forest is given and the accuracy is measured by the area under the ROC curve, which is about 0.755 with standard deviation of 0.039 (see Table 14, third column). This is considered as a quite fair accuracy for classification of stroke. See the following Table 14.

TABLE 14

AFTER 20 RUNS (RANDOM SAMPLED BY 70% AS TRAINING DATASET AND 30% AS TESTED DATASET) OF RANDOM FOREST CLASSIFICATION, WE HAVE THE SUMMARY FOR THE ROC RESULTS FROM FRACTAL ANALYSIS:

| | Fractal-detected features | | |
|---|---|---|---|
| t | AUC | sens | specs |
| 1 | 0.81 | 0.95 | 0.59 |
| 2 | 0.75 | 0.9 | 0.51 |
| 3 | 0.65 | 1 | 0.39 |
| 4 | 0.73 | 0.47 | 0.89 |
| 5 | 0.73 | 1 | 0.33 |
| 6 | 0.78 | 0.73 | 0.78 |
| 7 | 0.77 | 0.8 | 0.64 |
| 8 | 0.82 | 0.79 | 0.73 |
| 9 | 0.79 | 0.89 | 0.61 |
| 10 | 0.81 | 0.84 | 0.76 |
| 11 | 0.75 | 1 | 0.49 |
| 12 | 0.75 | 0.74 | 0.69 |
| 13 | 0.75 | 0.9 | 0.57 |
| 14 | 0.8 | 0.95 | 0.54 |
| 15 | 0.73 | 0.43 | 0.95 |
| 16 | 0.81 | 0.86 | 0.71 |
| 17 | 0.82 | 0.92 | 0.66 |
| 18 | 0.73 | 0.97 | 0.42 |
| 19 | 0.72 | 1 | 0.41 |
| 20 | 0.85 | 0.83 | 0.77 |
| Ave | 0.77 | 0.85 | 0.62 |

The following tables are the results of the association between computer-generated factors and clinical screening factors Part I: Association Between Continuous Variables (Factors) and Clinical Screening Factors

TABLE 15

SIGNIFICANT ASSOCIATIONS (CORRELATION COEFFICIENT) BETWEEN FACTORS GENERATED FROM FRACTAL ANALYSIS AND CLINICAL SCREENING FACTORS

| Factors | NadjustedCRAE (p-value) | MVasmmetry (p-value) | vasNaCRAE (p-value) | HemoNaCRAE (p-value) |
|---|---|---|---|---|
| Hdfdimension | .320**(<.001) | .221**(.001) | .384**(<.001) | −.188**(.004) |
| minfq | −.325**(<.001) | −.227**(.001) | | |

*Correlation is significant at the 0.05 level (2-tailed).
**Correlation is significant at the 0.01 level (2-tailed).

TABLE 16

SIGNIFICANT ASSOCIATION (LOGISTIC REGRESSION) BETWEEN FACTORS GENERATED FROM FRACTAL ANALYSIS AND CLINICAL SCREENING FACTORS

| Factors | AF p-value | Hypertension p-value | Hemorrhage* p-value | DM* p-value | Tortuosity0_1 p-value | Nipping p-value |
|---|---|---|---|---|---|---|
| Hdfdimension | .011 | .001 | .003 | <.001 | | |
| minfq | | .027 | .058 | <.001 | .042 | .104 |

*Introduction in next part

Other Stroke Features that Related to Diabetic Retinopathy: Hemorrhages

We will adopt the Hemorrhages extraction method in previous DR project. This is part of vessel features stated in FIG. 4. Notice that the measurement of Hemorrhages can be either present/absent or the area calculated in pixels.

Remark: the purpose of above procedure is to generate significant factors associate with stroke based on fractal analysis. Similarly for texture properties, instead of generating fractal analysis factors (fractal dimension, slope, intercept and etc.), we generate texture features such as GLCM/GLDM features and high-order spectral related factors that highly correlate to stroke. Finally we integrate all significant factors/parameters from sections 3.2 to 3.5 and apply the Random Forest combined with generalized linear model (GLM) to work on the diagnosis of stroke. Overall, our new proposed features will cover much more useful information compare to previous studies.

We combined all three approaches using all the extracted features and applied supervised penalized logistic regression and Random Forest classification. The results show that the automated computer system using all features except DR features already has a very high AUC under ROC curve, and have high sensitivity. However, the specificity is low. When automatic computer system using all features including DR features the AUC of ROC curve achieves on average 0.88 with a sensitivity of 0.89 and specificity of 0.76. (Table 17)

TABLE 17

AFTER 40 RUNS (RANDOM SAMPLED BY 70% AS TRAINING DATASET AND 30% AS TESTED DATASET) OF RANDOM FOREST CLASSIFICATION, WE HAVE THE SUMMARY FOR THE ROC RESULTS:

Comparison between Screening methods (LQ's approach) and our Automatic system approach

| t | Manual Retinal features (Screening) | | | Manual Retinal & Clinical features (Screening) | | | Auto without DR features (Auto) | | | Auto includes DR features (Auto) | | |
|---|---|---|---|---|---|---|---|---|---|---|---|---|
| | AUC | sens | specs | AUC | sens | specs | AUC | sens | specs | AUC | sens | specs |
| 1 | 0.55 | 0.7 | 0.5 | 0.73 | 0.89 | 0.54 | 0.8 | 0.95 | 0.49 | 0.9 | 0.88 | 0.81 |
| 2 | 0.74 | 0.58 | 0.86 | 0.78 | 0.76 | 0.79 | 0.83 | 1 | 0.51 | 0.91 | 0.82 | 0.9 |
| 3 | 0.77 | 0.75 | 0.77 | 0.76 | 0.73 | 0.83 | 0.83 | 1 | 0.47 | 0.91 | 0.93 | 0.81 |
| 4 | 0.7 | 0.73 | 0.69 | 0.63 | 0.44 | 0.83 | 0.74 | 0.97 | 0.34 | 0.85 | 0.89 | 0.68 |
| 5 | 0.86 | 0.75 | 0.97 | 0.78 | 0.85 | 0.77 | 0.83 | 0.92 | 0.55 | 0.91 | 0.9 | 0.78 |
| 6 | 0.7 | 0.76 | 0.66 | 0.76 | 0.91 | 0.55 | 0.78 | 0.97 | 0.41 | 0.85 | 0.86 | 0.71 |
| 7 | 0.74 | 0.76 | 0.76 | 0.77 | 0.8 | 0.7 | 0.73 | 0.98 | 0.37 | 0.86 | 0.77 | 0.84 |
| 8 | 0.83 | 0.7 | 0.88 | 0.8 | 0.87 | 0.66 | 0.83 | 0.8 | 0.79 | 0.85 | 0.91 | 0.7 |
| 9 | 0.71 | 0.91 | 0.45 | 0.67 | 0.82 | 0.57 | 0.85 | 0.95 | 0.57 | 0.85 | 0.95 | 0.59 |
| 10 | 0.73 | 0.78 | 0.72 | 0.71 | 0.74 | 0.68 | 0.82 | 0.98 | 0.49 | 0.87 | 0.97 | 0.65 |
| 11 | 0.74 | 0.64 | 0.79 | 0.74 | 0.7 | 0.82 | 0.78 | 0.98 | 0.42 | 0.9 | 0.82 | 0.87 |
| 12 | 0.79 | 0.92 | 0.6 | 0.75 | 0.82 | 0.63 | 0.81 | 0.98 | 0.43 | 0.89 | 0.9 | 0.74 |
| 13 | 0.76 | 0.79 | 0.7 | 0.77 | 0.82 | 0.64 | 0.83 | 0.95 | 0.53 | 0.88 | 0.9 | 0.71 |
| 14 | 0.72 | 0.71 | 0.74 | 0.68 | 0.67 | 0.73 | 0.82 | 1 | 0.43 | 0.93 | 0.92 | 0.85 |
| 15 | 0.77 | 0.82 | 0.72 | 0.73 | 0.84 | 0.66 | 0.81 | 0.94 | 0.58 | 0.92 | 0.88 | 0.89 |
| 16 | 0.75 | 0.84 | 0.62 | 0.7 | 0.71 | 0.71 | 0.81 | 0.97 | 0.42 | 0.89 | 0.92 | 0.77 |
| 17 | 0.77 | 0.74 | 0.84 | 0.8 | 0.69 | 0.87 | 0.81 | 1 | 0.49 | 0.9 | 0.86 | 0.83 |
| 18 | 0.74 | 0.75 | 0.73 | 0.74 | 0.76 | 0.72 | 0.87 | 1 | 0.61 | 0.9 | 0.88 | 0.81 |
| 19 | 0.78 | 0.78 | 0.82 | 0.71 | 0.73 | 0.73 | 0.81 | 1 | 0.43 | 0.9 | 0.84 | 0.78 |
| 20 | 0.66 | 0.79 | 0.68 | 0.67 | 0.78 | 0.59 | 0.83 | 0.95 | 0.53 | 0.93 | 0.86 | 0.87 |
| 21 | 0.71 | 0.83 | 0.58 | 0.8 | 0.75 | 0.74 | 0.85 | 0.91 | 0.63 | 0.91 | 0.95 | 0.79 |
| 22 | 0.71 | 0.74 | 0.72 | 0.72 | 0.72 | 0.71 | 0.84 | 0.97 | 0.57 | 0.84 | 0.97 | 0.63 |
| 23 | 0.7 | 0.64 | 0.77 | 0.83 | 0.88 | 0.73 | 0.86 | 1 | 0.43 | 0.85 | 0.85 | 0.74 |
| 24 | 0.85 | 0.8 | 0.9 | 0.86 | 0.84 | 0.84 | 0.82 | 1 | 0.44 | 0.9 | 0.82 | 0.85 |
| 25 | 0.68 | 0.84 | 0.59 | 0.66 | 0.79 | 0.62 | 0.83 | 1 | 0.47 | 0.88 | 0.83 | 0.76 |
| 26 | 0.79 | 0.76 | 0.76 | 0.72 | 0.8 | 0.71 | 0.73 | 1 | 0.29 | 0.86 | 0.83 | 0.8 |
| 27 | 0.66 | 0.68 | 0.66 | 0.67 | 0.58 | 0.84 | 0.84 | 1 | 0.54 | 0.86 | 0.88 | 0.76 |
| 28 | 0.72 | 0.74 | 0.65 | 0.7 | 0.66 | 0.77 | 0.76 | 0.98 | 0.44 | 0.84 | 0.93 | 0.6 |
| 29 | 0.72 | 0.74 | 0.78 | 0.75 | 0.76 | 0.73 | 0.79 | 1 | 0.4 | 0.89 | 0.92 | 0.74 |
| 30 | 0.7 | 0.61 | 0.79 | 0.73 | 0.7 | 0.82 | 0.75 | 1 | 0.33 | 0.84 | 0.83 | 0.77 |
| 31 | 0.7 | 0.67 | 0.76 | 0.84 | 0.77 | 0.88 | 0.78 | 1 | 0.46 | 0.91 | 0.95 | 0.7 |
| 32 | 0.72 | 0.77 | 0.67 | 0.76 | 0.89 | 0.62 | 0.85 | 0.94 | 0.61 | 0.93 | 0.89 | 0.9 |
| 33 | 0.74 | 0.61 | 0.82 | 0.81 | 0.67 | 0.85 | 0.81 | 0.84 | 0.69 | 0.8 | 0.9 | 0.51 |
| 34 | 0.74 | 0.75 | 0.71 | 0.75 | 0.79 | 0.65 | 0.84 | 0.98 | 0.49 | 0.91 | 0.81 | 0.89 |
| 35 | 0.73 | 0.74 | 0.79 | 0.75 | 0.72 | 0.81 | 0.82 | 0.95 | 0.53 | 0.87 | 0.95 | 0.68 |
| 36 | 0.72 | 0.66 | 0.74 | 0.76 | 0.76 | 0.82 | 0.77 | 1 | 0.39 | 0.84 | 0.91 | 0.58 |
| 37 | 0.74 | 0.7 | 0.79 | 0.8 | 0.81 | 0.77 | 0.8 | 1 | 0.45 | 0.88 | 0.92 | 0.71 |
| 38 | 0.71 | 0.62 | 0.81 | 0.72 | 0.61 | 0.81 | 0.81 | 0.94 | 0.56 | 0.84 | 0.91 | 0.64 |
| 39 | 0.66 | 0.61 | 0.83 | 0.68 | 0.68 | 0.71 | 0.81 | 1 | 0.55 | 0.9 | 0.93 | 0.76 |
| 40 | 0.69 | 0.71 | 0.65 | 0.73 | 0.76 | 0.77 | 0.83 | 1 | 0.58 | 0.88 | 0.88 | 0.78 |
| AVE | 0.73 | 0.73 | 0.73 | 0.74 | 0.76 | 0.73 | 0.81 | 0.97 | 0.49 | 0.88 | 0.89 | 0.76 |

Manual Retinal features—Results using manual method on retinal images alone
Manual Retinal and Clinical features—Results using manual method on retinal images and clinical parameters
Auto without DR features (Auto)—Automatic computer method using Stroke characteristics without DR parameters
Auto includes DR features (Auto)—Automatic computer method using Stroke characteristics include DR parameters The significant features extracted without hemorrhage (See Auto-detected features A1) are: e3r3, e3r9, ePRes10, amRes1, amRes7, amRes9, Hausdorff dimension from binary retinal image of vessels and normalized Homogeneity. With hemorrhage and DM involving, we have the AUC=0.858, which has a comparable the most accuracy result. The significant features extracted are: e3r9, amRes2, amRes9, Hausdorff dimension from binary retinal image of vessels, normalized Homogeneity, normalized $4^{th}$ moment, hemorrhage and Diabetes.

Conclusion

We have reviewed the background information on using retinal images as risk assessment tools for predicting stroke. There is strong scientific rationale of the relationship of vascular circulation on the relationship between retina and brain where it is likely that stroke can be predicted by observing the retinal images. We have already tackled the automation problem using retinal images for diabetic retinopathy. A similar approach is now extended to this application including novel characteristics determined specifically for stroke, for example, vessel bifurcation, vascular bifurcation angles, vascular tortuosity and number of vessel branches.

We have also carried out manual assessment to evaluate the concept of using manually quantified parameters for the detection of stroke using existing and novel parameters we developed. The results of the case-control study using retinal assessment alone have an AUC value of 0.73 under the ROC curve. The sensitivity is about 0.73 with a specificity of 0.73. Including the clinical information, the sensitivity was increased to 0.76.

The automatic computer method we developed in this project included image quality assessment process. The program will then process four components of analyses, including blood vessels parameters, texture approach, fractal analysis, and diabetic retinopathy related parameters. With the information extracted from the program, a classification is then performed to evaluate if the patient is likely to have a stroke. We used the case-control study data for validation. The results using just the stroke characteristics determined in this project have an AUC value of 0.81, with a sensitivity of 0.97 and a specificity of 0.49. However, if we included the diabetic retinopathy parameters the AUC value increased to 0.88, with a sensitivity of 0.89 and specificity of 0.76.

Since the random forest method is a more conservative, we also carried out the SPSS cross-validation analysis as a comparison to the manual classification. The AUC for the automatic detection is 0.92 (95% confidence interval from 0.89 to 0.95), with a sensitivity of 0.83 and a specificity of 0.84 (FIG. 9).

EXAMPLE 3

Screening or Grading of Diabetic Retinopathy

Materials and Methods

Public dataset "DIARETDB0" (Kauppi, T., et. al, *DIARETDB0: Evaluation Database and Methodology for Diabetic Retinopathy Algorithms*. Technical report) is used to train the system of the application. This database consists of 130 color retina images of which 20 are normal and 110 contain signs of the diabetic retinopathy. Characteristics of the dataset are summarized in Table 18. "redsmalldots", "hemorrhages", "hardexudates", "softexudates" and "neovascularisation" represent "microaneurysms", "hemorrhages", "hard exudates", "cotton wool spots" and "new vessels" respectively.

TABLE 18

CHARACTERISTIC SUMMARIES OF DATASET "DIARETDB0"

| Characteristics | redsmalldots | hemorrhages | Hardexudates | softexudates | Neovascularisation |
|---|---|---|---|---|---|
| Number | 106 | 80 | 73 | 41 | 20 |

In the system utilized in the Example, the first module is digital fundus camera integrated to other modules, the second module is configured to conduct color histogram and dual tree complex wavelet transform (DTCWT) analysis, and the seven module for analyzing texture and the units comprised in the fourth module for exudates and hemorrhage detection are configured to conduct a wavelet-based Radon transform and 3rd order spectral analysis; and the unit comprised in the fourth module for new vessels detection is configured to conduct DTCWT and 3rd order spectral analysis.

For testing the accuracy of the system, the accuracy of detection of hemorrhage or exudates is determined with the given results of the dataset as reference. For testing the accuracy of DR grading, 110 retina images without new vessels are used to determine whether the system can classify hemorrhage and exudates into three severity grading with the grading criteria in Early Treatment Diabetic Retinopathy Study (ETDRS) as reference (see the following list).

Grading Criteria of Severity of Diabetic Retinopathy by Ophthalmologist a. Grading of Severity of Hemorrhages Grade one: hemorrhages less or equal to standard photograph 1 in ETDRS.

Grade two: hemorrhages less or equal to standard photograph 2, but more than standard photograph 1 in ETDRS.

Grade three: hemorrhages more than standard photograph 2.

b. Grading of Severity of Exudates

Grade one: exudates less than standard photograph 3 in ETDRS.

Grade two: exudates equal or more than standard photograph 3, and less than standard photograph 4 in ETDRS.

Grade three: exudates more than standard photograph 4 in ETDRS.

The system was also tested for the accuracy of grading of DR into grade one to grade three as described above. The 20 retina images with "new vessels" were used to test whether the system can detect new vessels accurately.

Student t-test/ANOVA will be used as significance test and ROC curve with accuracy, sensitivity, specificity will be used as validation test.

Results

Exudates Detection

All 130 retina images in the dataset are used to test the sensitivity and specificity of exudates detection by the above system. The sensitivity and specificity are 97.18% and 89.83% respectively. The accuracy is 93.85%. (Table 19)

TABLE 19

THE SENSITIVITY, SPECIFICITY AND ACCURACY OF EXUDATES DETECTION.

| | Positive (Normal) | Negative (Abnormal) | |
|---|---|---|---|
| Positive (Normal) | TP = 69 | FP = 6 | TPR = 69/75 = 92% |
| Negative (Abnormal) | FN = 2 | TN = 53 | FPR = 53/55 = 96.36% |

TABLE 19-continued

THE SENSITIVITY, SPECIFICITY AND ACCURACY OF EXUDATES DETECTION.

| | Positive (Normal) | Negative (Abnormal) | |
|---|---|---|---|
| AUC = 70.8% | Sensitivity = 69/71 = 97.18% | Specificity = 53/59 = 89.83% | Accuracy: 122/130 = 93.85% (TP + TN)/(P + N) |

Severity of Exudates

In the 110 retina images without new vessels, there are 61 images, 44 images, and 5 images in grade one, grade two, and grade three respectively in the severity of exudates graded by ophthalmologists. The above system detected the area in pixels of the exudates in each group (Table 20). There is a statistical significant difference in area among the three groups, F=9.638, P<0.001. And there is a statistical significant difference in area between group three and group one (P<0.001), group three and group two (P=0.005). The difference between group one and group two is not statistically significant at 0.05 level, P=0.162 (Table 21).

TABLE 20

AREA OF EXUDATES DETECTED IN EACH GRADE.

| Grade | Number | Mean (pixels) | SD |
|---|---|---|---|
| 0 | 61 | 101.8 | 580.5 |
| 1 | 44 | 380.1 | 879.0 |
| 2 | 5 | 1539 | 965.7 |
| Total | 110 | 278.4 | 786.8 |

TABLE 21

MULTIPLE COMPARISON OF AREA (PIXELS) BETWEEN THREE GRADING OF EXUDATES SEVERITY.

| (I) exudate grading | (J) exudate grading | Mean Difference (I-J) | Std. Error | Sig. | 95% Confidence Interval | |
|---|---|---|---|---|---|---|
| | | | | | Lower Bound | Upper Bound |
| 1 | 2 | −278.3 | 144.6 | 0.162 | −637.2 | 80.65 |
| | 3 | −1437* | 340.0 | 0.000 | −2281 | −592.9 |
| 2 | 1 | 278.3 | 144.6 | 0.162 | −80.65 | 637.2 |
| | 3 | −1158* | 345.0 | 0.005 | −2015 | −302.4 |
| 3 | 1 | 1437* | 340.0 | 0.000 | 592.9 | 2281 |
| | 2 | 1159* | 345.0 | 0.005 | 302.4 | 2015 |

The mean difference is significant at the 0.05 level.

Hemorrhage Detection

All 130 retina images in the dataset are used to test the sensitivity and specificity of hemorrhage detection by the system as described in the section "Materials and Methods". The sensitivity and specificity are 98.78% and 85.42% respectively. And the accuracy is 93.85%. (Table 22)

TABLE 22

THE SENSITIVITY, SPECIFICITY AND ACCURACY OF HEMORRHAGES DETECTION.

| | Positive (Normal) | Negative (Abnormal) | |
|---|---|---|---|
| Positive (Normal) | TP = 81 | FP = 7 | TPR = 81/88 = 92.05% |
| Negative (Abnormal) | FN = 1 | TN = 41 | FPR = 41/42 = 97.62% |
| AUC = 70.8% | Sensitivity = 81/82 = 98.78% | Specificity = 41/48 = 85.42% | Accuracy: 122/130 = 93.85% (TP + TN)/(P + N) |

Severity of Hemorrhages

In the 110 retina images without new vessels, there are 63 images, 33 images, and 14 images in grade one, grade two, and grade three respectively in the severity of hemorrhages graded by ophthalmologist. The above system detected the area in pixels of the hemorrhages in each group (Table 23). There is statistical significant difference in area among the three groups, F=15.179, P<0.001. And there is statistical significant difference in area between group three and group one (P<0.001), group three and group two (P=0.001). The difference between group one and group two is not statistically significant at 0.05 level, P=0.201 (Table 24).

TABLE 23

AREA OF HEMORRHAGES DETECTED IN EACH GRADE.

| | N | Mean | SD |
|---|---|---|---|
| 1 | 63 | 2484 | 1956 |
| 2 | 33 | 3326 | 2250 |
| 3 | 14 | 6005 | 2835 |
| Total | 110 | 3185 | 2435 |

TABLE 24

MULTIPLE COMPARISON OF AREA (PIXELS) BETWEEN THREE GRADING OF HEMORRHAGE SEVERITY.

| (I) hemo grading 3 levels | (J) hemo grading 3 levels | Mean Difference (I-J) | Std. Error | Sig. | 95% Confidence Interval | |
|---|---|---|---|---|---|---|
| | | | | | Lower Bound | Upper Bound |
| 1 | 2 | −842.0 | 466.2 | 0.201 | −1999 | 315.4 |
| | 3 | −3521* | 641.1 | 0.000 | −5112 | −1929 |
| 2 | 1 | 842.0 | 466.2 | 0.201 | −315.4 | 1999 |
| | 3 | −2679* | 692.0 | 0.001 | −4397 | −960.6 |
| 3 | 1 | 3521* | 641.1 | 0.000 | 1929 | 5112 |
| | 2 | 2679* | 692.0 | 0.001 | 960.6 | 4397 |

*The mean difference is significant at the 0.05 level.

Automatic Classification of Non-Proliferative Diabetic Retinopathy

Referring to the grading criteria of American Association of Ophthalmology, retina images without new vessels (110 images) are graded by the above system into three grades, where 58 in grade one, 33 in grade two, and 19 in grade three. In the univariate analysis, area of exudates and hemorrhages, texture of the image including third moment and high spectrum entropy (ep1, ep2, ep4) are significantly different among the three grades (Table 25 and Table 26).

TABLE 25

DESCRIPTION OF THIRD MOMENT, HEMORRHAGE AREA, AND EXUDATES AREA IN THREE GRADES.

| | | N | Mean | SD | SE | 95% Confidence Interval for Mean | | Minimum | Maximum |
|---|---|---|---|---|---|---|---|---|---|
| | | | | | | Lower Bound | Upper Bound | | |
| Third Moment | 1 | 58 | −0.4696 | 0.5453 | 0.07160 | −0.6129 | −0.3262 | −1.041 | 1.199 |
| | 2 | 33 | −0.7297 | 0.1883 | 0.03278 | −0.7965 | −0.6630 | −1.047 | −0.2268 |

TABLE 25-continued

DESCRIPTION OF THIRD MOMENT, HEMORRHAGE AREA, AND EXUDATES AREA IN THREE GRADES.

|  |  | N | Mean | SD | SE | 95% Confidence Interval for Mean | | Minimum | Maximum |
|---|---|---|---|---|---|---|---|---|---|
|  |  |  |  |  |  | Lower Bound | Upper Bound |  |  |
|  | 3 | 19 | −0.6507 | 0.4006 | 0.09191 | −0.8439 | −0.4577 | −0.9750 | 0.8401 |
|  | Total | 110 | −0.5789 | 0.4545 | 0.04333 | −0.6648 | −0.4931 | −1.047 | 1.199 |
| Hemorrhage area | 1 | 58 | 2441 | 1903 | 249.9 | 1940 | 2941 | 67 | 9158 |
|  | 2 | 33 | 3002 | 2005 | 349.0 | 2291 | 3713 | 648 | 10814 |
|  | 3 | 19 | 5773 | 2895 | 664.2 | 4378 | 7169 | 1390 | 11706 |
|  | Total | 110 | 3185 | 2435 | 232.2 | 2724 | 3645 | 67 | 11706 |
| Exudates area | 1 | 58 | 81.62 | 561.4 | 73.72 | −66.01 | 229.2 | 0 | 4279 |
|  | 2 | 33 | 603.4 | 1114 | 194.1 | 208.1 | 998.7 | 0 | 4338 |
|  | 3 | 19 | 314.7 | 469.6 | 107.7 | 88.36 | 541.1 | 0 | 1788 |
|  | Total | 110 | 278.4 | 786.7 | 75.02 | 129.8 | 427.1 | 0 | 4338 |

TABLE 26

COMPARISON OF DIFFERENCE OF THIRD MOMENT, ENTROPY, HEMORRHAGE AND EXUDATES AREA AMONG THREE GRADES.

|  |  | Sum of Squares | df | Mean Square | F | Sig. |
|---|---|---|---|---|---|---|
| Third Moment | Between Groups | 1.542 | 2 | 0.771 | 3.933 | 0.022 |
|  | Within Groups | 20.97 | 107 | 0.196 |  |  |
|  | Total | 22.51 | 109 |  |  |  |
| Ep1 | Between Groups | 0.027 | 2 | 0.013 | 3.100 | 0.049 |
|  | Within Groups | 0.467 | 107 | 0.004 |  |  |
|  | Total | 0.494 | 109 |  |  |  |
| Ep2 | Between Groups | 0.125 | 2 | 0.062 | 3.578 | 0.031 |
|  | Within Groups | 1.878 | 107 | 0.017 |  |  |
|  | Total | 2.004 | 109 |  |  |  |
| Ep4 | Between Groups | 0.262 | 2 | 0.131 | 3.995 | 0.021 |
|  | Within Groups | 3.520 | 107 | 0.0328 |  |  |
|  | Total | 3.783 | 109 |  |  |  |
| Hemorrhage area | Between Groups | $1.605 * 10^8$ | 2 | $8.026 * 10^7$ | 17.67 | 0.000 |
|  | Within Groups | $4.861 * 10^8$ | 107 | $4.543 * 10^6$ |  |  |
|  | Total | $6.466 * 10^8$ | 109 |  |  |  |
| Exudate area | Between Groups | $5.757 * 10^6$ | 2 | $2.879 * 10^6$ | 4.991 | 0.008 |
|  | Within Groups | $6.172 * 10^7$ | 107 | $5.768 * 10^5$ |  |  |
|  | Total | $6.747 * 10^7$ | 109 |  |  |  |

Validation 55 retina images were randomly selected as training group to train neural network and the other 55 retina images were used to test the accuracy. The above steps were repeated 20 times. The mean of accuracy is 97.2%.

New Vessels Detection

The key feature of proliferative diabetic retinopathy (PDR) is the existence of new vessels. The system as described in the section "Materials and Methods" was used to detect normal retina image and retina image with new vessel.

The results obtained by the system demonstrate that retina image with new vessel exhibits curl small new vessels on optic disc, which is distinctly different from the normal retina image (FIG. 6A-D). Therefore, the system of the application can detect new vessels on optic disc accurately (FIG. 6).

Comparison with Other Detections

TABLE 27

RESULTS OF HEMORRHAGES DETECTION, EXUDATES DETECTION AND SIMPLE GRADING FROM OTHER RESEARCH GROUPS.

|  |  | Hemorrhage | Exudates | Grading* |
|---|---|---|---|---|
| Lee, S.C. et al. 2001 | Sensitivity(%) | 77 | 59 | N/A |
| (n = 369) [ref. 41] | Specificity(%) | 100 | 96 | N/A |
| Abramoff et al. 2008 | Sensitivity(%) | 100 | 95 | 84 |
|  |  | (n = 100)[ref. 42] | (n = 300)[ref. 43] | n = (7689)[ref. 44] |
|  | Specificity(%) | 87 | 88 | 64 |
| Philip et al. 2007 | Sensitivity(%) | 71 | 95 | 91 |
|  |  | (n = 10846)[ref. 45] | (n = 13219)[ref. 46] | (n = 6722)[ref. 11] |
|  | Specificity(%) | 76 | 84 | 67 |
| Usher et al. 2004 | Sensitivity(%) | 77.5 | 88.5 | 9 |
|  |  | (n = 30) | (n = 30) | (n = 1273) [ref. 47] |
|  | Specificity(%) | 88.7 | 99.7 | 53 |

*Grading: differentiate retina images with any hemorrhages or exudates from those without.

Compared with the existing results, the system of the application successfully detects hemorrhages and exudates automatically, and the accuracy is 93.85% based on the database "DIARETDB0" with 110 retina images. The accuracy of referral rate is also 93.85%. The results obtained by the system of the application are much better than current available systems.

Overall Grading Summary:

|  | Positive (Normal) | Negative (Abnormal) |  |  |
|---|---|---|---|---|
| Positive (Normal) | TP = 89 | FP = 5 | TPR = 89/94 = 94.68% |  |
| Negative (Abnormal) | FN = 0 | TN = 36 | FPR = 36/36 = 100% |  |
| AUC = 70.8% | Sensitivity = 89/89 = 100% | Specificity = 36/41 = 87.8% | Accuracy: 125/130 = 93.85% |  |

In general, these experimental data clearly demonstrate that the system can detect abnormal patterns in the retina image and grade the severity of diabetic retinopathy more accurately. Specifically, the preprocessing step using biostatistical methods greatly improved the efficiency of the subsequent image recognition processes, and the development of texture parameters and the location information have increased the accuracy of both HE and exudates detection and allowing quantify the outcome. Furthermore, the system incorporating the texture techniques increased the accuracy of detecting new vessels.

All of the above patents, patent applications and non-patent publications referred to in this specification are incorporated herein by reference, in their entirety.

From the foregoing it will be appreciated that, although specific embodiments of the application have been described herein for purposes of illustration, various modifications or variations may be made by those skilled in the art without deviating from the spirit and scope of the appended claims.

REFERENCE

[b1] Wong T Y, Shankar A, Klein R, Klein B E K, Hubbard L D. Prospective cohort study of retinal vessel diameters and risk of hypertension. BMJ. 2004; 329:799-800.

[b2] T. J. MacGillivary, N. Patton, F. N. Doubal, C. Graham and J. M. Wardlaw, Fractal analysis of the retinal vascular network in fundus images, Proceedings of the 29th Annual International Conference of the IEEE EMBS, Aug. 23-26, 2007.

[b3] Mainster M. A., The fractal properties of retinal vessels: embryological and clinical implications, Eye, 1990, 4(Pt 1):235-241.

[b4] Daxer A., The fractal geometry of proliferative diabetic retinopathy: implications for the diagnosis and the process of retinal vasculogenesis. Curr Eye Res. 1993; 12:1103-1109.

[b5] W. Hsu, M. L. Lee and T. Y. Wong, "Retinal Image analysis systems and methods", U.S. Patent 2011/0026789 A1, Feb. 3, 2011.

[b6] Acharaya, U. R., Chua, C. K., Ng, E. Y. K., Yu, W. W. and Chee, C., Application of High Order Spectra for the Identification of Diabetes Retinopathy Stages. J. Med. Syst. 32:481-488, 2008.

[b7] Dobrescu R., Dobrescu M. and et al., Medical images classification for skin cancer diagnosis based on combined texture and fractal analysis. WSEAS TRANSACTIONS on BIOLOGY and BIOMEDICINE, Issues 3, vol. 7, July 2010.

[b8] Sadeghzadeh, R., Berks, M., Astley, S. & Taylor, C (2010). *Detection of Retinal Blood Vessels Using Complex Wavelet Transforms and Random Forest Classification*. Presented at Medical Image Understanding and Analysis. Warwick: BMVA Press. eScholarID:115948

1. Fauci A S. Harrison's principles of internal medicine. 17th ed. New York: McGraw-Hill Medical, 2008.
2. Donnan G A, Fisher M, Macleod M, Davis S M. Stroke. Lancet 2008; 371(9624):1612-23.
3. Murray C J, Lopez A D. Mortality by cause for eight regions of the world: Global Burden of Disease Study. Lancet 1997; 349(9061):1269-76.
4. Bonita R. Epidemiology of stroke. Lancet 1992; 339(8789):342-4.
5. Murray C J, Lopez A D. Global mortality, disability, and the contribution of risk factors: Global Burden of Disease Study. Lancet 1997; 349(9063):1436-42.
6. Roger V L, Go A S, Lloyd-Jones D M, Adams R J, Berry J D, Brown T M, et al. Heart disease and stroke statistics—2011 update: a report from the American Heart Association. Circulation; 123 (4): e18-e209.
7. Rosamond W, Flegal K, Friday G, Furie K, Go A, Greenlund K, et al. Heart disease and stroke statistics—2007 update: a report from the American Heart Association Statistics Committee and Stroke Statistics Subcommittee. Circulation 2007; 115 (5): e69-171.
8. Sudlow C L, Warlow C P. Comparing stroke incidence worldwide: what makes studies comparable? Stroke 1996; 27(3):550-8.

9. Rothwell P M, Coull A J, Silver L E, Fairhead J F, Giles M F, Lovelock C E, et al. Population-based study of event-rate, incidence, case fatality, and mortality for all acute vascular events in all arterial territories (Oxford Vascular Study). Lancet 2005; 366(9499):1773-83.

10. Whisnant J P. Modeling of risk factors for ischemic stroke. The Willis Lecture. Stroke 1997; 28(9): 1840-4.

10B. Grau A J, Weimar C, Buggle F, et al. Risk factors, outcome, and treatment in subtypes of ischemic stroke: the German stroke data bank. Stroke. 2001 November; 32(11): 2559-66.

10C. Zhou H, Wang Y J, Wang, et al. TOAST subtyping of acute ischemic stroke Zhonghua Nei Ke Za Zhi. 2004 July; 43(7):495-8.

11. Goldstein L B, Bushnell C D, Adams R J, Appel L J, Braun L T, Chaturvedi S, et al. Guidelines for the primary prevention of stroke: a guideline for healthcare professionals from the American Heart Association/American Stroke Association. Stroke; 42(2):517-84.

12. Sacco R L, Adams R, Albers G, Alberts M J, Benavente O, Furie K, et al. Guidelines for prevention of stroke in patients with ischemic stroke or transient ischemic attack: a statement for healthcare professionals from the American Heart Association/American Stroke Association Council on Stroke: co-sponsored by the Council on Cardiovascular Radiology and Intervention: the American Academy of Neurology affirms the value of this guideline. Stroke 2006; 37(2):577-617.

13. Ebrahim S. Cost-effectiveness of stroke prevention. Br Med Bull 2000; 56(2):557-70.

14. Wolf P A, D'Agostino R B, Belanger A J, Kannel W B. Probability of stroke: a risk profile from the Framingham Study. Stroke 1991; 22(3):312-8.

15. Risau W. Mechanisms of angiogenesis. Nature 1997; 386(6626):671-4.

16. Hughes S, Yang H, Chan-Ling T. Vascularization of the human fetal retina: roles of vasculogenesis and angiogenesis. Invest Ophthalmol Vis Sci 2000; 41(5):1217-28.

17. Hardy P, Varma D R, Chemtob S. Control of cerebral and ocular blood flow autoregulation in neonates. Pediatr Clin North Am 1997; 44(1):137-52.

18. Lassen N A. Autoregulation of Cerebral Blood Flow. Circ Res 1964; 15:SUPPL:201-4.

19. Delaey C, Van De Voorde J. Regulatory mechanisms in the retinal and choroidal circulation. Ophthalmic Res 2000; 32(6):249-56.

20. Netter F H. Atlas of human anatomy. 4th ed. Philadelphia, Pa.: Saunders/Elsevier, 2006.

21. Bradbury M W, Lightman S L. The blood-brain interface. Eye (Lond) 1990; 4 (Pt 2):249-54.

22. Cogan D G, Kuwabara T. Comparison of retinal and cerebral vasculature in trypsin digest preparations. Br J Ophthalmol 1984; 68(1):10-2.

23. Lightman S L, Palestine A G, Rapoport S I, Rechthand E. Quantitative assessment of the permeability of the rat blood-retinal barrier to small water-soluble non-electrolytes. J Physiol 1987; 389:483-90.

24. Wallow I H, Burnside B. Actin filaments in retinal pericytes and endothelial cells. Invest Ophthalmol Vis Sci 1980; 19(12):1433-41.

25. Farrell C R, Stewart P A, Farrell C L, Del Maestro R F. Pericytes in human cerebral microvasculature. Anat Rec 1987; 218(4):466-9.

26. Robinson F, Riva C E, Grunwald J E, Petrig B L, Sinclair S H. Retinal blood flow autoregulation in response to an acute increase in blood pressure. Invest Ophthalmol Vis Sci 1986; 27(5):722-6.

27. Riva C E, Sinclair S H, Grunwald J E. Autoregulation of retinal circulation in response to decrease of perfusion pressure. Invest Ophthalmol Vis Sci 1981; 21(1 Pt 1):34-8.

28. Vavilala M S, Lee L A, Lam A M. Cerebral blood flow and vascular physiology. Anesthesiol Clin North America 2002; 20(2):247-64, v.

29. Grunwald J E, Piltz J, Patel N, Bose S, Riva C E. Effect of aging on retinal macular microcirculation: a blue field simulation study. Invest Ophthalmol Vis Sci 1993; 34(13): 3609-13.

30. Groh M J, Michelson G, Langhans M J, Harazny J. Influence of age on retinal and optic nerve head blood circulation. Ophthalmology 1996; 103(3):529-34.

31. Hill G S. Studies on the pathogenesis of hypertensive vascular disease. Effect of high-pressure intra-arterial injections in rats. Circ Res 1970; 27(5):657-68.

32. Tso M O, Jampol L M. Pathophysiology of hypertensive retinopathy. Ophthalmology 1982; 89(10):1132-45.

33. Goto I, Katsuki S, Ikui H, Kimoto K, Mimatsu T. Pathological studies on the intracerebral and retinal arteries in cerebrovascular and noncerebrovascular diseases. Stroke 1975; 6(3):263-9.

34. Sharrett A R, Hubbard L D, Cooper L S, Sorlie P D, Brothers R J, Nieto F J, et al. Retinal arteriolar diameters and elevated blood pressure: the Atherosclerosis Risk in Communities Study. Am J Epidemiol 1999; 150(3):263-70.

35. Lammie G A, Brannan F, Slattery J, Warlow C. Nonhypertensive cerebral small-vessel disease. An autopsy study. Stroke 1997; 28(11):2222-9.

36. Furuta A, Ishii N, Nishihara Y, Horie A. Medullary arteries in aging and dementia. Stroke 1991; 22(4):442-6.

37. Fredriksson K, Nordborg C, Kalimo H, Olsson Y, Johansson B B. Cerebral microangiopathy in stroke-prone spontaneously hypertensive rats. An immunohistochemical and ultrastructural study. Acta Neuropathol 1988; 75(3):241-52.

38. Gustafsson F. Hypertensive arteriolar necrosis revisited. Blood Press 1997; 6(2):71-7.

39. Cai J, Boulton M. The pathogenesis of diabetic retinopathy: old concepts and new questions. Eye (Lond) 2002; 16(3):242-60.

40. Kern T S, Engerman R L. Capillary lesions develop in retina rather than cerebral cortex in diabetes and experimental galactosemia. Arch Ophthalmol 1996; 114(3):306-10.

41. Mukai N, Hori S, Pomeroy M. Cerebral lesions in rats with streptozotocin-induced diabetes. Acta Neuropathol 1980; 51(1):79-84.

42. Frank R N, Dutta S, Frank S E. Cerebral cortical capillary basement membrane thickening in galactosaemic rats. Diabetologia 1987; 30(9):739-44.

43. Jakobsen J, Sidenius P, Gundersen H J, Osterby R. Quantitative changes of cerebral neocortical structure in insulin-treated long-term streptozocin-induced diabetes in rats. Diabetes 1987; 36(5):597-601.

44. Cheung N, Mitchell P, Wong T Y. Diabetic retinopathy. Lancet; 376(9735):124-36.

45. Grading diabetic retinopathy from stereoscopic color fundus photographs—an extension of the modified Airlie House classification. ETDRS report number 10. Early Treatment Diabetic Retinopathy Study Research Group. Ophthalmology 1991; 98(5 Suppl):786-806.

46. Wong T Y, Mitchell P. Hypertensive retinopathy. N Engl J Med 2004; 351(22):2310-7.

47. Doubal F N, Hokke P E, Wardlaw J M. Retinal microvascular abnormalities and stroke: a systematic review. J Neurol Neurosurg Psychiatry 2009; 80(2):158-65.
48. Wong T Y, Klein R, Couper D J, Cooper L S, Shahar E, Hubbard L D, et al. Retinal microvascular abnormalities and incident stroke: the Atherosclerosis Risk in Communities Study. Lancet 2001; 358(9288):1134-40.
49. Wong T Y, Klein R, Sharrett A R, Couper D J, Klein B E, Liao D P, et al. Cerebral white matter lesions, retinopathy, and incident clinical stroke. JAMA 2002; 288(1):67-74.
50. Cheung N, Rogers S, Couper D J, Klein R, Sharrett A R, Wong T Y. Is diabetic retinopathy an independent risk factor for ischemic stroke? Stroke 2007; 38(2):398-401.
51. Hirai F E, Moss S E, Knudtson M D, Klein B E, Klein R. Retinopathy and survival in a population without diabetes: The Beaver Dam Eye Study. Am J Epidemiol 2007; 166(6):724-30.
52. Mitchell P, Wang J J, Wong T Y, Smith W, Klein R, Leeder S R. Retinal microvascular signs and risk of stroke and stroke mortality. Neurology 2005; 65(7):1005-9.
53. Klein B E, Klein R, McBride P E, Cruickshanks K J, Palta M, Knudtson M D, et al. Cardiovascular disease, mortality, and retinal microvascular characteristics in type 1 diabetes: Wisconsin epidemiologic study of diabetic retinopathy. Arch Intern Med 2004; 164(17):1917-24.
54. Klein R, Klein B E, Moss S E, Cruickshanks K J. Association of ocular disease and mortality in a diabetic population. Arch Ophthalmol 1999; 117(11):1487-95.
55. Cooper L S, Wong T Y, Klein R, Sharrett A R, Bryan R N, Hubbard L D, et al. Retinal microvascular abnormalities and MRI-defined subclinical cerebral infarction: the Atherosclerosis Risk in Communities Study. Stroke 2006; 37(1):82-6.
56. Wong T Y, Klein R, Sharrett A R, Manolio T A, Hubbard L D, Marino E K, et al. The prevalence and risk factors of retinal microvascular abnormalities in older persons: The Cardiovascular Health Study. Ophthalmology 2003; 110(4):658-66.
57. Longstreth W, Jr., Larsen E K, Klein R, Wong T Y, Sharrett A R, Lefkowitz D, et al. Associations between findings on cranial magnetic resonance imaging and retinal photography in the elderly: the Cardiovascular Health Study. Am J Epidemiol 2007; 165(1):78-84.
58. Wong T Y, Barr E L, Tapp R J, Harper C A, Taylor H R, Zimmet P Z, et al. Retinopathy in persons with impaired glucose metabolism: the Australian Diabetes Obesity and Lifestyle (AusDiab) study. Am J Ophthalmol 2005; 140(6):1157-9.
59. Petitti D B, Bhatt H. Retinopathy as a risk factor for nonembolic stroke in diabetic subjects. Stroke 1995; 26(4):593-6.
60. Kwon H M, Kim B J, Oh J Y, Kim S J, Lee S H, Oh B H, et al. Retinopathy as an indicator of silent brain infarction in asymptomatic hypertensive subjects. J Neurol Sci 2007; 252(2):159-62.
61. El-Asrar A M, Al-Rubeaan K A, Al-Amro S A, Moharram O A, Kangave D. Retinopathy as a predictor of other diabetic complications. Int Ophthalmol 2001; 24(1):1-11.
62. Ikram M K, de Jong F J, Bos M J, Vingerling J R, Hofman A, Koudstaal P J, et al. Retinal vessel diameters and risk of stroke: the Rotterdam Study. Neurology 2006; 66(9):1339-43.
63. Parr J C, Spears G F. General caliber of the retinal arteries expressed as the equivalent width of the central retinal artery. Am J Ophthalmol 1974; 77(4):472-7.
64. Knudtson M D, Lee K E, Hubbard L D, Wong T Y, Klein R, Klein B E. Revised formulas for summarizing retinal vessel diameters. Curr Eye Res 2003; 27(3):143-9.
65. Murray C D. The Physiological Principle of Minimum Work Applied to the Angle of Branching of Arteries. J Gen Physiol 1926; 9(6):835-41.
66. Murray C D. The Physiological Principle of Minimum Work: II. Oxygen Exchange in Capillaries. Proc Natl Acad Sci USA 1926; 12(5):299-304.
67. Murray C D. The Physiological Principle of Minimum Work: I. The Vascular System and the Cost of Blood Volume. Proc Natl Acad Sci USA 1926; 12(3):207-14.
68. Frame M D, Sarelius I H. Energy optimization and bifurcation angles in the microcirculation. Microvasc Res 1995; 50(3):301-10.
69. Hardy-Stashin J, Meyer W W, Kauffman S L. Branching coefficient ("area ratio") of the human aortic bifurcation determined in distended specimens. Atherosclerosis 1980; 37(3):399-402.
70. Zamir M, Medeiros J A. Arterial branching in man and monkey. J Gen Physiol 1982; 79(3):353-60.
71. Stanton A V, Wasan B, Cerutti A, Ford S, Marsh R, Sever P P, et al. Vascular network changes in the retina with age and hypertension. J Hypertens 1995; 13(12 Pt 2):1724-8.
72. Chapman N, Dell'omo G, Sartini M S, Witt N, Hughes A, Thom S, et al. Peripheral vascular disease is associated with abnormal arteriolar diameter relationships at bifurcations in the human retina. Clin Sci (Loud) 2002; 103(2):111-6.
73. Zamir M. Nonsymmetrical bifurcations in arterial branching. J Gen Physiol 1978; 72(6):837-45.
74. Sherman T F. On connecting large vessels to small. The meaning of Murray's law. J Gen Physiol 1981; 78(4):431-53.
75. Zamir M. Shear forces and blood vessel radii in the cardiovascular system. J Gen Physiol 1977; 69(4):449-61.
76. Zamir M, Medeiros J A, Cunningham T K. Arterial bifurcations in the human retina. J Gen Physiol 1979; 74(4):537-48.
77. Taarnhoj N C, Munch I C, Sander B, Kessel L, Hougaard J L, Kyvik K, et al. Straight versus tortuous retinal arteries in relation to blood pressure and genetics. Br J Ophthalmol 2008; 92(8):1055-60.
78. Hiroki M, Miyashita K, Oda M. Tortuosity of the white matter medullary arterioles is related to the severity of hypertension. Cerebrovasc Dis 2002; 13(4):242-50.
79. Spangler K M, Challa V R, Moody D M, Bell M A. Arteriolar tortuosity of the white matter in aging and hypertension. A microradiographic study. J Neuropathol Exp Neurol 1994; 53(1):22-6.
80. Wood N B, Zhao S Z, Zambanini A, Jackson M, Gedroyc W, Thom S A, et al. Curvature and tortuosity of the superficial femoral artery: a possible risk factor for peripheral arterial disease. J Appl Physiol 2006; 101(5):1412-8.
81. Moody D M, Santamore W P, Bell M A. Does tortuosity in cerebral arterioles impair down-autoregulation in hypertensives and elderly normotensives? A hypothesis and computer model. Clin Neurosurg 1991; 37:372-87.
82. Bracher D. Changes in peripapillary tortuosity of the central retinal arteries in newborns. A phenomenon whose underlying mechanisms need clarification. Graefes Arch Clin Exp Ophthalmol 1982; 218(4):211-7.
83. Hughes A D, Stanton A V, Jabbar A S, Chapman N, Martinez-Perez M E, Mc GTSA. Effect of antihypertensive treatment on retinal microvascular changes in hypertension. Hypertens 2008; 26(8):1703-7.

84. Pose-Reino A, Rodriguez-Fernandez M, Hayik B, Gomez-Ulla F, Carrera-Nouche M J, Gude-Sampedro F, et al. Regression of alterations in retinal microcirculation following treatment for arterial hypertension. J Clin Hypertens (Greenwich) 2006; 8(8):590-5.

85. Bennett A G, Rudnicka A R, Edgar D F. Improvements on Littmann's method of determining the size of retinal features by fundus photography. Graefes Arch Clin Exp Ophthalmol 1994; 232(6):361-7.

86. Behrendt T, Doyle K E. Reliability of Image Size Measurements in the New Zeiss Fundus Camera. Am J Ophthalmol 1965; 59:896-9.

87. Pach J, Pennell D O, Romano P E. Optic disc photogrammetry: magnification factors for eye position, centration, and ametropias, refractive and axial; and their application in the diagnosis of optic nerve hypoplasia. Ann Ophthalmol 1989; 21(12):454-62.

88. Arnold J V, Gates J W, Taylor K M. Possible errors in the measurement of retinal lesions. Invest Ophthalmol Vis Sci 1993; 34(8):2576-80.

89. Lotmar W. Dependence of magnification upon the camera-to-eye distance in the Zeiss fundus camera. Acta Ophthalmol (Copenh) 1984; 62(1):131-4.

90. Garway-Heath D F, Rudnicka A R, Lowe T, Foster P J, Fitzke F W, Hitchings R A. Measurement of optic disc size: equivalence of methods to correct for ocular magnification. Br J Ophthalmol 1998; 82(6):643-9.

91. Bengtsson B, Krakau C E. Some essential optical features of the Zeiss fundus camera. Acta Ophthalmol (Copenh) 1977; 55(1):123-31.

92. Littmann H. Determination of the true size of an object on the fundus of the living eye. By H. Littmann from the original article, "Zur Bestimmung der wahren Grosse eines Objektes auf dem Hintergrund des lebenden Auges," which originally appeared in Klinisches Monatsblatter fur Augenheilkunde 1982; 180:286-9. Translated by T D Williams. Optom Vis Sci 1992; 69(9):717-20.

93. Bengtsson B, Krakau C E. Correction of optic disc measurements on fundus photographs. Graefes Arch Clin Exp Ophthalmol 1992; 230(1):24-8.

94. Irving B A, Weltman J Y, Brock D W, Davis C K, Gaesser G A, Weltman A. NIH ImageJ and Slice-O-Matic computed tomography imaging software to quantify soft tissue. Obesity (Silver Spring) 2007; 15(2):370-6.

95. Patton N, Aslam T, Macgillivray T, Dhillon B, Constable I. Asymmetry of retinal arteriolar branch widths at junctions affects ability of formulae to predict trunk arteriolar widths. Invest Ophthalmol Vis Sci 2006; 47(4):1329-33.

96. Chiang M F, Gelman R, Jiang L, Martinez-Perez M E, Du Y E, Flynn J T. Plus disease in retinopathy of prematurity: an analysis of diagnostic performance. Trans Am Ophthalmol Soc 2007; 105:73-84; discussion 84-5.

97. Hart W E, Goldbaum M, Cote B, Kube P, Nelson M R. Measurement and classification of retinal vascular tortuosity. Int J Med Inform 1999; 53(2-3):239-52.

98. Witt N, Wong T Y, Hughes A D, Chaturvedi N, Klein B E, Evans R, et al. Abnormalities of retinal microvascular structure and risk of mortality from ischemic heart disease and stroke. Hypertension 2006; 47(5):975-81.

99. Dunn G. Design and analysis of reliability studies. Stat Methods Med Res 1992; 1(2):123-57.

100. Margo C E, Harman L E, Mulla Z D. The reliability of clinical methods in ophthalmology. Sury Ophthalmol 2002; 47(4):375-86.

101. Gerbet D, Richardot P, Auget J L, Maccario J, Cazalet C, Raichvarg D, et al. New statistical approach in biochemical method-comparison studies by using Westlake's procedure, and its application to continuous-flow, centrifugal analysis, and multilayer film analysis techniques. Clin Chem 1983; 29(6):1131-6.

102. Bland J M, Altman D G. Statistical methods for assessing agreement between two methods of clinical measurement. Lancet 1986; 1(8476):307-10.

103. Kramer M S, Feinstein A R. Clinical biostatistics. LIV. The biostatistics of concordance. Clin Pharmacol Ther 1981; 29(1):111-23.

104. Bland J M, Altman D G. A note on the use of the intraclass correlation coefficient in the evaluation of agreement between two methods of measurement. Comput Biol Med 1990; 20(5):337-40.

105. Lindley R I, Wang J J, Wong M C, Mitchell P, Liew G, Hand P, et al. Retinal microvasculature in acute lacunar stroke: a cross-sectional study. Lancet Neurol 2009; 8(7): 628-34.

107 Panel. AAoOR. Preferred Practice Pattern® Guidelines. Diabetic Retinopathy. San Francisco, Calif. American Academy of Ophthalmology, 2008.

108 Mitchell P, Leung H, Wang J J, Rochtchina E, Lee A J, Wong T Y, et al. Retinal vessel diameter and open-angle glaucoma: the Blue Mountains Eye Study. Ophthalmology 2005; 112(2):245-50.1 S. C. Lee and Y. Wang, Automatic retinal image quality assessment and enhancement, In Proc. SPIE Conf. on Image Processing, page 1581-1590, February 1999.

109 C. F. Li, A. C. Bovik and X. J. Wu, Blind Image Quality Assessment Using a General Regression Neural Network, IEEE TRANSACTIONS ON NEURAL NETWORKS, VOL. 22, NO. 5, MAY 2011.

110 A. D. Fleming, S. P, K. A. Goatman, J. A. Olson and P. F. Sharp, Automated Assessment of Diabetic Retinal Image Quality Based on Clarity and Field Definition, IOVS, March 2006, Vol. 47, No. 3

111 T. Brandão and M. P. Queluz, "No-reference image quality assessment based on DCT domain statistics," Signal Process., vol. 88, no. 4, pp. 822-833, April 2008.

112 Usher D B, Himaga M, Dumskyj M J, et al. Automated assessment of digital fundus image quality using detected vessel area. Proceedings of Medical Image Understanding and Analysis. Sheffield, U K: British Machine Vision Association (BMVA); 2003:81-84.

113 Lalonde M, Gagnon L, Boucher M. Automatic visual quality assessment in optical fundus images. Proceedings of Vision Interface. Ottawa, Ontario, Canada; 2001; 259-264. Available at http://www.cipprs.org/vi2001/schedule-final.html.

114 Fleming A D, Philip S, Goatman K A, Olson J A, Sharp P F. Automated assessment of retinal image field of view. Proceedings of Medical Image Understanding and Analysis, London, UK: British Machine Vision Association (BMVA); 2004:129-132.

115 Herman Bartling, Peter Wanger and Lene Martin, Automated quality evaluation of digital fundus photographs, Acta Ophthalmologica 2009;87:643-647

116 J. Paulus, J. Meier, R. Bock, J. Hornegger and G. Michelson, Automated quality assessment of retinal fundus photos, Int J CARS (2010) 5:557-564

117 L. Tramontan, E. Grisan, and A. Ruggeri, An improved system for the automatic estimation of the Arteriolarto-Venular diameter Ratio (AVR) in retinal images, 30th Annual International IEEE EMBS Conference Vancouver, British Columbia, Canada, August 20-24, 2008.

118 Wong T Y, Klein R, Couper D J, Cooper L S, Shahar E, Hubbard L D, Wofford M R, Sharrett A R. Retinal microvascular abnormalities and incident stroke: the Atherosclerosis Risk in Communities Study. Lancet. 2001; 358:1134-1140.

119 Wong T Y, Klein R, Sharrett A R, Duncan B B, Couper D J, Tielsch J M, Klein B E, Hubbard L D. Retinal arteriolar narrowing and risk of coronary heart disease in men and women. The Atherosclerosis Risk in Communities Study. JAMA. 2002; 287:1153-1159.

120 Wong T Y, Klein R, Klein B E, Tielsch J M, Hubbard L, Nieto F J. Retinal microvascular abnormalities and their relationship with hypertension, cardiovascular disease, and mortality. Sury Ophthalmol. 2001; 46:59-80.

121 King L A, Stanton A V, Sever P S, Thom S A, Hughes A D. Arteriolar length-diameter (L:D) ratio: a geometric parameter of the retinal vasculature diagnostic of hypertension. J Hum Hypertens. 1996; 10:417-418.

122 Chapman N, Witt N, Gao X, Bharath A A, Stanton A V, Thom S A, Hughes A D. Computer algorithms for the automated measurement of retinal arteriolar diameters. Br J. Ophthalmol. 2001; 85:74-79.

123 Stanton A V, Mullaney P, Mee F, O'Brien E T, O'Malley K. A method of quantifying retinal microvascular alterations associated with blood pressure and age. J. Hypertens. 1995; 13:41-48.

124 Hart W E, Goldbaum M, Cote B, Kube P, Nelson M R. Measurement and classification of retinal vascular tortuosity. Int J Med Inform. 1999; 53: 239-252.

125 Zamir M. Nonsymmetrical bifurcations in arterial branching. J Gen Physiol. 1978; 72:837-845.

126 Sutter F K, Helbig H. Familial retinal arteriolar tortuosity: a review. Sury Ophthalmol. 2003; 48:245-255.

127 N. Patton, T. Aslam, T. MacGillivray, B. Dhillon and I. Constable, Asymmetry of Retinal Arteriolar Branch Widths at Junctions Affects Ability of Formulae to Predict Trunk Arteriolar Widths, IOVS, April 2006, Vol. 47, No. 4

128 Knudtson M, Lee K, Hubbard L, Wong T, Klein R, Klein B. Revised formulas for summarizing retinal vessel diameters. Curr Eye Res. 2003; 27:143-149.

129 F. N. Doubal, T. J. MacGillivray, P. E. Hokke, B. Dhillon, M. S. Dennis and J. M. Wardlaw, Differences in retinal vessels support a distinct vasculopathy causing lacunar stroke, Neurology 2009; 72; 1773

130 Doubal F N, Hokke P, Wardlaw J M. Retinal microvascular abnormalities and stroke: a systematic review. J Neurol Neurosurg Psychiatry 2009; 80:158-165.

131 Ikram M K, De Jong F J, Bos M J, et al. Retinal vessel diameters and risk of stroke: the Rotterdam Study. Neurology 2006; 66:1339-1343.

132 Mitchell P, Wang J J, Wong T Y, Smith W, Klein R, Leeder S R. Retinal microvascular signs and risk of stroke and stroke mortality. Neurology 2005; 65:1005-1009.

133 M. D. Fischer, G. Huber, Y. X. Feng, N. Tanimoto and et. al., In Vivo Assessment of Retinal Vascular Wall Dimensions, IOVS, October 2010, Vol. 51, No. 10

134 M. Niemeijer, X. Y. Xu, A. V. Dumitrescu, P. Gupta, B. Ginneken, J. C. Folk, M. D. Abe'amoff, Automated Measurement of the Arteriolar-To-Venular Width Ratio in Digital Color Fundus Photographs, IEEE TRANSACTIONS ON MEDICAL IMAGING, 2011

135 L. Tramontan and A. Ruggeri, Computer estimation of the AVR parameter in diabetic retinopathy, IFMBE Proceedings 25/XI, pp. 141-144, 2009.

136 Hubbard L. D., Brothers R. J. et al. (1999). Methods for evaluation of retinal microvascular abnormalities associated with hypertension/sclerosis in the atherosclerosis risk in communities studies, Ophthalmology, vol. 106: 2269-80.

137 Wong T. Y., Knudtson M., Klein R., Klein B. E. K., Meuer S. M., Hubbard L. D. (2004), Computer-assisted measurement of retinal vessel diameters in the Beaver Dam eye study, Ophthalmology, vol. 111: 1183-90.

138 Li H., Hsu W., Lee M. L., Wong T. Y. (2005), Automatic grading of retinal vessel caliber, IEEE Trans Biomed Eng, vol. 52: 1352-5

139 Tramontan L., Grisan E., Ruggeri A. (2008), An improved system for the automatic estimation of the Arteriolar-to-Venular diameter (AVR) in retinal images, Proc. 30th Annual International Conference of IEEE-EMBS: 3550-3, IEEE, Vancouver.

140 The DCCT Group (1987), Color photography vs. fluorescein angiography in the detection of diabetic retinopathy in the Diabetes Control and Complications Trial, Arch Ophthalmol. 105:1344-51.

141 Early Treatment Diabetic Retinopathy Study Research Group (1991), Grading diabetic retinopathy from stereoscopic fundus photographs—an extension of the modified Airlie House classification, Ophthalmology 98: 786-806.

142 Knudtson M. D., Lee K. E., Hubbard L. H., Wong T. Y., Klein R., Klein B. E. K. (2003), Revised formulas for summarizing retinal vessel diameters, Current Eye Research, vol. 27, no. 3: 143-149.

143 R. C. Gonzalez, R. E. Woods, Digital Image Processing, Addison-Wesley, Reading, Mass., 1992.

144 J. C. Russ, The Image Processing Handbook, 3rd edition, CRC Press, Florida, 1999.

145 IEEE Standard 610.4-1990.

146 S. Livens, Image Analysis for Material Characterization, PhD thesis, University of Antwerp, Antwerp, Belgium, 1998.

147 T. Randen, Filter and Filter Bank Design for Image Texture Recognition, PhD thesis, NTNU, Stavanger, Norway, 1997.

148 G. Van de Wouwer, Wavelets for Multiscale Texture Analysis, PhD thesis, University of Antwerp, Antwerp, Belgium, 1998.

149 K. Kvaal, J. P. Wold, U. G. Indhal, P. Baardseth, T. Næs, Chemometr. Intell. Lab. Syst. 42 (1998) 141-158.

150 L. Carlucci, Pattern Recogn. 4 (1972) 53-72.

151 S. W. Zucker, Comput. Vis. Graph. Image Process. 5 (1976) 190-202.

152 A. Sarkar, K. M. S. Sharma, R. V. Sonak, IEEE Trans. Image Process. 6 (1997) 407-413.

153 G. Cross, A. Jain, IEEE Trans. Pattern Anal. Mach. Intell. 5 (1983) 25-39.

154 J. M. Keller, S. Chen, R. M. Crownover, Comput. Vis. Graph. Image Process. 45 (1989) 150-166.

155 U. Indhal, T. Næs, J. Chemometr. 12 (1998) 261-278.

156 P. Geladi, Chemometr. Intell. Lab. Syst. 14 (1992) 375-390.

157 A. Bovik, M. Clark, W. Geisler, IEEE Trans. Pattern Anal. Mach. Intell. 12 (1990) 55-73.

158 T. Chang, C. C. J. Kuo, IEEE Trans. Image Process. 2 (1993) 429-441.

159 M. Unser, IEEE Trans. Image Process. 4 (1995) 1549-1560.

160 A. Laine, J. Fan, IEEE Trans. Pattern Anal. Mach. Intell. 15 (1995) 1186-1191.

161 J. Huang, K. H. Esbensen, Chemometr. Intell. Lab. Syst. 54 (2000) 1-19.

162 C. L. Nikias and A. P. Petropulu, Higher-order spectra analysis: a nonlinear signal processing framework, Englewood Cliffs, N.J.: PTR Prentice Hall, 1993.

163 Chandran, V., Carswell, B., Boashash, B., Elgar, S. L., "Pattern Recognition Using Invariants Defined from 163. Higher Order Spectra: 2-D Image Inputs", IEEE Transactions on image processing, 6, 1997, 703-712.
164. Kenneth F., Fractal Geometry—Mathematical Foundations and Applications. John Wiley & Sons, Chichester, 1990
165. Azemin M. Z., Kumar D. K., Wong T. Y., Kawasaki R. and Mitchell P., Robust Methodology for Fractal Analysis of the Retinal Vasculature, IEEE Transactions on Medical Imaging, VOl. 30, No. 2, February 2011.
166. M. B. M. Mendonça, C. A. A. Garcia, R. A. Nogueira, M. A. F. Gomes, M. M. Valença, and F. Oréfice, "Fractal analysis of retinal vascular tree: Segmentation and estimation methods," Arquivos Brasileiros de Oftalmologia, vol. 70, pp. 413-422, 2007.
167. G. Landini, G. P. Misson, and P. I. Murray, "Fractal analysis of the normal human retinal fluorescein angiogram," Current Eye Res., vol. 12, pp. 23-27, 1993.
168. B. R. Masters, "Fractal analysis of the vascular tree in the human retina," Annu Rev. Biomed. Eng., vol. 6, pp. 427-452, 2004.
169. G. Liew, J. J. Wang, N. Cheung, Y. P. Zhang, W. Hsu, M. L. Lee, P. Mitchell, G. Tikellis, B. Taylor, and T. Y. Wong, "The retinal vasculature as a fractal: Methodology, reliability, and relationship to blood pressure," Ophthalmology, vol. 115, pp. 1951-1956.e1, 2008.
170. F. Family, B. R. Masters, and D. E. Platt, "Fractal pattern formation in human retinal vessels," Physica D: Nonlinear Phenomena, vol. 38, pp. 98-103, 1989.
171. A. Daxer, "Characterisation of the neovascularisation process in diabetic retinopathy by means of fractal geometry: diagnostic implications," Clin. and Experimenl. Ophthalmol., vol. 231, pp. 681-686, 1993.
172. A. Avakian, R. E. Kalina, E. H. Sage, A. H. Rambhia, K. E. Elliott, E. L. Chuang, J. I. Clark, J. Hwang and P. Pasons-Wingerter, "Fractal analysis of region-based vascular changes in the normal and nonproliferative diabetic retina," Curr. Eye Res., vol. 24, no. 4, pp. 274-280, 2002.
173. T. J. MacGillivray and N. Patton, "A reliability study of fractal analysis of the skeletonised vascular network using the "boxcounting" technique," 28th IEEE EMBS, New York USA 2006.
174. Che Azemin, M. Z.; Kumar, D. K.; Wong, T. Y.; Wang, J. J.; Kawasaki, R.; Mitchell, P.; "Retinal stroke prediction using logistic-based fusion of multiscale fractal analysis," Imaging Systems and Techniques (IST), 2010 IEEE International Conference on, vol., no., pp. 125-128, 1-2 Jul. 2010
175. G. Liew, J. J. Wang, N. Cheung, Y. P. Zhang, W. Hsu, M. L. Lee, P. Mitchell, G. Tikellis, B. Taylor, and T. Y. Wong, "The retinal vasculature as a fractal: Methodology, reliability, and relationship to blood pressure," Ophthalmology, vol. 115, pp. 1951-1956.e1, 2008.
176. Wendt, H.; Abry, P.; Jaffard, S.; Hui Ji; Zuowei Shen; "Wavelet Leader multifractal analysis for texture classification," Image Processing (ICIP), 2009 16th IEEE International Conference on, vol., no., pp. 3829-3832, 7-10 Nov. 2009
177. Y. Xu, H. Ji and C. Fermüller, Viewpoint invariant texture description using fractal analysis, Int J Comput Vis (2009) 83: 85-100.
178. Acton, K. J., et al., Trends in diabetes prevalence among American Indian and Alaska native children, adolescents, and young adults. Am J Public Health, 2002. 92(9): p. 1485-90.
179. Panel, A. A. o. O. R. preferred practice pattern guidelines. Diabetic retinopathy. 2008; Available from: http://www.aao.org/ppp
180. Grading diabetic retinopathy from stereoscopic color fundus photographs—an extension of the modified Airlie House classification. ETDRS report number 10. Early Treatment Diabetic Retinopathy Study Research Group. Ophthalmology, 1991. 98(5 Suppl): p. 786-806.
181. Ruamviboonsuk, P., et al., Interobserver agreement in the interpretation of single-field digital fundus images for diabetic retinopathy screening. Ophthalmology, 2006. 113(5): p. 826-32.
182. Hove, M. N., et al., Quantitative analysis of retinopathy in type 2 diabetes: identification of prognostic parameters for developing visual loss secondary to diabetic maculopathy. Acta Ophthalmol Scand, 2004. 82(6): p. 679-85.
183. Hove, M. N., et al., The relationships between risk factors and the distribution of retinopathy lesions in type 2 diabetes. Acta Ophthalmol Scand, 2006. 84(5): p. 619-23.
184. Yen, G. G. and W. F. Leong, A sorting system for hierarchical grading of diabetic fundus images: a preliminary study. IEEE Trans Inf Technol Biomed, 2008. 12(1): p. 118-30.
185. Fleming, A. D., et al., The role of haemorrhage and exudate detection in automated grading of diabetic retinopathy. Br J. Ophthalmol. 94(6): p. 706-11.
185. Fleming, A. D., et al., Automatic detection of retinal anatomy to assist diabetic retinopathy screening. Phys Med Biol, 2007. 52(2): p. 331-45.
187. Acharya, R., et al., Automated Diagnosis of Glaucoma Using Texture and Higher Order Spectra Features. IEEE Trans Inf Technol Biomed. 2011, Epub ahead of print.
188. Philip, S., et al., The efficacy of automated "disease/no disease" grading for diabetic retinopathy in a systematic screening programme. Br J Ophthalmol, 2007. 91(11): p. 1512-7.
189. Doubal, F. N., et al., Fractal analysis of retinal vessels suggests that a distinct vasculopathy causes lacunar stroke. Neurology. 74(14): p. 1102-7.
190. Cheung, N., P. Mitchell, and T. Y. Wong, Diabetic retinopathy. Lancet. 376(9735): p. 124-36.
191. Kauppi, T., Kalesnykiene, V., Kamarainen, J.-K., Lensu, L., Sorri, I., Uusitalo, H., Kälviäinen, H., Pietila J, DIARETDB0: Evaluation Database and Methodology for Diabetic Retinopathy Algorithms. Technical report
192. Fleming, A. D., et al., Automated assessment of diabetic retinal image quality based on clarity and field definition. Invest Ophthalmol Vis Sci, 2006. 47(3): p. 1120-5.
193. Osareh, A., Automated Identification of Diabetic Retinal Exudates and the Optic Disc. PhD thesis. Department of Computer Science, University of Bristol, 2004.
194. Sonka, M., V. Hlavac, and R. Boyle, Image processing, analysis, and machine vision. 2nd ed. 1999, PWS Pub.
195. Chen, Y. Q., M. S, Nixon, and D. W. Thomas, Texture Classification Using Statistical Geometrical Features. Image Processing, 1994: p. 446-450 1050.
196. Pietikainen, M., T. Ojala, and Z. Xu, Rotation-invariant texture classification using feature distributions. Pattern Recognition, 2000. 33(1): p. 43-52.
197. Chang, T. and C. C. J. Kuo, Texture analysis and classification with tree-structured wavelet transform. Ieee Transactions on Image Processing, 1993. 2(4): p. 429-441.
198. Gonzalez, R. C. and R. C. Woods, Digital image processing. 1992, Addison-Wesley.
199. Russ, J. C., The image processing handbook. 3rd ed. 1999, CRC Press.
200. Livens, S., Image Analysis for Material Characterization. PhD thesis, University of Antwerp, Antwerp, Belgium.

201 Randen, T., Filter and Filter Bank Design for Image Texture Recognition. PhD thesis, NTNU, Stavanger, Norway.
202 Wouwer, G. V. d., Wavelets for Multiscale Texture Analysis. PhD thesis, University of Antwerp, Antwerp, Belgium.
203 Kvaal, K., et al., Multivariate feature extraction from textural images of bread. Chemometrics and Intelligent Laboratory Systems, 1998. 42(1-2): p. 141-158.
204 Carlucci, L., Formal System for Texture Languages. Pattern Recognition, 1972. 4(1): p. 53-72.
205 Zucker, S., Toward a model of texture. Comput. Graphics Image Process, 1976. 5, p. 190-202.
206 Sarkar, A., K. M. S. Sharma, and R. V. Sonak, A new approach for subset 2-D AR model identification for describing textures. Ieee Transactions on Image Processing, 1997. 6(3): p. 407-413.
207 Cross, G. R. and A. K. Jain, Markov Random Field Texture Models. Ieee Transactions on Pattern Analysis and Machine Intelligence, 1983. 5(1): p. 25-39.
208 Keller, J. M., S. Chen, and R. M. Crownover, Texture Description and Segmentation through Fractal Geometry. Computer Vision Graphics and Image Processing, 1989. 45(2): p. 150-166.
209 Indahl, U. G. and T. Naes, Evaluation of alternative spectral feature extraction methods of textural images for multivariate modeling. Journal of Chemometrics, 1998. 12(4): p. 261-278.
210 Geladi, P., Some Special Topics in Multivariate Image-Analysis. Chemometrics and Intelligent Laboratory Systems, 1992. 14(1-3): p. 375-390.
211 Bovik, A. C., M. Clark, and W. S. Geisler, Multichannel Texture Analysis Using Localized Spatial Filters. Ieee Transactions on Pattern Analysis and Machine Intelligence, 1990. 12(1): p. 55-73.
212 Unser, M., Texture Classification and Segmentation Using Wavelet Frames. Ieee Transactions on Image Processing, 1995. 4(11): p. 1549-1560.
213 Laine, A. and J. Fan, Texture Classification by Wavelet Packet Signatures. Ieee Transactions on Pattern Analysis and Machine Intelligence, 1993. 15(11): p. 1186-1191.
214 Huang, J. and K. H. Esbensen, Applications of Angle Measure Technique (AMT) in image analysis Part I. A new methodology for in situ powder characterization. Chemometrics and Intelligent Laboratory Systems, 2000. 54(1): p. 1-19.
215 Petropulu, C. L. N. a. A. P., Higher-order spectra analysis: a nonlinear signal processing framework. 1993. PTR Prentice Hall.
216 Chandran, V., et al., Pattern recognition using invariants defined from higher order spectra: 2-D image inputs. Ieee Transactions on Image Processing, 1997. 6(5): p. 703-712.
217 Goatman K A, F. A., Philip S, Williams G J, Olson J A, Sharp P F, Detection of new vessels on the optic disc using retinal photographs. IEEE Trans Med Imaging, 2010. 13: p. Epub ahead of print.
218 Lee, S. C., et al., Comparison of diagnosis of early retinal lesions of diabetic retinopathy between a computer system and human experts. Arch Ophthalmol, 2001. 119(4): p. 509-15.
219 Niemeijer, M., et al., Automatic detection of red lesions in digital color fundus photographs. IEEE Trans Med Imaging, 2005. 24(5): p. 584-92.
220 Niemeijer, M., et al., Automated detection and differentiation of drusen, exudates, and cotton-wool spots in digital color fundus photographs for diabetic retinopathy diagnosis. Invest Ophthalmol Vis Sci, 2007. 48(5): p. 2260-7.
221 Abramoff, M. D., et al., Evaluation of a system for automatic detection of diabetic retinopathy from color fundus photographs in a large population of patients with diabetes. Diabetes Care, 2008. 31(2): p. 193-8.
222 Fleming A D, G. K., Williams G J, Automated detection of blot haemorrhages as a sign of referable diabetic retinopathy. Med Image Understand Anal, 2008: p. 235-9.
223 Fleming, A. D., et al., Automated detection of exudates for diabetic retinopathy screening. Physics in Medicine and Biology, 2007. 52(24): p. 7385-7396.
224 Usher, D., et al., Automated detection of diabetic retinopathy in digital retinal images: a tool for diabetic retinopathy screening. Diabet Med, 2004. 21(1): p. 84-90.

What is claimed is:

1. A method for diagnosing and/or predicting the presence, progression and/or treatment effect of a disease characterized by retinal pathological changes in a subject, comprising the steps of:
   (a) obtaining a retinal fundus image from the subject;
   (b) converting the image to a gray level image and/or extracting vessels from the image to obtain the gray level image and/or the vessel image;
   (c) performing statistical texture analysis on the gray level image and/or the vessel image, and generating one or more factors, wherein the statistical texture analysis includes using gray level co-occurrence matrix (GLCM) and/or run length matrix (RLM) to obtain texture features, including normalized Homogeneity, normalized Entropy, normalized Contrast, normalized $4^{th}$ moment and normalized Run percentage;
   (d) comparing the one or more factors obtained from step (c) with those of a control, a change of the factors is an indication of the presence, progression and/or treatment effect of the disease in the subject.

2. The method of claim 1, wherein the disease is selected from the group consisting of stroke, hypertension, diabetes, cardiovascular diseases including coronary heart disease and cerebral vascular disease, glaucoma, prematurity, papilloedema, and common retina disease.

3. The method of claim 1, wherein the disease is stroke, and step (c) includes performing the statistical texture analysis and at least one of fractal analysis, high order spectra analysis, and abnormal pattern analysis on the gray level image and/or the vessel image, and generating one or more factors.

4. The method of claim 1, wherein the disease is diabetes, and step (c) includes performing the statistical texture analysis and at least one of fractal analysis, high order spectra analysis, and abnormal pattern analysis on the gray level image and/or the vessel image, and generating one or more factors.

5. The method of claim 1, wherein step (b) includes using mathematical morphological operations and/or dual tree complex wavelet transform technique.

6. The method of claim 1, wherein step (c) further comprises performing one or two or three analyses selected from the group consisting of fractal analysis, high order spectra analysis, and abnormal pattern analysis on the gray level image and/or the vessel image, and generating one or more factors.

7. The method of claim 6, wherein the fractal analysis in step (c) includes using complex wavelet methods.

8. The method of claim 6, wherein the fractal analysis in step (c) includes using multifractal spectrum analysis.

9. The method of claim 6, wherein the factor generated by the fractal analysis is selected from the group consisting of Sum Average, Cluster Shade, Hausdorff dimension, and any combination thereof.

10. The method of claim 6, wherein the higher order spectral (HOS) features obtained from the high order spectra analysis in step (c) include Entropy1 HOS features at degree of 100, Entropy2 HOS features at degree of 160, Entropy3 HOS features at degree of 40, 140 and 160; Entropy Phase HOS features at degree of 40, 140, 160 and 180; Entropy Magnitude HOS features at degree of 0, 20, 40, 60, 100, 120, 140, 160 and 180.

11. The method of claim 6, wherein the abnormal pattern analysis in step (c) includes using a wavelet algorithm based on wavelet transform.

12. The method of claim 6, wherein the abnormal pattern analysis in step (c) includes using higher order spectral analysis in combination with a wavelet algorithm based on wavelet transform.

13. The method of claim 6, wherein the abnormal patterns include hemorrhages, exudates, new vessels, microaneurysm, proliferative vitreoretinopathy or any combination thereof.

14. The method of claim 13, wherein the abnormal patterns are hemorrhages.

15. A method for generating one or more factors associated with retinal pathological changes in a disease of a subject, comprising the steps of:
(a) obtaining a retinal fundus image from the subject;
(b) converting the image to a gray level image and/or extracting vessels from the image to obtain the gray level image and/or the vessel image; and
(c) performing statistical texture analysis on the gray level image and/or the vessel image, and generating one or more factors, wherein the statistical texture analysis includes using gray level co-occurrence matrix (GLCM) and/or run length matrix (RLM) to obtain texture features, including normalized Homogeneity, normalized Entropy, normalized Contrast, normalized $4^{th}$ moment and normalized Run percentage.

16. The method of claim 15, wherein the disease is selected from the group consisting of stroke, hypertension, diabetes, cardiovascular diseases including coronary heart disease and cerebral vascular disease, glaucoma, prematurity, papilloedema, and common retina disease.

17. The method of claim 15, wherein the disease is stroke, and step (c) includes performing the statistical texture analysis and at least one of fractal analysis, high order spectra analysis, and abnormal pattern analysis on the gray level image and/or the vessel image, and generating one or more factors.

18. The method of claim 15, wherein the disease is diabetes, and step (c) includes performing the statistical texture analysis and at least one of fractal analysis, high order spectra analysis, and abnormal pattern analysis on the gray level image and/or the vessel image, and generating one or more factors.

19. The method of claim 15, wherein step (b) includes using mathematical morphological operations and/or dual tree complex wavelet transform technique.

20. The method of claim 15, wherein step (c) further comprises performing one or two or three analyses selected from the group consisting of fractal analysis, high order spectra analysis, and abnormal pattern analysis on the gray level image and/or the vessel image, and generating one or more factors.

21. The method of claim 20, wherein the fractal analysis in step (c) includes using complex wavelet methods.

22. The method of claim 20, wherein the fractal analysis in step (c) includes using multifractal spectrum analysis.

23. The method of claim 20, wherein the factor generated by the fractal analysis is selected from the group consisting of Sum Average, Cluster Shade, Hausdorff dimension, and any combination thereof.

24. The method of claim 20, wherein the higher order spectral (HOS) features obtained from the high order spectra analysis in step (c) include Entropy1 HOS features at degree of 100, Entropy2 HOS features at degree of 160, Entropy3 HOS features at degree of 40, 140 and 160; Entropy Phase HOS features at degree of 40, 140, 160 and 180; Entropy Magnitude HOS features at degree of 0, 20, 40, 60, 100, 120, 140, 160 and 180.

25. The method of claim 20, wherein the abnormal pattern analysis in step (c) includes using a wavelet algorithm based on wavelet transform.

26. The method of claim 20, wherein the abnormal pattern analysis in step (c) includes using higher order spectral analysis in combination with a wavelet algorithm based on wavelet transform.

27. The method of claim 20, wherein the abnormal patterns include hemorrhages, exudates, new vessels, microaneurysm, proliferative vitreoretinopathy or any combination thereof.

28. The method of claim 27, wherein the abnormal patterns are hemorrhages.

29. A device for diagnosing and/or predicting the presence, progression and/or treatment effect of a disease characterized by retinal pathological changes in a subject, comprising:
an image-capturing module for obtaining a retinal fundus image from the subject;
a conversion module for converting the image to a gray level image and/or extracting vessels from the image to obtain said gray level image and/or vessel image; and
an analysis module comprising a statistical texture analysis submodule for performing analysis on the gray level image and/or vessel image and generating one or more factors, wherein the statistical texture analysis submodule is configured to carry out gray level co-occurrence matrix (GLCM) and/or run length matrix (RLM) to obtain texture features, including normalized Homogeneity, normalized Entropy, normalized Contrast, normalized $4^{th}$ moment and normalized Run percentage.

30. The device of claim 29, wherein the disease is selected from the group consisting of stroke, hypertension, diabetes, cardiovascular diseases including coronary heart disease and cerebral vascular disease, glaucoma, prematurity, papilloedema, and common retina disease.

31. The device of claim 29, wherein the disease is stroke, and the analysis module comprises the statistical texture analysis submodule and at least one of a fractal analysis submodule, a high order spectra analysis submodule, and an abnormal pattern analysis submodule for performing analysis on the gray level image and/or vessel image and generating one or more factors.

32. The device of claim 29, wherein the disease is diabetes, and the analysis module comprises the statistical texture analysis submodule and at least one of a fractal analysis submodule, a high order spectra analysis submodule, and an abnormal pattern analysis submodule for performing analysis on the gray level image and/or vessel image and generating one or more factors.

33. The device of claim 29, wherein the conversion module is configured to carry out mathematical morphological operations and/or dual tree complex wavelet transform technique.

34. The device of claim 29, wherein the analysis module further comprises one or two or three submodules selected from the group consisting of a fractal analysis submodule, a high order spectra analysis submodule, and an abnormal pattern analysis submodule for performing analysis on the gray level image and/or vessel image and generating one or more factors.

35. The device of claim 34, wherein the fractal analysis submodule is configured to carry out complex wavelet methods.

36. The device of claim 34, wherein the fractal analysis submodule is configured to carry out multifractal spectrum analysis.

37. The device of claim 34, wherein the factor generated by the fractal analysis submodule is selected from the group consisting of Sum Average, Cluster Shade, Hausdorff dimension, and any combination thereof.

38. The device of claim 34, wherein the higher order spectral (HOS) features generated by the high order spectra analysis submodule include Entropy1 HOS features at degree of 100, Entropy2 HOS features at degree of 160, Entropy3 HOS features at degree of 40, 140 and 160; Entropy Phase HOS features at degree of 40, 140, 160 and 180; Entropy Magnitude HOS features at degree of 0, 20, 40, 60, 100, 120, 140, 160 and 180.

39. The device of claim 34, wherein the abnormal pattern analysis submodule is configured to carry out a wavelet algorithm based on wavelet transform.

40. The device of claim 34, wherein the abnormal pattern analysis submodule is configured to carry out higher order spectral analysis in combination with a wavelet algorithm based on wavelet transform.

41. The device of claim 34, wherein the abnormal patterns analyzed by the abnormal pattern analysis submodule include hemorrhages, exudates, new vessels, microaneurysm, proliferative vitreoretinopathy or any combination thereof.

42. The device of any of claim 41, wherein the abnormal patterns are hemorrhages.

43. The method of claim 2, wherein the common retina disease is macular hole or age-related macular degeneration.

44. The method of claim 7, wherein the fractal analysis in step (c) includes using complex wavelet Leader multifractal analysis.

45. The method of claim 11, wherein the abnormal pattern analysis in step (c) includes using a dual tree complex wavelet transform and a wavelet-based Radon transform.

46. The method of claim 12, wherein the wavelet algorithm based on wavelet transform is a dual tree complex wavelet transform and a wavelet-based Radon transform.

47. The method of claim 16, wherein the common retina disease is macular hole or age-related macular degeneration.

48. The method of claim 21, wherein the fractal analysis in step (c) includes using complex wavelet Leader multifractal analysis.

49. The method of claim 25, wherein the abnormal pattern analysis in step (c) includes using a dual tree complex wavelet transform and a wavelet-based Radon transform.

50. The method of claim 26, wherein the wavelet algorithm based on wavelet transform is a dual tree complex wavelet transform and a wavelet-based Radon transform.

51. The device of claim 29, further comprising a comparison module for comparing the factors obtained from the analysis module with those of a control.

52. The device of claim 30, wherein the common retina disease is macular hole or age-related macular degeneration.

53. The device of claim 35, wherein the fractal analysis submodule is configured to carry out complex wavelet Leader multifractal analysis.

54. The device of claim 39, wherein the abnormal pattern analysis submodule is configured to carry out a dual tree complex wavelet transform and a wavelet-based Radon transform.

55. The device of claim 40, wherein the wavelet algorithm based on wavelet transform is a dual tree complex wavelet transform and a wavelet-based Radon transform.

\* \* \* \* \*

UNITED STATES PATENT AND TRADEMARK OFFICE
CERTIFICATE OF CORRECTION

PATENT NO. : 8,787,638 B2  
APPLICATION NO. : 13/441181  
DATED : July 22, 2014  
INVENTOR(S) : Benny Chung-Ying Zee et al.

Page 1 of 1

It is certified that error appears in the above-identified patent and that said Letters Patent is hereby corrected as shown below:

In the Claims,

Column 60, Line 30:
"and normalized Run percentage;" should read, --and normalized Run percentage; and--.

Signed and Sealed this
Thirty-first Day of March, 2015

Michelle K. Lee
*Director of the United States Patent and Trademark Office*